US007452865B2

(12) United States Patent
Schally et al.

(10) Patent No.: US 7,452,865 B2
(45) Date of Patent: Nov. 18, 2008

(54) ANTAGONISTIC ANALOGS OF GH RH (2003)

(75) Inventors: Andrew V. Schally, Miami, FL (US); Jozsef Varga, Metairie, LA (US); Marta Zarandi, Szeged (HU); Ren Zhi Cai, New Orleans, LA (US)

(73) Assignees: The Administrare's of the Tulane Educational Fund, New Orleans, LA (US); United States of America by Dept of Veterans Affairs, Washington, DC (US)

( * ) Notice: Subject to any disclaimer, the term of this patent is extended or adjusted under 35 U.S.C. 154(b) by 0 days.

(21) Appl. No.: 10/566,776

(22) PCT Filed: Jul. 26, 2004

(86) PCT No.: PCT/US2004/024183

§ 371 (c)(1),
(2), (4) Date: Oct. 2, 2006

(87) PCT Pub. No.: WO2005/016953

PCT Pub. Date: Feb. 24, 2005

(65) Prior Publication Data

US 2007/0042950 A1  Feb. 22, 2007

(51) Int. Cl.
*A61K 38/00* (2006.01)
*A61K 38/16* (2006.01)
*A61K 38/25* (2006.01)
*C07K 14/00* (2006.01)

(52) U.S. Cl. .................. 514/12; 514/2; 514/9; 514/10; 514/11; 530/324; 530/317

(58) Field of Classification Search ........................ None
See application file for complete search history.

(56) References Cited

U.S. PATENT DOCUMENTS 6,057,422 A * 5/2000 Schally et al. ............... 530/324
7,026,281 B1 * 4/2006 Schally et al. ................ 514/2

OTHER PUBLICATIONS

Voskoglou-Nomikos T, Pater JL, Seymour L, Clinical Predictive Value of the Vitro Cell Line, Human Xenograft, and Mousr Allograft Preclinical Cancer Models, Clinical Cancer Research, 2003, 9: 4227-4239.*
Auerbach, R, Akhtar N, Lewis RL, SHinners BL, Angiogenesis assays: Problems and pitfalls, Cancer and Metastasis Reviews, 2000, 19: 167-172.*
Jain RK, Schlenger K, Hockel M, Yuan F, Quantitative angiogenesis assays: Progress and Problems, Nature, 1997, 3(11):1203-1208.*
Freshney RI, Cultures of Animal Cells, A Manual of Basic Technique, Alan R. Liss, Inc., 1983, New York, pp. 3-4.*
Dermer GB, ANother Anniversay for the War on Cancer, Bio/Technology, 1994, 12: 320.*
MSNBC News Services, Mixed results on new cancer drug, Nov. 9, 2000, 1-4 enclosed.*
Gura T, Systems for Identifying New Drugs Are Often Faulty, Science, 1997, 278(7): 1041-1042.*

* cited by examiner

*Primary Examiner*—Anish Gupta
*Assistant Examiner*—Julie Ha
(74) *Attorney, Agent, or Firm*—Omri M. Behr

(57) ABSTRACT

There is provided a novel series of synthetic antagonistic analogs of hGH-RH(1-29)NH$_2$. These analogs inhibit the activity of endogenous hGH-RH on the pituitary GH-RH receptors, and therefore prevent the release of growth hormone. The analogs also inhibit the proliferation of human cancers through a direct effect on the cancer cells. The higher inhibitory potencies of the new analogs, as compared to previously described ones, results from replacement of various amino acids.

11 Claims, No Drawings

ANTAGONISTIC ANALOGS OF GH RH (2003)

FIELD OF INVENTION

This invention was made in part with Government support from the Medical Research Service of the Veterans Affairs Department The Government has certain rights in this application (VA No. 03-084, assigned Jul. 25, 2003).

The present invention relates to novel synthetic peptides that inhibit the release of growth hormone from the pituitary in mammals as well as inhibit the proliferation of human cancers through a direct effect on the cancer cells, and to therapeutic compositions containing these novel peptides.

BACKGROUND OF THE INVENTION

Growth hormone-releasing hormone (GH-RH) is a peptide belonging to the secretin/glucagon family of neuroendocrine and gastrointestinal hormones, a family that also includes vasoactive intestinal peptide (VIP), pituitary adenylate cyclase activating peptide (PACAP) and others. Human GH-RH (hGH-RH) peptide is comprised of 44 amino acid residues. The best known site of production of GH-RH is the hypothalamus, but it was found that various peripheral organs also synthesize it hGH-RH is also produced, sometimes in large quantities, by human malignant tissues (cancers) of diverse origin.

GH-RH exerts various physiological and pathophysiological functions. Hypothalamic GH-RH is an endocrine releasing hormone that, acting through specific GH-RH receptors on the pituitary, regulates the secretion of pituitary growth hormone (GH). The physiological functions of GH-RH in extrapituitary tissues are less clear. However, there is increasing evidence for the role of GH-RH as an autocrine|paracrine growth factor in various cancers. Splice variant (SV) receptors for GH-RH, different from those expressed in the pituitary, have been described in a wide range of human cancers and in some normal peripheral organs. The actions of tumoral autocrine/paracrine GH-RH could be exerted on these receptors. In addition, receptors for VIP and other, as yet unidentified receptors of this family, could all be targets of local GH-RH.

In view of the role of GH-RH as an endocrine regulator of GH release, novel therapeutic strategies, based on the use of agonistic and antagonistic analogs of GH-RH, have been devised for the treatment of various pathological conditions.

GH is a polypeptide having 191 amino acids that stimulates the production of different growth factors, e.g. insulin-like growth factor I (IGF-I), and consequently promotes growth of numerous tissues (skeleton, connective tissue, muscle and viscera) and stimulates various physiological activities (raising the synthesis of nucleic acids and proteins, and raising lipolysis, but lowering urea secretion). Release of pituitary GH is under the control of releasing and inhibiting factors secreted by the hypothalamus, the primary releasing factors being GH-RH and ghrelin, and the main inhibiting factor being somatostatin.

GH has been implicated in several diseases. One disease in which GH is involved is acromegaly, in which excessive levels of GH are present The abnormally enlarged facial and extremity bones, and the cardiovascular symptoms of this disease can be treated by administering a GH-RH antagonist Further diseases involving GH are diabetic retinopathy and diabetic nephropathy. The damage to the retina and kidneys respectively in these diseases, believed to be due to hypersecretion of GH, results in blindness or reduction in kidney function. This damage can be prevented or slowed by administration of an effective GH-RH antagonist In an effort to intervene in these disease and other conditions, some investigators have attempted to control GH and IGF-I levels by using analogs of somatostatin, an inhibitor of GH release. However, somatostatin analogs, if administered alone, do not suppress GH or IGF-I levels to a desired degree. If administered in combination with a GH-RH antagonist, somatostatin analogs will suppress IGF-I levels much better.

However, the main applications of GH-RH antagonists are in the field of cancer (reviewed in Schally A V and Varga J L, Trends Endocrinol Metab 10: 383-391, 1999; Schally A V et al, Frontiers Neuroendocrinol 22: 248-291, 2001; Schally A V and Comaru-Schanlly A M, in: Kufe D W, Pollock R E, Weichselbaum R R, Bast Jr. R C, Gansler T S, Holland J F, Frei III E, Eds. Cancer Medicine, $6^{th}$ ed. Hamilton, Ontario: BC. Decker, Inc., 2003, p. 911-926). GH-RH antagonists inhibit the proliferation of malignancies by indirect endocrine mechanisms based on the inhibition of pituitary GH release and resulting in the decrease of serum levels of GH and IGF-I, as well as by direct effects on the tumor tissue.

GH-RH and its tumoral splice variant (SV) receptors are present in human cancers of the lung, prostate, breast, ovary, endometrium, stomach, intestine, pancreas, kidney, and bone (see Halmos G et al, Proc Natl Acad Sci USA 97: 10555-10560, 2000; Rekasi Z et al, Proc Natl Acad Sci USA 97: 10561-10566, 2000; Schally A V et al, Frontiers Neuroendocrinol 22: 248-291, 2001; Schally A V and Comaru-Schally A M, in: Kufe D W, Pollock R E, Weichselbaum R R, Bast Jr. R C, Gansler T S, Holland J F, Frei III E, Eds. Cancer Medicine, IP ed. Hamilton, Ontario: BC. Decker, Inc., 2003, p. 911-926). Tumoral GH-RH has been shown or it is suspected to act as an autocrine growth factor in these malignancies. Antagonistic analogs of GH-RH can inhibit the stimulatory activity of GH-RH and exert direct antiproliferative effects in vitro on cancer cells, and in vivo on tumors. Direct antiproliferative effects of GH-RH antagonists are exerted on tumoral receptors (binding sites). In addition to the specific tumoral SV receptors for GH-RH, receptors for VIP and other, as yet unidentified receptors of this family, are targets of GH-RH antagonists.

In addition to endocrine inhibitory effects on serum GH and IGF-I, GH-RH antagonists have been found to reduce the autocrine and paracrine production of several tumor growth factors and/or downregulate their receptors. These growth factors include IGF-I, IGF-II, GH, vascular endothelial growth factor (VEGF), and fibroblast growth factor (FGF), Thus, a disruption of the autocrine|paracrine stimulatory loops based on these growth factors contributes to the efficacy of GH-RH antagonists as antitumor agents.

IGF-I and IGF-II are autocrine/paracrine growth factors with potent mitogenic effects on various cancers. IGF-I is also an endocrine growth factor, and elevated levels of serum IGF-I are considered an epidemlological risk factor for the development of prostate cancer, lung cancer, and colorectal cancer. The involvement of IGF-I (somatomedin-C) in breast cancer, prostate cancer, colon cancer, bone tumors and other malignancies is well established. Nevertheless, autocnne/paracrine control of proliferation by IGF-II is also a major factor in many tumors. IGF-I and IGF-II exert their proliferative and anti-apoptotic effects through the common IGF-I receptor. The receptors for IGF-I are present in primary human breast cancers, prostate cancers, lung cancers, colon cancers, brain tumors, pancreatic cancers, and in renal cell carcinomas. In several experimental cancers, such as those of the bone, lung, prostate, kidney, breast, ovary, intestine, pancreas, and brain, treatment with GH-RH antagonists produces a reduction in IGF-I and/or IGF-II levels, concomitant to inhibition of tumor growth (reviewed in Schally A V and Varga J L, Trends Endocrinol Metab 10: 383-391, 1999; Schally A V et al, Frontiers Neuroendocrinol 22: 248-291, 2001; Schally A V and ComaruSchally A M, in: Kufe D W, Pollock R E, Weichselbaum R R, Bast Jr. R C, Gansler T S, Holland J F, Frei III E, Eds. Cancer Medicine, 6th ed. Hamilton, Ontario: BC. Decker, Inc., 2003, p. 911-926). In some cases, the expression of IGF-I receptors was also decreased by GH-RH antagonists. Thus the disruption of endocrine and autocrine/paracrine stimulatory loops dependent on IGF-I and IGF-II contributes to the antitumor effect of GH-RH antagonists.

In MXT breast cancer model, treatment with GH-RH antagonists inhibited tumor growth, reduced the mRNA level for GH and the concentration of GH peptide in tumors, and inhibited the mRNA expression for GH receptors (Szepeshazi K et al, Endocrinology 142: 4371-4378, 2001). GH was shown to act as a growth factor for MXT murine mammary carcinoma cells, MCF-7 human breast cancer cells and other tumor cell lines. Thus the inhibitory activity of GH-RH antagonists on local and serum GH levels contributes to their antitumor effect GH-RH antagonists have been shown to inhibit the mRNA levels and protein concentrations of VEGF in human androgen-sensitive and androgen-independent prostate cancer models (Letsch M et al, Proc Nati Acad Sci USA 100: 1250-1255, 2003; Plonowski A et al, Prostate 52: 173-182, 2002) and this phenomenon contributes to their antitumor effect since VEGF plays an important stimulatory role in the neovascularization and growth of various tumors. Moreover, it was found that a GH-RH antagonist inhibited the VEGF secretion and proliferation of normal murine endothelial cells, apparently through a direct effect on these cells in vitro (Siejka A et al, Life Sci 72: 2473-2479, 2003).

Scientists have investigated various modifications of GH-RH to elucidate the relationship of the structure of GH-RH to its activity on the pituitary receptors, in an effort to provide synthetic congeners with improved agonistic or antagonistic properties. Thus, it was early established that GH-RH fragment comprising residues 1 to 29, or GH-RH(1-29), is the minimum sequence necessary for biological activity on the pituitary. This fragment retains 50% or more of the potency of native GH-RH. Subsequently, many synthetic analogs of GH-RH, based on the structure of hGH-RH(1-29)NH$_2$ peptide, were prepared. hGH-RH(1-29)NH$_2$ has the following amino acid sequence:

Tyr-Ala-Asp-Ala-Ile$^5$-Phe-Thr-Asn-Ser-Tyr$^{10}$-Arg-Lys-Val-Leu-Gly$^{15}$-Gln-Leu-Ser-Ala-Arg$^{20}$-Lys-Leu-Leu-Gln-Asp$^{25}$-Ile-Met-Ser-Arg$^{29}$-NH$_2$

A considerable number of patents and articles in the open literature disclose analogs of GH-RH which either act as agonists of GH-RH (i.e. act to stimulate the release of GH) or as antagonists of GH-RH (i.e. act to inhibit the release of GH) on the pituitary. Most of these peptides are derived from the GH-RH(1-29) peptide sequence, with specific structural modifications which account for their enhanced agonistic or antagonistic properties on the pituitary receptors. However, apart from a few exceptions, it is not known how these analogs would behave on cancer cells that express GH-RH receptors different from those found in the pituitary. Only a few published scientific studies tried to elucidate the structure-activity relationships and characterize the direct antagonistic (or agonistc) effects of GH-RH analogs on cancer cells and tumors (see Rekasi Z et al, Endocrinology 141: 2120-2128, 2000; Halmos G et al, Proc Natl Acad Sci USA 97: 10555-10560, 2000; Rekasi Z et al, Proc Natl Acad Sci USA 97: 10561-10566, 2000; Kiaris H et al, Proc Natl Acad Sci USA 99: 196-200, 2002), and no issued patents have dealt with this issue so far. Consequently, very little is known about the structural features in GH-RH analogs required for a direct antagonistic action on tumor cells.

The first described GH-RH antagonist, [Ac-Tyr$^1$,D-Arg$^2$] hGH-RH(1-29)NH$_2$, which is generally termed as the "standard antagonist" in the literature, was found to prevent the activation of rat anterior pituitary adenylate cyclase by hGH-RH(1-29)NH$_2$. The same peptide blocked the action of GH-RH on its receptors in the pituitary and hypothalamus, and inhibited the pulsatile growth hormone secretion. The standard antagonist was also evaluated clinically (Ocampo-Lim B et al, J Clin Endocrinol Metab 81: 4396-4399, 1996; Jaffe C A et al, J Clin Endocrinol Metab 82: 634-637, 1997). Large doses of this antagonist (400 μg/kg) eliminated nocturnal GH secretion in normal subjects and inhibited the response to GH-RH. The standard GH-RH antagonist also reduced GH levels in a patient with acromegaly. However, for clinical use, much more potent antagonists of GH-RH are required.

The inventions mentioned below disclose GH-RH analogs with antagonistic or agonistic properties on the pituitary receptors for GHRH. However it was not reported and not investigated whether these analogs could exert direct effects on tumor cells.

U.S. Pat. No. 4,659,693 discloses GH-RH antagonistic analogs which contain certain N,N'-dialkyl-omega-guanidino alpha-mino acyl residues in position 2 of the GH-RH(1-29) sequence.

Published application WO 91/16923 reviews earlier attempts to alter the secondary structure of hGH-RH by modifying its amino acid sequence. These earlier attempts include: replacing Tyr$^1$, Ala$^2$, Asp$^3$ or Asn$^8$ with their D-isomers; replacing Asn$^8$ with L- or D-Ser, D-Arg, Asn, Thr, Gln or D-Lys; replacing Ser$^8$ with Ala to enhance amphiphilicity of the region; and replacing Gly$^{15}$ with Ala or Alb. When R$^2$ in the analogs is D-Arg, and R$^8$, R$^9$, and R$^{15}$ are substituted as indicated above, antagonistic activity is said to result These antagonistic peptides are said to be suitable for administration as pharmaceutical compositions to treat conditions associated with excessive levels of GH, e.g., acromegaly.

The antagonistic activity of the hGH-RH analogue "[Ser$^8$-psi[CH$_2$—NH]-Tyr$^{10}$]hGH-RH(1-29)" of U.S. Pat. No. 5,084,555 was said to result from the pseudopeptide bond (i.e., a peptide bond reduced to a [CH$_2$—NH] linkage) between the R$^9$ and R$^{10}$ residues. However, the antagonistic properties of [Ser$^9$-psi[CH$_2$—NH]-Tyr$^{10}$]hGH-RH(1-29) were said to be inferior to the standard antagonist, [N-Ac-Tyr$^1$, D-Arg$^2$]hGH-RH(1-29)-NH$_2$.

U.S. Pat. Nos. 5,550,212, 5,942,489, and 6,057,422, assigned to the same assignee as the present application, disclose analogs of hGH-RH(1-29)NH$_2$ said to have enhanced antagonistic properties and prolonged duration of action regarding the inhibition of GH-RH-evoked GH release. These properties are believed to result from replacement of various amino acids and acylation with aromatic or nonpolar acids at the N-terminus of GH-RH(1-29)NH$_2$. The tumor inhibitory properties of antagonists featured in U.S. Pat. Nos. 5,942,489 and 6,057,422 have been demonstrated by using nude mice bearing xenografts of experimental human cancer models. It is noted that in U.S. Pat. Nos. 5,550, 212, and in 5,942,489, R$^9$ is always Ser, while R$^{11}$ and R$^{20}$ can be either Arg, D-Arg, or Cit. In the case of U.S. Pat. No. 6,057,422, R$^9$ can be either Arg, Har, Lys, Orn, D-Arg, D-Har, D-Lys, D-Orn, Cit, Nle, Tyr(Me), Ser, Ala, or Alb, while R$^{11}$ and R$^{20}$ are always Arg.

SUMMARY OF THE INVENTION

There is provided a novel series of synthetic analogs of hGH-RH(1-29)NH$_2$ and hGH-RH(1-30)NH$_2$. These analogs inhibit the release of growth hormone from the pituitary in mammals as well as inhibit the proliferation of human cancers through a direct effect on the cancer cells. The stronger inhibitory potencies of the new analogs, as compared to previously described ones, results from replacement of various amino acids.

The invention principally relates to peptides comprising the formulae:

R$_1$-A$^0$-A$^1$-A$^2$-Asp-Ala-A$^5$-A$^6$-Thr-A$^8$-A$^9$-A$^{10}$-A$^{11}$-A$^{12}$-Val-Leu-A$^{15}$-A$^{16}$-Leu-Ser-A$^{19}$-A$^{20}$-A$^{21}$-A$^{22}$-Leu-Gln-Asp-Ile-A$^{27}$-A$^{28}$-A$^{29}$-A$^{30}$-R$_2$ wherein R$_1$ is a member of the group consisting of a) PhAc, Hca, Dat, IndAc, Ipa, 1-Nac, 2-Nac, 1-Npr, 2-Npr, Ibu; CH$_3$(CH$_2$)$_n$CO, or HOOC(CH$_2$)$_n$CO, where n is an integer from 2 to 20, and b) any other straight chain, cyclic, branch chain, saturated, unsaturated or poly unsaturated aliphatic carboxyl group of 6-14 carbon atoms and any carbocyclic or heterocyclic aromatic carboxyl group of 3-8 carbon atoms containing up to one atom each of the group S, N, and O in the heterocyclic ring, A$^0$ is Phe, D-Phe, Arg, D-Arg, or a carbon-nitrogen single bond,
A$^1$ is Tyr or His,
A$^2$ is D-Arg or D-Cit,
A$^5$ is Ile or Val,
A$^6$ is Phe, Tyr, Nal, or Phe(Y), in which Y=F, Cl, Br, or I,
A$^8$ is Asn, D-Asn, Cit, D-Cit, Gln, D-Gln, Ser, D-Ser, Thr, D-Thr, Ala, DAla, Abu, D-Abu, or Aib,
A$^9$ is His, D-His, Amp, D-Amp, Gup, or DGup,
A$^{10}$ is Tyr, Tyr(Et), Tyr(Me); Phe(Y), in which Y=H, F, Cl, Br, or I; Amp, His, Cha, Chg, Bpa, Dip, Trp, Trp(For), Tpl, 1-Nal, 2-Nal, 3-Pal, 4-Pal, Phe(NH$_2$), or Phe(NO$_2$),
A$^{11}$ is His, D-His, Arg, D-Arg, Cit, Har, D-Har, Amp, D-Amp, Gup, or D-Gup,
A$^{12}$ is Lys, D-Lys, Orn, D-Orn, Har, D-Har, Cit, D-Cit, Nle, or Ala,
A$^{15}$ is Gly, Ala, Abu, Aib, Nle, Gln, Cit, or His,
A$^{16}$ is Gln or Arg,
A$^{19}$ is Ala or Abu,
A$^{20}$ is His, D-His, Arg, D-Arg, or Cit,
A$^{21}$ is Lys, D-Lys, Orn, D-Orn, Cit, or D-Cit,
A$^{22}$ is Leu, Ala or Aib,
A$^{27}$ is Met, Leu, Nle, Abu, or D-Arg,
A$^{28}$ is Arg, D-Arg, Har, D-Har, Ser, Asn, Asp, Ala, Abu, or Cit.
A$^{29}$ is Arg, D-Arg, Har, D-Har, Cit, D-Cit, or Agm,
A$^{30}$ is Arg, D-Arg, Har, D-Har, Cit, D-Cit, Agm, or is a carbon-nitrogen or carbon-oxygen single bond,
R$_2$ is —NH$_2$, —NH—NH$_2$, —NH—OH, —NHR$_3$, —NR$_3$R$_4$, —OH, or —OR$_3$, in which R$_3$ and R$_4$ are any of C$_{1-10}$ alkyl, C$_{2-10}$ alkenyl, C$_{2-10}$ alkinyl, C$_{7-16}$ phenylalkyl, —C$_6$H$_5$, or —CH(C$_6$H$_5$)$_2$;

provided that if A$^{29}$ is Agm then A$^{30}$ and R$_2$ are absent, and if A$^{30}$ is Agm then R$_2$ is absent, and pharmaceutically acceptable salts thereof.

Among the preferred embodiment are peptides in the formula above wherein one or both of A$^{11}$ and A$^{20}$ are other than Arg, D-Arg, or Cit.

Specifically, the principal peptides falling under this genus are:

[PhAc-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 67

[PhAc-Tyr$^1$, D-Arg$^2$, Phe(pCl)$^6$, Amp$^9$, Abu$^{15}$, Nle$^{27}$, D-Arg$^{28}$, Har$^{29}$]hGH-RH(1-29)NH$_2$ Peptide 68

[PhAc-Tyr$^1$, D-Arg$^2$, Phe(pCl)$^6$, His$^9$, Tyr(Me)$^{10}$, Abu$^{15}$, Nle$^{27}$, D-Arg$^{28}$, Har$^{29}$]hGH-RH(1-29)NH$_2$ Peptide 69

[CH$_3$(CH$_2$)$_6$CO-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 70

[HOOC(CH$_2$)$_8$CO-Tyr$^1$, D-Arg$^2$, Phe(pCl)$^6$, Amp$^9$, Tyr(Me)$_{10}$, Abu$^{15}$, Nle$^{27}$, D-Arg$^{28}$, Har$^{29}$]hGH-RH(1-29)NH$_2$ Peptide 71

[HOOC(CH$_2$)$_{12}$CO-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 72

[PhAc-Tyr$^1$, D-Arg$^2$, Phe(pCl)$^6$, Amp$^9$, Tyr(Me)$^{10}$, His$^{11}$, Abu$^{15}$, Nle$^{27}$, D-Arg$^{28}$, Har$^{29}$]hGH-RH(1-29)NH$_2$ Peptide 73

[PhAc-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$^{29}$]hGH-RH(1-29)NH$_2$ Peptide 74

[1'-Nac-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$^{29}$]hGH-RH(1-29)NH$_2$ Peptide 75

[CH$_3$(CH$_2$)$_6$CO-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$,Har$^{29}$]hGH-RH(1-29)NH$_2$ Peptide 76

[HOOC(CH$_2$)$_{12}$CO-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$_{29}$]hGH-RH(1-29)NH$_2$ Peptide 77

[CH$_3$(CH$_2$)$_6$CO-Tyr$^1$, D-Arg$^2$, Phe(pCl)$^6$, Cit$^8$, Amp$^9$, Tyr(Et)$^{10}$, His$^{11}$, Abu$^{15}$, Nle$^{27}$D-Arg$^{28}$, Har$_{29}$]hGH-RH(1-29)NH$_2$ Peptide 78

[CH$_3$(CH$_2$)$_6$CO-Tyr$^1$, D-Arg$^2$, Phe(pCl)$^6$, Cit$^8$, His$^9$, Tyr(Et)$^{10}$, His$^{11}$, Abu$^{15}$, Nle$^{27}$, D-Arg$^{28}$, Har$_{29}$]hGH-RH(1-29)NH$_2$ Peptide 79

[CH$_3$(CH$_2$)$_6$CO-Tyr$^1$, D-Arg$^2$, Phe(pCl)$^6$, Ala$^8$, His$^9$, Tyr(Et$^{10}$, His$^{11}$, Abu$^{15}$, Nle$^{27}$, D-Arg$^{28}$, Har$_{29}$]hGH-RH(1-29)NH$_2$ Peptide 80

[HOOC(CH$_2$)$_8$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$_{29}$]hGH-RH(1-29)NH$_2$ Peptide 81

[HOOC(CH$_2$)$_{12}$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$_{29}$]hGH-RH(1-29)NH$_2$ Peptide 82

[CH$_3$(CH$_2$)CO-Tyr$^1$, D-Arg$^2$, Phe(pCl)$^6$, Ala$^8$, His$^9$, Tyr(Et)$^{10}$, His$^{11}$, Abu$^{15}$, His$^{20}$, Nle$^{27}$, D-Arg$^{28}$, Har$_{29}$]hGH-RH(1-29)NH$_2$ Peptide 86

[CH$_3$(CH$_2$)$_6$CO-Tyr$^1$, D-Arg$^2$, Phe(pCl)$^6$, Ala$^8$, Amp$^9$, Tyr(Et)$^{10}$, His$^{11}$, Abu$^{15}$, His$^{20}$, Nle$^{27}$, D-Arg$^{28}$, Har$_{29}$]hGH-RH(1-29)NH$_2$ Peptide 87

[HOOC(CH$_2$)$_{12}$CO-Tyr$^1$, D-Arg$^2$, Phe(pCl)$^6$, Ala$^8$, His$^9$, Tyr(Et)$^{10}$, His$^{11}$, Abu$^{15}$, His$^{20}$, Nle$^{27}$, D-Arg$^{28}$, Har$_{29}$]hGH-RH(1-29)NH$_2$ Peptide 88

[HOOC(CH$_2$)$_2$CO-Tyr$^1$, D-Arg$^2$, Phe(pCl)$^6$, Ala$^8$, Amp$^9$, Tyr(Et)$^{10}$, His$^{11}$, Abu$^{15}$, His$^{20}$, Nle$^{27}$, D-Arg$^{28}$, Har$_{29}$]hGH-RH(1-29)NH$_2$ Peptide 89

[1-Nac-Tyr$^1$, D-Arg$^4$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NH$_2$ Peptide 91

[CH$_3$(CH$_2$)$_6$CO-Tyr$^1$, D-Arg$^2$, Phe(pCl)$^6$, His$^9$, Tyr(Et)$^{10}$, His$^{11}$, Abu$^{15}$, Nle$^{27}$, D-Arg$^{28}$, Har$^{29}$]hGH-RH(1-29)NH$_2$ Peptide 92

[CH$_3$(CH$_2$)$_6$CO-Tyr$^1$, D-Arg$^2$, Phe(pCl)$^6$, Ala$^8$, His$^9$, Cit$^{15}$, Nle$^{27}$, D-Arg$^{28}$, Har$^{29}$]hGH-RH(1-29)NH$_2$ Peptide 93

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, His$^{15}$, His$^{20}$, Nle$^{27}$, D-Arg$^{28}$, Har$^{29}$]hGH-RH(1-29)NH$_2$ Peptide 94

[CH₃(CH₂)₆CO-Tyr¹, D-Arg², Phe(pCl)⁶, Ala⁸, His⁹, Tyr(Et)¹⁰, His¹¹, Orn¹², Abu¹⁵, Orn²¹, Nle²⁷, D-Arg²⁸, Har²⁹]hGH-RH(1-29)NH₂ Peptide 95

[CH₃(CH₂)₆CO-Tyr¹, D-Arg², Phe(pCl)⁶, Ala⁸, His⁹, Tyr(Et)¹⁰, His¹¹, Orn¹², Abu¹⁵, His²⁰, Orn²¹, Nle²⁷, D-Arg²⁸, Har²⁹]hGH-RH(1-29)NH₂ Peptide 96

[CH₃(CH₂)₆CO-Tyr¹, D-Arg², Phe(pCl)⁶, Ala⁶, His⁹, Tyr(Et)¹⁰, His¹¹, Abu¹⁵, Nle²⁷, D-Arg²⁸, Har²⁹]hGH-RH(1-29)NHEt Peptide 97

[CH₃(CH₂)₈CO-Tyr¹, D-Arg², Phe(pCl)⁶, Ala⁸, His⁹, Tyr(Et)¹⁰, His¹¹, Abu¹⁵, Nle²⁷, D-Arg²⁸, Har²⁹]hGH-RH(1-29)NHEt Peptide 98

[CH₃(CH₂)₁₀CO-Tyr¹, D-Arg², Phe(pCl)⁶, Ala⁸, His⁹, Tyr(Et)¹⁰, His¹¹, Abu¹⁵, Nle²⁷, D-Arg²⁸, Har²⁹]hGH-RH(1-29)NHEt Peptide 99

[Hca-Tyr¹, D-Arg², Phe(pCl)⁶, Ala⁸, His⁹, Tyr(Et)¹⁰, His¹¹, Abu¹⁵, Nle²⁷, D-Arg²⁸, Har²⁹]hGH-RH(1-29)NHEt Peptide 100

[CH₃(CH₂)₆CO-Tyr¹, D-Arg², Phe(pCl)⁶, Ala⁸, His⁹, Tyr(Et)¹⁰, His¹¹, Abu¹⁵, Nle²⁷, D-Arg²⁸, Har²⁹]hGH-RH(1-29)NHMe Peptide 101

[HOOC(CH₂)₁₂CO-Tyr¹, D-Arg², Phe(pCl)⁶, Ala⁸, His⁹, Tyr(Et)¹⁰, His¹¹, Orn¹² Abu¹⁵, His²⁰, Orn²¹, Nle²⁷, D-Arg²⁸, Har₂₉]hGH-RH(1-29)NH₂ Peptide 102

[CH₃(CH₂)₆CO-Tyr¹, D-Arg², Phe(pCl)⁶, Ala⁸, Amp⁹, Tyr(Et)¹⁰, His¹¹, Orn¹², Abu¹⁵, His²⁰, Orn²¹, Nle²⁷, D-Arg²⁸, Har²⁹]hGH-RH(1-29)NH₂ Peptide 103

[CH₃(CH₂)₆CO-Tyr¹, D-Arg², Phe(pCl)⁶, Ala⁸, His⁹, Dip¹⁰, His¹¹, Orn¹², Abu¹⁵, His²⁰, Orn²¹, Nle²⁷, D-Arg²⁸, Har²⁹]hGH-RH(1-29)NH₂ Peptide 104

[CH₃(CH₂)₆CO-Tyr¹, D-Arg², Phe(pCl)⁶, Ala⁸, His⁹, Phe(pNO₂)¹⁰, His¹¹, Orn¹², Abu¹⁵, His²⁰, Orn²¹, Nle²⁷, D-Arg²⁸, Har²⁹]hGH-RH(1-29)NH₂ Peptide 105

[CH₃(CH₂)₆CO-Tyr¹, D-Arg², Phe(pCl)⁸, Ala⁸, His⁹, Tyr(Et)¹⁰, His¹¹, Orn¹², Abu¹⁵, His²⁰, Orn²¹, Nle²⁷, D-Arg²⁸, Har²⁹]hGH-RH(1-29)NHEt Peptide 106

[HOOC(CH₂)₁₂CO-Tyr¹, D-Arg², Phe(pCl)⁶, Ala⁸, Amp⁹, Tyr(Et)¹⁰, His¹¹, Orn¹², Abu¹⁵, His²⁰, Orn²¹, Nle²⁷, D-Arg²⁸, Har²⁹]hGH-RH(1-29)NH₂ Peptide 107

[HOOC(CH₂)₁₂CO-Tyr¹, D-Arg², Phe(pCl)⁶, Ala⁸, His⁹, Dip¹⁰, His¹¹, Orn¹², Abu¹⁵, His²⁰, Orn²¹, Nle²⁷, D-Arg²⁸, Har²⁹√hGH-RH(1-29)NH₂ Peptide 108

[HOOC(CH₂)₁₂CO-Tyr¹, D-Arg², Phe(pCl)⁶, Ala⁸, His⁹, Phe(pNO₂)¹⁰, His¹¹, Orn¹², Abu¹⁵, His²⁰, Orn²¹, Nle²⁷, D-Arg²⁸, Har²⁹]hGH-RH(1-29)NH₂ Peptide 109

[HOOC(CH₂)₁₂CO-Tyr¹, D-Arg², Phe(pCl)⁶, Ala⁸, His⁹, Tyr(Et)¹⁰, His¹¹, Orn¹², Abu¹⁵, His²⁰, Orn²¹, Nle²⁷, D-Arg²⁸, Har²⁹]hGH-RH(1-29)NHEt Peptide 110

[CH₃(CH₂)₆CO-Tyr¹, D-Arg², Phe(pCl)⁶, Ala⁸, Amp⁹, Dip¹⁰, His¹¹, Orn²¹, Nle²⁷, D-Arg²⁸, Har₂₉]hGH-RH(1-29)NH₂ Peptide 111

[CH₃(CH₂)₆CO-Tyr¹, D-Arg², Phe(pCl)⁶, Ala⁸, Amp⁹, Phe(pNO₂)¹⁰, His¹¹, Orn¹², Abut¹⁵, His²⁰, Orn²¹, Nle²⁷, D-Arg²⁸, Har²⁹]hGH-RH(1-29)NH₂ Peptide 112

[CH₃(CH₂)₆CO-Tyr¹, D-Arg², Phe(pCl)⁶, Ala⁸, Amp⁹, Tyr(Et)¹⁰, His¹¹, Orn¹², Abu¹², His²⁰, Orn²¹, Nle²⁷, D-Arg²⁸, Har²⁹]hGH-RH(1-29)NHEt Peptide 113

[CH₃(CH₂)₆CO-Tyr¹, D-Arg², Phe(pCl)⁶, Ala⁸, His⁹, Dip¹⁰, His¹¹, Orn²¹, Nle²⁷, D-Arg²⁸, Har²⁹]hGH-RH(1-29)NHEt Peptide 114

[CH₃(CH₂)₆CO-Tyr¹, D-Arg², Phe(pCl)⁶, Ala⁸, His⁹, Phe(pNO₂)¹⁰, His¹¹, Orn¹², Abu¹⁵, His²⁰, Orn²¹, Nle²⁷, D-Arg²⁸, Har²⁹]hGH-RH(1-29)NHEt Peptide 115

[HOOC(CH₂)₁₂CO-Tyr¹, D-Arg², Phe(pCl)⁶, Ala⁸, Amp⁹, Dip¹⁰, His¹¹, Orn¹², Abu¹⁵, His²⁰, Orn²¹, Nle²⁷, D-Arg²⁸, Har²⁹]hGH-RH(1-29)NH₂ Peptide 116

[HOOC(CH₂)₁₂CO-Tyr¹, D-Arg², Phe(pCl)⁶, Ala⁸, Amp⁹, Phe(pNO₂)¹⁰, His¹¹, Orn¹², Abu¹⁵, His²⁰, Orn²¹, Nle²⁷, D-Arg²⁸, Har²⁹]hGH-RH(1-29)NH₂ Peptide 117

[CH₃(CH₂)₆CO-Tyr¹, D-Arg², Phe(pCl)⁶, Ala⁸, Amp⁹, Dip¹⁰, His¹¹, Orn¹², Abu¹⁵, His²⁰Orn²¹, Nle²⁷, D-Arg²⁸, Har²⁹]hGH-RH(1-29)NHEt Peptide 118

[CH₃(CH₂)₆CO-Tyr¹, D-Arg², Phe(pCl)⁶, Ala⁸, Amp⁹, Phe(pNO₂)¹⁰, His¹¹, Orn¹², Abu¹⁵, His²⁰, Orn², Nle²⁷, D-Arg²⁸, Har²⁹]hGH-RH(1-29)NHEt Peptide 119

[HOOC(CH₂)₁₂CO-Tyr¹, D-Arg², Phe(pCl)⁶, Ala⁸, Amp⁹, Dip¹⁰, His¹¹, Orn¹², Abu¹⁵, His²⁰, Orn²¹, Nle²⁷, D-Arg²⁸, Har²⁹]hGH-RH(1-29)NHEt Peptide 120

[HOOC(CH₂)₁₂CO-Tyr¹, D-Arg², Phe(pCl)⁶, Ala⁸, Amp⁹, Phe(pNO₂)¹⁰, His¹¹, Orn¹² Abu¹⁵, His²⁰, Orn²¹, Nle²⁷, D-Arg²⁸, Har²⁹]hGH-RH(1-29)NHEt Peptide 121

Closely related peptides which do not fall under the foregoing generic structural fonmula include:

[CH₃(CH₂)₄CO-Tyr¹, D-Arg², Phe(pCl)⁶, Arg⁹, Abu¹⁵, Nle²⁷, D-Arg²⁸, Har²⁹]hGH-1-29)NH₂ Peptide 2

[HOOC(CH₂)₄CO-Tyr¹, D-Arg², Phe(pCl)⁶, Arg⁹, Abu¹⁵, Nle²⁷, D-Arg²⁸, ]hGH-RH(1-29)NH₂ Peptide 3

[CH₃(CH₂)₆CO-Tyr¹, D-Arg², Phe(pCl)⁶, Arg⁹, Abu¹⁵, Nle²⁷, D-Arg²⁸, Har²⁹]hGH-RH(1-29)NH₂ Peptide 4

[HOOC(CH₂)₆CO-Tyr¹, D-Arg², Phe(pCl)⁶, Arg⁹, Abu¹⁵, Nle²⁷, D-Arg²⁸, Har²⁹]hGH-RH(1-29)NH₂ Peptide 5

[CH₃(CH₂)₈CO-Tyr¹, D-Arg², Phe(pCl)⁶, Arg⁹, Abu¹⁵, Nle²⁷, D-Arg²⁸, Har²⁹]hGH-RH(1-29)NH₂ Peptide 6

[HOOC(CH₂)₈CO-Tyr¹, D-Arg², Phe(pCl)⁶, Arg⁹, Abu¹⁵, Nle²⁷, D-Arg²⁸, Har²⁹]hGH-RH(1-29)NH₂ Peptide 7

[CH₃(CH₂),₁₀CO-Tyr¹, D-Arg², Phe(pCl)⁶, Arg⁹, Abu²⁵, Nle²⁷D-Arg²⁸, Har²⁹]hGH-RH(1-29)NH₂ Peptide 8

[HOOC(CH₂)₁₀CO-Tyr¹, D-Arg², Phe(pCl)⁶, Arg⁹, Abu¹⁵, Nle²⁷, D-Arg²⁸, Har²⁹]hGH-RH(1-29)NH₂ Peptide 9

[CH₃(CH₂)¹²CO-Tyr¹, D-Arg², Phe(pCl)⁶, Arg⁹, Abu¹⁵, Nle²⁷, D-Arg²⁸, Har²⁹]hGH-RH(1-29)NH₂ Peptide 10

[HOOC(CH₂)₁₂CO-Tyr¹, D-Arg², Phe(pCl)⁶, Arg⁹, Abu¹⁵, Nle²⁷, D-Arg²⁸, Har²⁹]hGH-RH(1-29)NH₂ Peptide 11

[CH₃(CH₂)₁₄CO-Tyr¹, D-Arg², Phe(pCl)⁶, Arg⁹, Abu¹⁵, Nle²⁷, D-Arg²⁸, ]hGH-RH(1-29 )NH₂ Peptide 12

[HOOC(CH₂)₁₄CO-Tyr¹, D-Arg², Phe(pCl)⁶, Arg⁹, Abu¹⁵, Nle²⁷, D-Arg²⁸, Har²⁹]hGH-RH(1-29)NH₂ Peptide 13

[CH₃(CH₂)₆CO-Tyr¹, D-Arg², Phe(pCl)⁶, Arg⁹, Abu¹⁵, Nle²⁷, Har²⁸, D-Arg²⁹]hGH-RH(1-29)NH₂ Peptide 14

[PhAc-Tyr¹, D-Arg², Phe(pCl)⁶, Arg⁹, Abu¹⁵, Nle²⁷, Har²⁸, Arg₂₉]hGH-RH(1-29)NH₂ Peptide 15

[CH₃(CH₂)₁₄CO-Phe⁰, D-Arg², Phe(pCl)⁶, Arg⁹, Abu¹⁵, Nle²⁷, D-Arg²⁸, Har²⁹]hGH-RH(1-29)NH₂ Peptide 16

[CH₃(CH₂)₁₄COD-Phe⁰, D-Arg², Phe(pCl)⁶, Arg⁹, Abu¹⁵, Nle²⁷, D-Arg²⁸, Har²⁹]hGH-RH(1-29)NH₂ Peptide 17

[PhAc-Arg⁰, D-Arg², Phe(pCl)⁶, Arg⁹, Abu¹⁵, Nle²⁷, D-Arg²⁸, Har²⁹]hGH-RH(1-29)NH₂ Peptide 18

[PhAc-D-Arg⁰, D-Arg², Phe(pCl)⁶, Arg⁹, Abu¹⁵, Nle²⁷, D-Arg²⁸, Har²⁹]hGH-RH(1-29)NH₂ Peptide 19

[PhAcTyr¹, D-Arg², Phe(pCl)⁶, Cit⁸, Arg⁹, Abu¹⁵, Nle²⁷, D-Arg²⁸, Har²⁹]hGH-RH(1-29)NH₂ Peptide 21

[PhAc-Tyr¹, D-Arg², Phe(pCl)⁶, Cit⁸, Cit⁹, Abu¹⁵, Nle²⁷, D-Arg²⁸, Har²⁹]hGH-RH(1-29)NH₂ Peptide 22

[PhAc-Tyr¹, D-Arg², Phe(pCl)⁶, Cit⁸, Arg⁹, Abu¹⁰, Nle²⁷, Har²⁸, D-Arg²⁹]hGH-RH(1-29)NH₂ Peptide 23

[PhAc-Tyr¹, D-Arg², Phe(pCl)⁹, Cit⁸, Cit⁹, Abu¹⁵, Nle²⁷, Har, D-Arg²⁹]hGH-RH(1-29)NH₂ Peptide 24

[HOOC(CH₂)₁₂CO-Tyr¹, D-Arg², Phe(pCl)⁶, Cit⁸, Cit⁹, Abu¹⁵, Nle²⁷, D-Arg²⁸, Har²⁹]hGH-RH(1-29)NH₂ Peptide 25

[PhAc-Tyr¹, D-Arg², Phe(pCl)⁶, D-Ala⁸, Arg⁹, Abu¹⁵, Nle²⁷, D-Arg²⁸, Har²⁹]hGH-RH(1-29)NH₂ Peptide 26

[PhAc-Tyr$^1$, D-Arg$^2$, Phe(pCl)$^8$, Abu$^8$, Arg$^9$, Abu$^{15}$, Nle$^{27}$, D-Arg$^{29}$, Har$^{29}$]hGH-RH(1-29)NH$_2$ Peptide 27

[PhAc-Tyr$^1$, D-Arg$^2$, Phe(pCl)$^6$, Cit$^9$, Abu$^{15}$, Nle$^{27}$, Har$^{28}$, D-Arg$^{29}$]hGH-RH(1-29)NH$_2$ Peptide 28

[PhAc-Tyr$^1$, D-Arg$^2$, Phe(pCl)$^6$, Arg$^9$, Amp$^{10}$, Abu$^{15}$, Nle$^{27}$, D-Arg$^{28}$, Har$^{29}$]hGH-RH(1-29)NH$_2$ Peptide 30

[PhAc-Tyr$^1$, D-Arg$^2$, Phe(pCl)$^6$, Har$^9$, Amp$^{10}$, Abu$^{15}$, Nle$^{27}$, D-Arg$^{28}$, Har$^{29}$]hGH-RH(1-29)NH$_2$ Peptide 31

[PhAc-Tyr$^1$, D-Arg$^2$, Phe(pCl)$^6$, Arg$^9$, His$^{10}$, Abu$^{15}$, Nle$^{27}$, D-Arg$^{28}$, Har$^{29}$]hGH-RH(1-29)NH$_2$ Peptide 32

[PhAc-Tyr$^1$, D-Arg$^2$, Phe(pCl)$^6$, Arg$^9$, Cha$^{10}$, Abu$^{15}$, Nle$^{27}$, D-Arg$^{28}$, Har$^{29}$]hGH-RH(1-29)NH$_2$ Peptide 33

[PhAc-Tyr$^1$, D-Arg$^2$, Phe(pCl)$^6$, Har$^9$, Tpi$^{10}$, Abu$^{15}$, Nle$^{27}$, D-Arg$^{28}$, Har$^{29}$]hGH-RH(1-29)NH$^2$ Peptide 34

[PhAc-Tyr$^1$, D-Arg$^2$, Phe(pCl)$^6$, Har$^9$, 2Nal$^{10}$, Abu$^{15}$, Nle$^{27}$, D-Arg$^{28}$, Har$^{29}$]hGH-RH(1-29)NH$_2$ Peptide 35

[PhAc-Tyr$^1$, D-Arg$^2$, Phe(pCl)$^6$, Har$^9$, Dip$^{10}$, Abu$^{15}$, Nle$^{27}$, D-Arg$^{28}$, Har$^{29}$]hGH-RH(1-29)NH$_2$ Peptide 36

[PhAc-Tyr$^1$, D-Arg$^2$, Phe(pCl)$^6$, Har$^9$, Phe(pNH$_2$)$^{10}$, Abu$^{15}$, Nle$^{27}$, D-Arg$^{28}$, Har$^{29}$]hGH-RH(1-29)NH$_2$ Peptide 37

[PhAc-Tyr$^1$, D-Arg$^2$, Phe(pCl)$^6$, Har$^9$, Trp$^{10}$, Abu$^{11}$, Nle$^{27}$, D-Arg$^{28}$, Har$^{29}$]hGH-RH(1-29)NH$_2$ Peptide 38

[PhAc-Tyr$^1$, D-Arg$^2$, Phe(pCl)$^6$, Har$^9$, Phe(pNO$_2$)$^{10}$, Abu$^{15}$, Nle$^{27}$, D-Arg$^{28}$, Har$^{29}$]hGH-RH(1-29)NH$_2$ Peptide 39

[PhAc-Tyr$^1$, D-Arg$^2$, Phe(pCl)$^6$, Har$^9$, 3-Pal$^{10}$, Abu$^{15}$, Nle$^{27}$, D-Arg$^{28}$, Har$^{29}$]hGH-RH(1-29)NH$_2$ Peptide 40

[PhAc-Tyr$^1$, D-Arg$^2$, Phe(pCl)$^6$, Har$^9$, Tyr(Et)$^{10}$, Abu$^{15}$, Nle$^{27}$, D-Arg$^{28}$, Har$^{29}$]hGH-RH(1-29)NH$_2$ Peptide 41

[PhAc-His$^1$, D-Arg$^2$, Tyr$^6$, Har$^9$, Bpa$^{10}$, Abu$^{15}$, Nle$^{27}$, D-Arg$^5$, Har$^{29}$]hGH-RH(1-29)NH$_2$ Peptide 42

[PhAc-Tyr$^1$, D-Arg$^2$, Phe(pC)$^6$, Arg$^9$, Har$^{12}$, Abu$^{15}$, Nle$^{27}$, D-Arg$^{28}$, Har$^{29}$]hGH-RH(1-29)NH$_2$ Peptide 43

[Hca-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$]hGH-RH(1-29)NH$_2$ Peptide 45

[PhAc-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$]hGH-RH(1-29)NHEt Peptide 46

[Hca-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NHEt Peptide 47

[PhAc-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NHEt Peptide 48

[PhAc-Tyr$^1$, D-Arg$^2$, Phe(pCl)$^6$, Har$^9$, Tyr(Me)$^{10}$, Aib$^{15}$, Nle$^{27}$, D-Arg$^{28}$, Har$^{29}$]hGH-RH(1-29)NHEt Peptide 49

[PhAc-Tyr$^1$, D-Arg$^2$, Phe(pCl)$^6$, Har$^9$, Tyr(Me)$^{10}$, Orn$^{12}$, Abu$^{15}$, Nle$^{27}$, D-Arg$^{28}$, Har$^{29}$]$^{hGH-RH}$(1-29)NHEt Peptide 50

[Hca-Tyr$^1$, D-Arg$^2$, Phe(pCl)$^6$, Har$^9$, Tyr(Me)$^{10}$, Abu$^{15}$, Nle$^{27}$, D-Arg$^{28}$, Agm$^{29}$]hGH-RH(1-29) Peptide 51

[PhAc-Tyr$^1$, D-Arg$^2$, Phe(pCl)$^6$, Har$^9$, Tyr(Me)$^{10}$, Abu$^{15}$, Nle$^{27}$, D-Arg$^{28}$, Agm$^{29}$]hGH-RH(1-29) Peptide 52

[Hca-Tyr$^1$, D-Arg$^2$, Phe(pCl)$^6$, Har, Tyr(Me)$^{10}$, Abu$^{15}$, Nle$^{27}$, D-Arg$^{28}$, Har$^{29}$, Har$^{30}$]hGH-RH(1-30)NH$_2$ Peptide 53

[Dat-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, Har$^{30}$]hGH-RH(1-30)NH$_2$ Peptide 54

[Ipa-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, Har$^{30}$]hGH-RH)1-30)NH$_2$ Peptide 55

[Hca-Tyr$^1$, D-Arg$^2$, Phe(pCl)$^8$, Har$^9$, Tyr(Me)$^{10}$, Abu$^{15}$, Nle$^{27}$, D-Arg$^{28}$, Har$^{29}$, Har$^{30}$]hGH-RH(1-30)NHEt Peptide 56

Hca-Tyr$^1$, D-Arg$^2$, Phe(pCl)$^6$, Har$^9$, Tyr(Me)$^{10}$, Abu$^{15}$, Nle$^{27}$, D-Arg$^{28}$, D-Arg$^{29}$, Har$^{30}$]hGH-RH(1-30)NH$_2$ Peptide 57

[Hca-Tyr$^1$, D-Arg$^2$, Phe(pCl)$^6$, Har$^9$, Tyr(Me)$^{10}$, Abu$^{15}$, Nle$^{27}$, Arg$^{28}$, D-Arg$^{30}$]hGH-RH(1-30)NH$_2$ Peptide 58

[Hca-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, Agm$^{30}$]hGH-RH(1-30) Peptide 59

[PhAc-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, Agm$^{30}$]hGH-RH(1-30) Peptide 60

[PhAc-Tyr$^1$, D-Arg$^2$, Phe(pCl)$^6$, Har$^9$, Tyr(Me)$^{10}$, His$^{11}$, Abu$^{15}$, Nle$^{27}$, D-Arg$^{28}$, Har$^{29}$]hGH-RH(1-29)NH$_2$ Peptide 62

[PhAc-Tyr$^1$, D-Arg$^2$, Phe(pCl)$^6$, Har$^9$, Tyr(Me)$^{10}$, Har$^{11}$, Abu$^{15}$, Nle$^{27}$, D-Arg$^{28}$, Har$^{29}$]hGH-RH(1-29)NH$_2$ Peptide 63

[PhAc-Tyr$^1$, D-Arg$^2$, Phe(pCl)$^6$, Har$^9$, Tyr(Me)$^{10}$, Amp$^{11}$, Abu$^{15}$, Nle$^{27}$, D-Arg$^{28}$, Har$^{29}$]hGH-RH(1-29)NH$_2$ Peptide 64

[PhAc-Tyr$^1$, D-Arg$^2$, Phe(pCl)$^8$, Har$^9$, Tyr(Me)$^{10}$, Cit$^{11}$, Abu$^{15}$, Nle$^{27}$, D-Arg$^{28}$, Har$^{29}$]hGH-RH(1-29)NH$_2$ Peptide 65

[PhAc-Tyr$^1$, D-Arg$^2$, Phe(pCl)$^8$, Har$^9$, Tyr(Me)$^{10}$, Abu$^{15}$, His$^{20}$, Nle$^{27}$, D-Arg$^{28}$, Har$^{29}$]hGH-RH(1-29)NH$_2$ Peptide 84

[PhAc-Tyr$^1$, D-Arg$^2$, Phe(pCl)$^6$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ Peptide 85

[PhAc-Tyr$^1$, D-Arg$^2$, Phe(pCl)$^6$, Arg$^9$, Cit$^{15}$, Nle$^{27}$, D-Arg$^{28}$, Har$^{29}$]hGH-RH(1-29)NH$_2$ Peptide 90

It is noted that the amino acid residues from 30 through 44 of the native GH-RH molecule do not appear to be essential to activity; nor does their identity appear to be critical. Therefore, it appears that the addition of some or all of these further amino acid residues to the C-terminus of the hGH-RH(1-29) NH$_2$ and hGH-RH(1-30)NH$_2$ analogs of the present invention will not affect the efficacy of these analogs as GH-RH antagonists. If some or all of these amino acids were added to the C-terminus of the hGH-RH(1-29)NH$_2$ analogs, the added amino acid residues could be the same as residues 30 through 44 in the native hGH-RH sequence or reasonable equivalents.

Synthetic Methods.

The synthetic peptides are synthesized by a suitable method such as by exclusive solid phase techniques, by partial solid-phase techniques, by fragment condensation or by classical solution phase synthesis.

When the analogs of this invention are synthesized by solid-phase method, the C-terminus residue (here, A$^{29}$ or A$^{30}$) is appropriately linked (anchored) to an inert solid support (resin) while bearing protecting groups for its alpha amino group (and, where appropriate, for its side chain functional group). After completion of this step, the alpha amino protecting group is removed from the anchored amino acid residue and the next amino acid residue, A$^{28}$ or A$^{29}$ respectively, is added having its alpha amino group (as well as any appropriate side chain functional group) suitably protected, and so forth. The N-terminus protecting groups are removed after each residue is added, but the side chain protecting groups are not yet removed. After all the desired amino acids have been linked in the proper sequence, the peptide is cleaved from the support and freed from all side chain protecting group(s) under conditions that are minimally destructive towards residues in the sequence. This is be followed by a careful purification and scrupulous characterization of the synthetic product, so as to ensure that the desired structure is indeed the one obtained.

It is particularly preferred to protect the alpha amino function of the amino acids during the coupling step with an acid or base sensitive protecting group. Such protecting groups should have the properties-of being stable in the conditions of peptide linkage formation, while being readily removable without destruction of the growing peptide chain and without racemization of any of the chiral centers contained therein. Suitable alpha amino protecting groups are Boc and Fmoc.

Medical Applications.

The hGH-RH antagonist peptides, or salts of these peptides, may be formulated in pharmaceutical dosage forms containing effective amounts thereof and administered to humans or animals for therapeutic or diagnostic purposes. The peptides may be used to suppress GH levels and to treat conditions associated with excessive levels of GH, e.g., diabetic retinopathy and nephropathy, and acromegaly. Also provided are methods for treating these diseases by administration of a composition of the invention to an individual needing such treatment. The main uses of GH-RH antagonists are, however, in the field of cancer, for example human cancers of the lung, prostate, breast, ovary, endometrium, stomach, colon, pancreas, kidney, bone, and brain where the receptors for GH-RH, IG-I/IGF-II, or GH are present, and that depend on stimulation by growth factors such as GH-RH, IGF-I, IGF-II, GH, or VEGF.

DETAILED DESCRIPTION OF THE PREFERRED EMBODIMENTS

A. Abbreviations

The nomenclature used to define the peptides is that specified by the IUPAC-IUB Commission on Biochemical Nomenclature wherein, in accordance with conventional representation, the amino group at the N-terminus appears to the left and the carboxyl group at the C-terminus appears to the right The term "natural amino acid" as used herein means one of the common, naturally occurring L-amino acids found in naturally occurring proteins: Gly, Ala, Val, Leu, Ile, Ser, Thr, Lys, Arg, Asp, Asn, Glu, Gln, Cys, Met, Phe, Tyr, Pro, Trp and His. When the natural amino acid residue has isomeric forms, it is the L-form of the amino acid that is represented herein unless otherwise expressly indicated.

Non-coded amino acids, or amino acid analogues, are also incorporated into the GH-RH antagonists. ("Non-coded" amino acids are those amino acids which are not among the approximately 20 natural amino acids found in naturally occurring proteins.) When these non-coded amino acids, or amino acid analogues, have isomeric forms, it is the L-form of the amino acid that is represented unless otherwise expressly indicated.

Abbreviations used herein are:
Abu alpha-aminobutyric acid
Ac acetyl
AcOH acetic acid
$Ac_2O$ acetic anhydride
Agm agmatine
Aib alpha-aminoisobutyric acid
All allyl
Alloc allyloxycarbonyl
Amp para-amidino-phenylalanine
Bpa para-benzoyl-phenylalanine
Boc tert-butyloxycarbonyl
Bom benzyloxymethyl
2BrZ 2-bromo-benzyloxycarbonyl
Bzl benzyl
Cha cyclohexylalanine
Chg cyclohexylglycine
cHx cyclohexyl
Cit citrulline (2-amino-5-ureidovaleric acid)
2ClZ 2chloro-benzyloxycarbonyl
Dat des-amino-tyrosine
DCM dichloromethane
DIC N,N'-dilsopropylcarbodiimide
DIEA diisopropylethylamine
Dip (3,3-diphenyl)alanine
DMF dimethylformamide
Et ethyl
Fm fluorenylmethyl
Fmoc fluorenylmethoxycarbonyt
For formyl
GH growth hormone
GH-RH GH releasing hormone
Gup paraguanidino-phenylalanine
Har homoarginine
HBTU 2-(1H-Benzotriazol-1-yl)-1,1,3,3-tetramethyluronium hexaflourophosphate
Hca hydrocinnamoyl
Hca-OH hydrocinnamic acid
hGH-RH human GH-RH
HOBt 1-hydroxybenzotriazole
HPLC high performance liquid chromatography
Ibu isobutyryl
IndAc indole-3-acetyl
Ipa indole-3propionyl
MBHA para-methylbenzhydrylamine
Me methyl
MeOH methanol
MeCN acetonitrile
Nac naphthylacetyl
Nal naphthylalanine
Nle norleucine
NMM N-methylmorpholine
Npr naphthylpropionyl
Orn ornithine
Pal pyridylalanine
PAM phenylacetamidomethyl
Ph phenyl
PhAc phenylacetyl
PhAc-OH phenylacetic acid
Phe(pCl) para-chloro-phenylalanine
Phe(pNH$_2$) para-amino-phenylalanine
Phe(pNO$_2$) para-nitro-phenylalanine
rGH-RH rat GH-RH
RP-HPLC reversed phase HPLC
SPA para-sulfonyl-phenoxyacetyl
TFA trifluoroacetic acid
Tos para-toluenesulfonyl
Tpi 1,2,3,4tetrahydronorharman-3-carboxylic acid
Tyr(Me) O-methyl-tyrosine
Tyr(Et) O-ethyl-tyrosine
Z benzyloxycarbonyl B. The GH-RH Analogs The hGH-RH analogs of the present invention were designed to increase the antagonistic effects at the pituitary level, and/or at the tumoral level. Some of these analogs, such as Peptide 4, Peptide 7, Peptide 21, Peptide 30, Peptide 31, Peptide 37, Peptide 41, Peptide 42, Peptide 62, Peptide 67, and Peptide 69 possess high endocrine antagonistic potencies, causing a very effective and long lasting inhibition of the GH release stimulated by hGH-RH(1-29)NH$_2$ in vitro and in vivo, and exhibit high binding affinities to the pituitary GH-RH receptors. Some analogs, such as Peptide 4, Peptide 5, Peptide 7, Peptide II, Peptide 22, Peptide 35, Peptide 36, Peptide 39, Peptide 41, Peptide 62, Peptide 67, Peptide 69, Peptide 70, Peptide 72, Peptide 76, Peptide 77, Peptide 79, Peptide 80, Peptide 86, Peptide 95, Peptide 96, and Peptide 97, show elevated tumor inhibitory potencies and display extremely high binding affinities to the tumoral receptors for GH-RH. The peptides of the present invention were also designed to improve their chemical and metabolic stabilities.

The following embodiments are specially preferred as having remarkable bioactivity:

[$CH_3(CH_2)_4CO$-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 2

[$CH_3(CH_2)_6CO$-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 4

[$HOOC(CH_2)_6CO$-Tyr$^1$, D-Arg$^2$, Phe(pCl)$^6$, Arg$^9$, Abu$^{11}$, Nle$^{27}$, D-Arg$^{28}$, Har$^{29}$]hGH-RH(1-29)NH$_2$ Peptide 5

[$CH_3(CH_2)_8CO$-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 6

[$HOOC(CH_2)_8CO$-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 7

[$HOOC(CH_2)_{12}CO$-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 11

[$CH_3(CH_2)_6CO$-Tyr$^1$, D-Arg$^2$, Phe(pCl)$^6$, Arg$^9$, Abu$^{15}$, Nle$^{27}$, Har$^{28}$, D-Arg$^{29}$]hGH-RH(1-29)NH$_2$ Peptide 14

[PhAc-Tyr$^1$, D-Arg$^2$, Phe(pCl)$_6$, Arg$^9$, Abu$^{15}$, Nle$^{27}$, Har$^{28}$, D-Arg$^{29}$]hGH-RH(1-29)NH$_2$ Peptide 15

[PhAc-Tyr$^1$, D-Arg$^2$, Phe(pCl)$^6$, Cit$^8$, Arg$^9$, Abu$^{15}$, Nle$^{27}$, D-Arg$^{28}$, Har$^{29}$]hGH-RH(1-29)NH$_2$ Peptide 21

[PhAc-Tyr$^1$, D-Arg$^2$, Phe(pCl)$^6$, Cit$^8$, Cit$^9$, Abu$^{15}$, Nle$^{27}$, D-Arg$^{28}$, Har$^{29}$]hGH-RH(1-29)NH$_2$ Peptide 22

[PhAc-Tyr$^1$, D-Arg$^2$, Phe(pCl)$^6$, Abu$^8$, Arg$^9$, Abu$^{15}$, Nle$^{27}$, D-Arg$^{28}$, Har$^{29}$]hGH-RH(1-29)NH$_2$ Peptide 27

[PhAc-Tyr$^1$, Arg$^2$, Phe(pCl)$^6$, Cit$^9$, Abu$^{15}$, Nle$^2$, Har$^{28}$, D-Arg$^{29}$]hGH-RH(1-29)NH$_2$ Peptide 28

[PhAc-Tyr$^1$, D-Arg$^2$, Phe(pCl)$^6$, Arg$^9$, Amp$^{10}$, Abu$^{15}$, Nle$^{27}$, D-Arg$^{28}$, Har$^{29}$]hGH-RH(1-29)NH$_2$ Peptide 30

[PhAc-Tyr$^1$, D-Arg$^2$, Phe(pCl)$^6$, Har$^9$, Amp$^{10}$, Abu$^{15}$, Nle$^{27}$, D-Arg$^{28}$, Har$^{29}$]hGH-RH(1-29)NH$_2$ Peptide 31

[PhAc-Tyr$^1$, D-Arg$^2$, Phe(pCl)$^6$, Har$^9$, 2-Nal$^{10}$, Abu$^{15}$, Nle$^{27}$, D-Arg$^{28}$, Har$^{29}$]hGH-RH(1-29)NH$_2$ Peptide 35

[PhAc-Tyr$^1$, D-Arg$^2$, Phe(pCl)$^6$, Har$^9$, Dip$^{10}$, Abu$^{15}$, Nle-$^{27}$, D-Arg$^{28}$, Har$^{29}$]hGH-RH(1-29)NH$_2$ Peptide 36

[PhAc-Tyr$^1$, D-Arg$^2$, Phe(pCl)$^8$, Har$^9$, Phe(pNH$_2$)$^{10}$, Abu$^{15}$, Nle$^{27}$, D-Arg$^{28}$, Har$^{20}$]hGH-RH(1-29)NH$_2$ Peptide 37

[PhAc-Tyr$^1$, D-Arg$^2$, Phe(pCl)$^6$, Har$^9$, Phe(pNO$_2$)$^{10}$, Abu$^{15}$, Nle$^{27}$, D-Arg$^{28}$, Har$^{29}$]hGH-RH(1-29)NH$_2$ Peptide 39

[PhAc-Tyr$^1$, D-Arg$^2$, Phe(pCl)$^6$, Har$^9$, Tyr(Et)$^{10}$, Abu$^{15}$, Nle$^{27}$, D-Arg$^{28}$, Har$^{29}$]hGH-RH(1-29)NH$_2$ Peptide 41

[PhAc-His$^1$, D-Arg$^2$, Tyr$^8$, Har$^9$, Bpa$^{10}$, Abu$^{15}$, Nle$^{27}$, D-Arg$^{28}$, Har$^{29}$]hGH-RH(1-29)NH$_2$ Peptide 42

[PhAc-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$]hGH-RH(1-29)NHEt Peptide 46

[PhAc-Tyr$^1$, D-Arg$^2$, Phe(pCl)$^6$, Har$^9$, Tyr(Me)$^{10}$, His$^{11}$, Abu$^{15}$, Nle$^{27}$, D-Arg$^{28}$, Har$^{29}$]hGH-RH(1-29)NH$_2$ Peptide 62

[PhAc-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 67

[Phc-Tyr$^1$, D-Arg$^2$, Phe(pCl)$^6$, Amp$^9$, Abu$^{15}$, Nle$^{27}$, D-Arg$^{28}$, Har$^{29}$]hGH-RH(1-29)NH$_2$ Peptide 68

[PhAc-Tyr$^1$, D-Arg$^2$, Phe(pCl)$^6$, His$^9$, Tyr(Me)$^{10}$, Abu$^{15}$, Nle$^{27}$, D-Arg$^{28}$, Har$^{29}$]hGH-RH(1-29)NH$_2$ Peptide 69

[$CH_3(CH_2)_6CO$-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 70

[$HOOC(CH_2)_8CO$Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 71

[$HOOC(CH_2)_{12}CO$-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 72

[PhAc-Tyr$^1$, D-Arg$^2$, Phe(pCl)$^6$, Amp$^9$, Tyr(Me)$^{10}$, His$^{11}$, Abu$_{15}$, Nle$^{27}$, D-Arg$^{28}$, Har$^{29}$]hGH-RH(1-29)NH$_2$ Peptide 73

[PhAc-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$^{29}$]hGH-RH(1-29)NH$_2$ Peptide 74

[1-Nac-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$^{29}$]hGH-RH(1-29)NH$_2$ Peptide 75

[$CH_3(CH_2)_6CO$-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$_{29}$]hGH-RH(1-29)NH$_2$ Peptide 76

[$HOOC(CH_2)_{12}CO$-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$_{29}$]hGH-RH(1-29)NH$_2$ Peptide 77

[$CH_3(CH_2)_6CO$-Tyr$^{1, Arg2}$, Phe(pCl)$^6$, Cit$^8$, Amp$^9$, Tyr(Et)$^{10}$, His$^{11}$, Abu$^{15}$, Nle$^{27}$, D-Arg$^{28}$Har$^{29}$]hGH-RH(1-29)NH$_2$ Peptide 78

[$CH_3(CH_2)_6CO$-Tyr$^1$, D-Arg$^2$, Phe(pCl)$^6$, Cit$^8$, His$^9$, Tyr(Et)$^{10}$, His$^{11}$, Abu$^{15}$, Nle$^{27}$, D-Arg$^{28}$, Har$_{29}$]hGH-RH(1-29)NH$_2$ Peptide 79

[$CH_3(CH_2)_8CO$-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$_{29}$]hGH-RH(1-29)NH$_2$ Peptide 80

[$HOOC(CH_2)CO$-Tyr$^1$, D-Arg$^2$, Phe(pCl)$^6$, Ala$^8$, His$^9$, Tyr(Et)$^{10}$, His$^{11}$, Abu$^{15}$; Nle$^{27}$, D-Arg$^{28}$Har$^{29}$]hGH-RH(1-29)NH$_2$ Peptide 81

[$HOOC(CH_2)_{12}CO$.-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$_{29}$]hGH-RH(1-29)NH$_2$ Peptide 82

[PhAc-Tyr$^1$, D-Arg$^2$, Phe(pCl)$^5$, Har$^9$, Tyr(Me)$^{10}$, Abu$^{15}$, His$^{20}$, Nle$^{27}$, D-Arg$^{28}$Har$^{29}$]NH$_2$ Peptide 84

[PhAc-Tyr$^1$, D-Arg$^2$, Phe(pCl)$^6$, Har$^9$, Tyr(Me)$^{10}$, His$^{11}$, Abu$^{15}$, His$^{20}$, Nle$^{27}$D-Arg$^{28}$, Har$^{29}$]hGH-RH(1-29)NH$_2$ Peptide 85

[$CH_3(CH_2)_6CO$-Tyr$^1$, D-Arg$^2$, Phe(pCl)$^5$, Ala$^8$, His$^9$, Tyr(Et)$^{10}$, His$^{11}$, Abu$^{15}$, His$^{20}$, Nle$^{29}$, D-Arg$^{28}$, Har$_{29}$]hGH-RH(1-29)NH$_2$ Peptide 86

[$CH_3(CH_2)_6CO$-Tyr$^1$, D-Arg$^2$, Phe(pCl)$^6$, Ala$^8$, Amp$^9$, Tyr(Et)$^{10}$, His$^{11}$, Abu$^{15}$, His$^{20}$, Nle$^{29}$, D-Arg$^{28}$, Har$_{29}$]hGH-RH(1-29)NH$_2$ Peptide 87

[$HOOC(CH_2)_{12}CO$-Tyr$^1$, D-Arg$^2$, Phe(pCl)$^6$, Ala$^8$, His$^9$, Tyr(Et)$^{10}$, His$^{11}$, Abu$^{15}$, His$^{20}$, Nle$^{27}$, D-Arg$^{28}$, Har$_{29}$]hGH-RH(1-29)NH$_2$ Peptide 88

[$HOOC(CH_2)_{12}CO$-Tyr$^1$, D-Arg$^2$, Phe(pCl)$^6$, Ala$^8$, Amp$^9$, Tyr(Et)$^{10}$, His$^{11}$, Abu$^{15}$, His$^{20}$, Nle$^{27}$, D-Arg$^{28}$, Har$_{29}$]hGH-RH(1-29)NH$_2$ Peptide 89

[PhAc-Tyr$^1$, D-Arg$^2$, Phe(pCl)$^6$, Arg$^9$, Cit$^{15}$, Nle$^{27}$, D-Arg$^{28}$, Har$^{29}$]hGH-RH(1-29)NH$_2$ Peptide 90

[1-Nac-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NH$_2$ Peptide 91

[$CH_3(CH_2)_6CO$-Tyr$^1$, D-Arg$^2$, Phe(pCl)$^6$, His$^9$, Tyr(Et)$^{10}$, His$^{11}$, Abu$^{15}$, Nle$^{27}$, D-Arg$^{28}$Har$^{29}$]RH(1-29)NH$_2$ Peptide 92

[$CH_3(CH_2)_6CO$-Tyr$^1$, D-Arg$^2$, Phe(pCl)$^6$, Ala$^8$, His$^9$, Cit$^{15}$, Nle$^{27}$, D-Arg$^{28}$, Har$^{29}$]hGH-RH(1-29)NH$_2$ Peptide 93

[$CH_3(CH_2)_8CO$-Tyr$^1$, D-Arg$^2$, Phe(pCl)$^6$, Ala$^8$, His$^9$, Tyr(Et)$^{10}$, His$^{11}$, His$^{15}$, His$^{20}$, Nle$^{27}$, D-Arg$^{28}$, Har$^{29}$]hGH-RH(1-29)NH$_2$ Peptide 94

[$CH_3(CH_2)_6CO$-Tyr$^1$, D-Arg$^2$, Phe(pCl)$^6$, Ala$^8$, His$^9$, Tyr(Et)$^{10}$, His$^{11}$, Orn$^{12}$, Abu$^{15}$, Orn$^{21}$, Ble$^{27}$, D-Arg$^{28}$, Har$_{29}$]hGH-RH(1-29)NH$_2$ Peptde 95

[$CH_3(CH_2)_6CO$-Tyr$^1$, D-Arg$^2$, Phe(pCl)$^6$, Ala$^8$, His$^9$, Tyr(Et)$^{10}$, His$^{11}$, Orn$^{12}$, Abu$^{15}$, His$^{20}$, Orn$^{231}$, Nle$^{27}$, D-Arg$^{28}$, Har$^{29}$]hGH-RH(1-29)NH$_2$ Peptide 96

[$CH_3(CH_2)_6CO$-Tyr$^1$, D-Arg$^2$, Phe(pCl)$^6$, Ala$^8$, His$^9$, Tyr(Et)$^{10}$, His$^{11}$, Nle$^{27}$, D-Arg$^{28}$, Har$^{29}$]hGH-RH(1-29)NHEt Peptide 97

[CH$_3$(CH$_2$)$_8$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NHEt Peptide 98

[CH$_3$(CH$_2$)$_{10}$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NHEt Peptide 99

[Hca -Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NHEt Peptide 100

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NHMe Peptide 101

[HOOC(CH$_2$)$_{12}$CO-Tyr$^1$, D-Arg$^2$, Phe(pCl)$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 102

[CH$_3$(CH$_2$)$_6$CO-Tyr$^1$, D-Arg$^2$, Phe(pCl)$^6$, Ala$^8$, Amp$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har-$^{29}$]hGH-RH(1-29)NH$_2$ Peptide 103

[CH$_3$(CH$_2$)$_6$CO-Tyr$^1$, D-Arg$^2$, Phe(pCl)$^6$, Ala$^8$, His$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$] hGH-RH(1-29)NH$_2$ Peptide 104

[CH$_3$(CH$_2$)$_6$CO-Tyr$^1$, D-Arg$^2$, Phe(pCl)$^6$, Ala$^8$, His$^9$, Phe(pNO$_2$)$^{10}$, His$^{11}$, Orn$^{21}$, Nle$^{27}$, D-Arg$^{28}$, Har$^{29}$]hGH-RH(1-29)NH$_2$ Peptide 105

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Orn$^{21}$, Nle$^{27}$, D-Arg$^{28}$, Har$^{29}$]hGH-RH(1-29)NHEt Peptide 106

[HOOC(CH$_2$)$_{12}$CO-Tyr$^1$, D-Arg$^2$, Phe(pCl)$^6$, Ala$^8$, Amp$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 107

[HOOC(CH$_2$)$_{12}$CO-Tyr$^1$, D-Arg$^2$, Phe(pCl)$^6$, Ala$^8$, His$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 108

[HOOC(CH$_2$)$_{12}$CO-Tyr$^1$, D-Arg$^2$, Phe(pCl)$^6$, Ala$^8$, His$^9$, Phe(pNO$_2$)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 109

[HOOC(CH$_2$)$_{12}$CO-Tyr$^1$, D-Arg$^2$, Phe(pCl)$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, Arg$^{28}$, Har$^{29}$]hGH-RH(1-29)NHEt Peptide 110

[CH$_3$(CH$_2$)$_6$CO-Tyr$^1$, D-Arg$^2$, Phe(pCl)$^6$, Ala$^6$, Amp$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 111

[CH$_3$(CH$_2$)$_6$CO-Tyr$^1$, D-Arg$^2$, Phe(pCl)$^6$, Ala$^8$, Amp$^9$, Phe(pNO$_2$)$^{10}$, His$^{11}$, Orn$^{12}$, Abu$^{15}$, Orn$^{21}$, Nle$^{27}$, D-Arg$^{28}$, Har$^{29}$]hGH-RH(1-29)NH$_2$ Peptide 112

[CH$_3$(CH$_2$)$_6$CO-Tyr$^1$, D-Arg$^2$, Phe(pCl)$^6$, Ala$^8$, Amp$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 113

[CH$_3$(CH$_2$)$_6$CO-Tyr$^1$, D-Arg$^2$, Phe(pCl)$^6$, Ala$^8$, His$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$] hGH-RH(1-29)NHEt Peptide 114

[CH$_3$(CH$_2$)$_6$CO-Tyr$^1$, D-Arg$^2$, Phe(pCl)$^6$, Ala$^8$, His$^9$, Phe(pNO$_2$)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 115

[HOOC(CH$_2$)$_{12}$CO-Tyr$^1$, D-Arg$^2$, Phe(pCl)$^6$, Ala$^8$, Amp$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 116

[HOOC(CH$_2$)$_{12}$CO-Tyr$^1$, D-Arg$^2$, Phe(pCl)$^6$, Ala$^8$, Amp$^9$, Phe(pNO$_2$)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 117

[CH$_3$(CH$_2$)$_6$CO-Tyr$^1$, D-Arg$^2$, Phe(pCl)$^6$, Ala$^8$, Amp$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 118

[CH$_3$(CH$_2$)$_6$CO-Tyr$^1$, D-Arg$^2$, Phe(pCl)$^6$, Ala$^8$, Amp$^9$, Phe(pNO$_2$)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 119

[HOOC(CH$_2$)$_{12}$CO-Tyr$^1$, D-Arg$^2$, Phe(pCl)$^6$, Ala$^8$, Amp$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 120

[HOOC(CH$_2$)$_{12}$CO-Tyr$^1$, D-Arg$^2$, Phe(pCl)$^6$, Ala$^8$, Amp$^9$, Phe(pNO$_2$)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 121

Thirty, very preferred embodiments have the formulae:

CH$_3$(CH$_2$)$_6$CO-Tyr$^1$-D-Asp-Ala-Ile$^5$-Phe(pCl)$^6$-Thr$^7$-Asn$^8$-Arg$_9$-Tyr$^{10}$-Arg$^{11}$-Lys$^{12}$-Val$^{13}$-Leu$^{14}$-Abu$^{15}$-Gln$^{16}$-Leu$^{17}$-Ser$_{18}$-Ala$^{19}$-Arg$^{20}$-Lys$^{21}$-Leu$^{22}$Leu$^{23}$-Gln$^{24}$Asp$^{25}$Ile$^{26}$-Nle$^{27}$-D-Arg$^{28}$-Har$^{29}$-NH$_2$ Peptide 4

HOOC(CH$_2$)$_6$CO-Tyr$^1$-D-Arg$^2$-Asp$^3$-Ala$^4$-Ile$^5$-Phe(pCl)$^6$-Thr$_7$-Asn$^8$-Arg$^9$-Tyr$^{10}$-Arg$^{11}$-Lys$^{12}$-Val$^{13}$-Leu$^{14}$-Abu$^{15}$-Gln$_{16}$-Leu$^{17}$-Ser$^{18}$-Ala$^{19}$-Arg$^{20}$-Lys$^{21}$-Leu$^{22}$-Leu$^{22}$-Gln$^{24}$-Asp$^{25}$Ile$^{26}$-Nle$^{27}$-D-Arg$^{28}$-Har$^{29}$-NH$_2$ Peptide 5

HOOC(CH$_2$)$_8$CO-Tyr$^1$-D-Arg$^2$-Asp$^3$-Ala$^4$-Ile$^5$-Phe(pCl)$^6$-Thr$_7$-Asn$^8$-Arg$^9$-Tyr$^{10}$-Arg$^{11}$-Lys$^{12}$-Val$^{13}$-Leu$^{14}$-Abu$^{15}$-Gln$_{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 7

HOOC(CH$_2$)$_{12}$CO-Tyr$^1$-D-Arg$^2$-Asp$^3$-Ala$^4$-Ile$^5$-Phe(pCl)$^6$-Thr$^7$-Asn$^8$-Arg$^9$-Tyr$^{10}$-Arg$^{11}$-Lys$^{12}$-Val$^{13}$-Leu$^{14}$-Abu$^{15}$-Gln$_{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 11

PhAc-Tyr$_1$-D-Arg$^2$-Asp$^3$-Ala$^4$-Ile$^5$-Phe(pCl)$^6$-Thr$^7$-Cit$^8$-Arg$_9$-Tyr$^{10}$-Arg$^{11}$-Lys$^{12}$-Val$^{13}$-Leu$^{14}$-Abu$^{15}$-Gln$^{16}$-Leu$_{17}$Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 21

PhAc-Tyr$_1$-D-Arg$^2$-Asp$^3$-Ala$^4$-Ile$^5$-Phe(pCl)$^6$-Thr$^7$-Cit$^8$-Cit$_9$-Tyr$^{10}$-Arg$^{11}$-Lys$^{12}$-Val$^{13}$-Leu$^{14}$-Abu$^{15}$-Gln$^{16}$-Leu$^{17}$-Ser$_{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 22

PhAc-Ty$_9^1$-D-Arg$^2$-Asp$^3$-Ala$^4$-Ile$^5$-Phe(pCl)$^6$-Thr$^7$-Asn$^8$-Arg -Amp$^{10}$-Arg$^{11}$-Lys$^{12}$-Val$^{13}$-Leu$^{14}$-Abu$^{15}$-Gln$^{15}$-Leu$^{17}$-Ser$^{18}$-Ala$^{19}$-Arg$^{20}$-Lys$^{21}$ -Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 30

PhAc-Tyr$_1$-D-Arg$^2$-Asp$^3$-Ala$^4$-Ile$^5$-Phe(pCl)$^6$-Thr$^7$-Asn$^8$-Har$_9$-Amp$^{10}$-Arg$^{11}$-Lys$^{12}$-Val$^{14}$-Leu$^{14}$-Abu$^{15}$-Gln$_{16}$Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Ar$^{29}$-NH$_2$ Peptide 31

PhAc-Tyr$_1$-D-Arg$^2$-Asp$^3$-Ala$^4$-Ile$^5$-Phe(pCl)$^6$-Thr$^7$-Asn$^8$-Har$_8$-2-Nal$^{10}$-Arg$^{11}$-Lys$^{12}$-Val$^{14}$-Leu$^{14}$-Abu$^{15}$-Gln$^{16}$-Leu$_{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-D-Arg$^{28}$-Har$^{29}$-NH$_2$ Peptide-35

PhAc-Tyr$^1$-D-Arg$^2$-Asp$^3$-Ala$^4$-Ile$^5$-Phe(pCl)$^6$-Thr$^7$-Asn$^8$-Har$^9$-Dip$^{10}$-Arg$^{11}$-Lys$^{12}$-Val$^{13}$-Leu$^{14}$-Abu$^{15}$-Gln$^{16}$-Leu$_{17}$-Ser$^{18}$-Ala$^{19}$ -Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NhPeptide 36

PhAc-Tyr$_9^1$-D-Arg$^2$-Asp$^3$-Ala$^4$-Ile$^5$-Phe(pCl)$^6$-Thr$^7$-Asn$^8$-Har -Phe(pNH$_2$)$^{10}$-Arg$^{11}$-Lys$^{12}$-Val$^{13}$-Leu$^{14}$-Abu$^{15}$-Gln$^{16}$-Leu$^{17}$-Ser$^{18}$-Ala$^{19}$-Arg$^{20}$-Lys$^{21}$-Leu$^{22}$-Leu$^{23}$ -Gln$_{24}$-Asp$^{25}$-Ile$^{26}$-Nle$^{27}$-D-Arg$^{28}$-Har$^{29}$-NH$_2$ Peptide 37

PhAc-Tyr$_1$-D-Arg$^2$-Asp$^3$-Ala$^4$-Ile$^5$-Phe(pCl)$^6$-Thr$^7$-Asn$^8$-Har$_9$-Phe(pNO$_2$)$^{10}$-Arg$^{11}$-Lys$^{12}$-Val$^{13}$-Leu$^{14}$-Abu$^{15}$-Gln$_{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 39

PhAc-Tyr$_1$-D-Arg$^2$-Asp$^3$-Ala$^4$-Ile$^5$-Phe(pCl)$^6$-Thr$^7$-Asn$^8$-Har$_9$-Tyr(Et)$^{10}$-Arg$^{11}$-Lys$^{12}$-Val$^{13}$-Leu$^{14}$-Abu$^{15}$-Gln$_{16}$Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 41

PhAc-His$_{10}^1$-D-Arg$^2$-Asp$^3$-Ala$^4$-Ile$^5$-Tyr$^6$-Thr$^7$-Asn$^8$-Har$^9$-Bpa -Arg$^{11}$-Lys$^{12}$-Val$^{13}$-Leu$^{14}$-Abu$^{15}$-Gln$^{16}$-Leu$^{17}$-Ser$^{18}$-Ala$^{19}$-Arg$^{20}$-Lys$^{21}$ -Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 42

PhAc-Tyr$^1$-D-Arg$^2$-Asp$^3$ -Ala$^4$-Ile$^5$-Phe(pCl)$^6$-Thr$^7$-Asn$^8$-Har$^9$-Tyr(Me)$^{10}$-Arg$^{11}$-Lys$^{12}$-Val$^{13}$-Leu$^{14}$-Abu$^{15}$-Gln$^{16}$-

Leu$^{17}$-Ser$^{18}$-Ala$^{19}$-Agr$^{20}$-Lys$^{21}$-Leu$^{22}$-Leu$^{23}$-Gln$^{24}$-Asp$^{25}$-Ile$^{26}$-Nle$^{27}$D-Arg$^{28}$-Har$^{29}$-NHEt Peptide 46

PhAc-Tyr$_1$-D-Arg$^2$-Asp$^3$-Ala$^4$-Ile$^5$-Phe(pCl)$^8$-Thr$^7$-Asn$^8$-Har$^9$-Tyr(Me)$^{10}$-His$^{11}$-Lys$^{12}$-Val$^{13}$-Leu$^{14}$-Abu$^{15}$-Gln$^{16}$-Leu$_{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$D-Arg$^{28}$-Har$^{29}$-NH$_2$ Peptide 62

PhAc-Tyr$_1$-D-Arg$^2$-Asp$^3$-Ala$^4$-Ile$^5$-Phe(pCl)$^6$-Thr$^7$-Asn$^8$-Amp$^9$-Tyr(Me)$^{10}$-Arg$^{11}$-Lys$^{12}$-Val$^{13}$-Leu$^{14}$-Abu$^{15}$-Gln$^{16}$-Leu$_{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{25}$Ile$^{26}$-Nle$^{27}$-D-Arg$^{28}$-Har$^{29}$-NH$_2$ Peptide 67

PhAc-Tyr$_1$-D-Arg$^2$-Asp$^3$-Ala$^4$-Ile$^5$-Phe(pCl)$^6$-Thr$^7$-Asn$^8$-His$^9$-Tyr(Me)$^{10}$-Arg$^{11}$-Lys$^{12}$-Val$^{23}$-Leu$^{14}$-Abu$^{15}$-Gln$^{16}$-Leu$_{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{26}$-D-Arg$^{28}$-Har$^{29}$-NH$_2$ Peptide 69

CH$_3$(CH$_2$)$_6$CO-Tyr$^1$-D-Arg$^2$-Asp$^3$-Ala$^4$-Ile$^5$-Phe(pCl)$^6$-Thr$^7$-Asn$^8$-Amp$^9$-Tyr(Me)$^{10}$-Arg$^{11}$-Lys$^{12}$-Val$^{13}$-Leu$^{14}$-Abu$_{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 70

HOOC(CH$_2$)$_{12}$CO-Tyr$^1$-D-Arg$^2$-Asp$^3$-Ala$^4$-Ile$^5$-Phe(pCl)$^6$-Thr$^7$-Asn$^8$-Amp$^9$-Tyr(Me)$^{10}$-Arg$^{11}$-Lys$^{12}$-Val$^{13}$-Leu$^{14}$-Abu$_{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 72

CH$_3$(CH$_2$)$_6$CO-Tyr$^1$-D-Arg$^2$-Asp$^3$-Ala$^4$-Ile$^5$-Phe(Cl)$^6$-Thr$^7$-Cit$_8$-Amp$^9$-Tyr(Me)$^{10}$-His$^{11}$-Lys$^{12}$-Val$^{13}$-Leu$^{14}$-Abu$^{15}$-Gln$_{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 76

HOOC(CH$_2$)$_{12}$CO-Tyr$^1$-D-Arg$^2$-Asp$^3$-Ala$^4$-Ile$^5$-Phe(pCl)$^6$-Thr$^7$-Cit$^8$-Amp$^9$-Tyr(Me)$^{10}$-His$^{11}$-Lys$^{12}$-Val$^{13}$-Leu$^{14}$-Abu$_{15}$-Gln$^{16}$-Leu$^{17}$-Ser$^{16}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 77

CH$_3$(CH$_2$)$_6$CO-Tyr$^1$-D-Arg$^2$-Asp$^3$-Ala$^4$-Ile$^5$-Phe(pCl)$^5$-Thr$_6$-Cit$^8$-His$^9$-Tyr(Et)$^{10}$-His$^{11}$-Lys$^{12}$-Val$^{13}$-Leu$^{14}$-Abu$_{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 79

CH$_3$(CH$_2$)$_6$CO-Tyr$^1$-D-Arg$^2$-Asp$^3$-Ala$^4$-Ile$^5$-Phe(pCl)$^6$-Thr$^7$-Cit$^8$-His$^9$-Tyr(Et)$^{10}$-His$^{11}$-Lys$^{12}$-Val$^{13}$-Leu$^{14}$-Abu$_{15}$-Gln$^{16}$-Leu$^{17}$-Ser$^{18}$-Ala$^{19}$-ARg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 80

HOOC(CH$_2$)$_{12}$CO-Tyr$^1$-D-Arg$^2$-Asp$^3$-Ala$^4$-Ile$^5$-Phe(pCl)$^6$-Thr$^7$-Ala$^8$-His$^9$-Tyr(Et)$^{10}$-His$^{11}$-Lys$^{12}$-Val$^{13}$-Leu$^{14}$-Abu$_{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 82

CH$_3$(CH$_2$)$_6$-CO-Tyr$^1$-D-Arg$^2$-Asp$^3$-Ala$^4$-Ile$^5$-Phe(pCl)$^6$-Thr$^7$-Ala$^8$-His$^9$-Tyr(Et)$^{10}$-His$^{11}$-Lys$^{12}$-Val$^{13}$-Leu$^{14}$-Abu$_{15}$-Gln$^{16}$-Leu$^{17}$-Ser$^{18}$-Ala$^{19}$-His$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 86

CH$_3$(CH$_2$)$_6$CO-Tyr$^1$-D-Arg$^2$-Asp$^3$-Ala$^4$-Ile$^5$-Phe(pCl)$^6$-Thr$^7$-Asn$^8$-His$^9$-Tyr(Et)$^{10}$-His$^{11}$-Lys$^{12}$-Val$^{13}$-Leu$^{14}$Abu$^{15}$-Gln$^{16}$-Leu$^{17}$-Ser$^{18}$-Ala$^{19}$-Arg$^{20}$-Lys$^{21}$-Leu$_{22}$-Leu$^{23}$-Gln$^{24}$-Asp$^{25}$-Ile$^{26}$-Nle$^{27}$-D-Arg$^{28}$-Har$^{29}$NH$_2$ Peptide 92

CH$_3$(CH$_2$)$_6$CO-Tyr$^1$-D-Arg$^2$-Asp$^3$-Ala$^4$-Ile$^5$-Phe(pCl)$^6$-Thr$^7$-Ala$^8$-His$^9$-Tyr(Et)$^{10}$-His$^{11}$-Orn$^{12}$-Va;$^{13}$-Leu$^{14}$-Abu$_{15}$-Gln$^{16}$-Leu$^{17}$-Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-D-Arg$^{28}$-Har$^{29}$-NH$_2$ Peptide 95

CH$_3$(CH$_2$)$_6$CO-Tyr$^1$-D-Arg$^2$-Asp$^3$-Ala$^4$-Ile$^5$-Phe(pCl)$^6$-Thr$^7$-Ala$^8$-His$^9$-Tyr(Et)$^{10}$-His$^{11}$-Orn$^{12}$-Val$^{13}$-Leu$^{14}$-Abu$_{15}$-Gln$^{16}$-Leu$^{17}$-Ser$^{18}$-Ala$^{19}$-His$^{20}$-Orn$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 96

CH$_3$(CH$_2$)$_6$CO-Tyr$^1$-D-Arg$^2$-Asp$^3$-Ala$^4$-His$^5$-Phe(pCl)$^6$-Thr$^7$-Ala$^8$-His$^9$-Tyr(Et)$^{10}$-His$^{11}$-Lys$^{12}$-Val$^{13}$-Leu$^{14}$-Abu$^{15}$-Gln$^{18}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NHEt Peptide 97

Under well-established convention, these may be abbreviated as follows:

[CH$_3$(CH$_2$)$_6$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 4

[HOOC(CH$_2$)$_6$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 5

[HOOC(CH$_2$)$_6$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 7

[HOOC(CH$_2$)$_{12}$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 11

[PhAc-Tyr$^1$, D-Arg$^2$, Phe(pCl)$^6$, Cit$^8$, Arg$^9$, Abu$^{15}$, Nle$^{27}$, D-Arg$^{28}$, Har$^{29}$]hGH-RH(1-29)NH$_2$ Peptide 21

[PhAc-Tyr$^1$, D-Arg$^2$, Phe(pCl)$^6$, Cit$^8$, Cit$^9$, Abu$^{15}$, Nle$^{27}$, D-Arg$^{28}$, Har$^{29}$]hGH-RH(1-29)NH$_2$ Peptide 22

[PhAc-Tyr$^1$, D-Arg$^2$, Phe(pCl)$^6$, Arg$^9$, Amp$^{10}$, Abu$^{15}$, Nle$^{27}$, D-Arg$^{28}$, Har$^{29}$]hGH-RH(1-29)NH$_2$ Peptide 30

[PhAc-Tyr$^1$, D-Arg$^2$, Phe(pCl)$^6$, Har$^9$, Amp$^{10}$, Abu$^{15}$, Nle$^{27}$, D-Arg$^{28}$, Har$^{29}$]hGH-RH(1-29)NH$_2$ Peptide 31

[PhAc-Tyr$^1$, D-Arg$^2$, Phe(pCl)$^6$, Har$^9$, 2-Nal$^{10}$, Abu$^{15}$, Nle$^{27}$, D-Arg$^{28}$, Har$^{29}$]hGH-RH(1-29)NH$_2$ Peptide 35

[PhAc-Tyr$^1$, D-Arg$^2$, Phe(pCl)$^6$, Har$^9$, Dip$^{10}$, Abu$^{15}$, Nle$^{27}$, D-Arg$^{28}$, Har$^{29}$]hGH-RH(1-29)NH$_2$ Peptide 36

[PhAc-Tyr$^1$, D-Arg$^2$, Phe(pCl)$^6$, Har$^9$, Phe(pNH$_2$)$^{10}$, Abu$^{15}$, Nle$^{27}$, D-Arg$^{28}$, Har$^{29}$]hGH-RH(1-29)NH$_2$ Peptide 37

[PhAc-Tyr$^1$, D-Arg$^2$, Phe(pCl)$^6$, Har$^9$, Phe(pNO$_2$)$^{10}$, Abu$^{15}$, Nle$^{27}$, D-Arg$^{28}$, Har$^{29}$]hGH-RH(1-29)NH$_2$ Peptide 39

[PhAc-Tyr$^1$, D-Arg$^2$, Phe(pCl)$^6$, Har$^9$, Tyr(Et)$^{10}$, Abu$^{15}$, Nle$^{27}$, D-Arg$^{28}$, Har$^{29}$]hGH-RH(1-29)NH$_2$ Peptide 41

[PhAc-His$^1$, D-Arg$^2$, Tyr$^6$, Har$^9$, Bpa$^{10}$, $^{Abu15}$, Nle$^{27}$, D-Arg$^{28}$, Har$^{29}$]hGH-RH(1-29)NH$_2$ Peptide 42

[PhAc-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$]hGH-RH(1-29)NH$_2$ Peptide 46

[PhAc-Tyr$^1$, D-Arg$^2$, Phe(pCl)$^6$, Har$^9$, Tyr(Me)$^{10}$, His$^{11}$, Abu$^{15}$, Nle$^{27}$, D-Arg$^{28}$, Har$^{29}$]hGH-RH(1-29)NH$_2$ Peptide 62

[PhAc-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 67

[PhAc-Tyr$^1$, D-Arg$^2$, Phe(pCl)$^6$, His$^9$, Tyr(Me)$^{10}$, Abu$^{15}$, Nle$^{27}$, D-Arg$^{28}$, Har$^{29}$]hGH-RH(1-29)NH$_2$ Peptide 69

[CH$_3$(CH$_2$)$_6$CO-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 70

[HOOC(CH$_2$)$_{12}$CO-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 72

[CH$_3$(CH$_2$)$_6$CO-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$_{29}$]hGH-RH(1-29)NH$_2$ Peptide 76

[HOOC(CH$_2$)$_{12}$CO-Tyr$^1$, D-Arg$^2$, Phe(pCl)$^8$, Cit$^8$, Amp$^9$, Tyr(Me)$^{10}$, His$^{11}$, Abu$^{15}$, Nle$^{27}$, D-Arg$^{28}$, Har$_{29}$]hGH-RH(1-29)NH$_2$ Peptide 77

[CH$_3$(CH$_2$)$_6$CO-Tyr$^1$, D-Arg$^2$, Phe(pCl)$^6$, Cit$^8$, His$^9$, Tyr(Et)$^{10}$, His$^{11}$, Abu$^{15}$, Nle$^{27}$, D-Arg$^{28}$, Har$_{29}$]hGH-RH(1-29)NH$_2$ Peptide 79

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$_{29}$]hGH-RH(1-29)NH$_2$ Peptide 80

[HOOC(CH$_2$)$_{12}$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$_{29}$]hGH-RH(1-29)NH$_2$ Peptide 82

[CH₃(CH₂)₆CO-Tyr¹, D-Arg², Phe(pCl)⁶, Ala⁸, His⁹, Tyr(Et)¹⁰, His¹¹, Abu¹⁵, His²⁰, Nle²⁷, D-Arg²⁸, Har²⁹]hGH-RH(1-29)NH₂ Peptide 86

[CH₃(CH₂)₆CO-Tyr¹, D-Arg², Phe(pCl)⁶, His⁹, Tyr(Et)¹⁰, His¹¹, Abu¹⁵, Nle²⁷, D-Arg²⁸, Har²⁹]hGH-RH(1-29)NH₂ Peptide 92

[CH₃(CH₂)₆CO-Tyr¹, D-Arg², Phe(pCl)⁶, Ala⁸, His⁹, Tyr(Et)¹⁰, His¹¹, Orn¹², Abu¹⁵, Orn²¹, Nle²⁷, D-Arg²⁸, Har²⁹]hGH-RH(1-29)NH₂ Peptide 95

[CH₃(CH₂)₆CO-Tyr¹, D-Arg², Phe(pCl)⁶, Ala⁸, His⁹, Tyr(Et)¹⁰, His¹¹, Orn¹², Abu¹⁵, His²⁰, Nle²⁷, D-Arg²⁸, Har²⁹]hGH-RH(1-29)NH₂ Peptide 96

[CH₃(CH₂)₆CO-Tyr¹, D-Arg², Phe(pCl)⁶, Ala⁸, His⁹, Tyr(Et)¹⁰, His¹¹, Abu¹⁵, Nle²⁷, D-Arg²⁸, Har²⁹]hGH-RH(1-29)NHEt Peptide 97

C. Method of Preparation

1. Overview of Synthesis

The peptides are synthesized by suitable methods such as by exclusive solid phase techniques, by partial solid-phase techniques, by fragment condensation or by classical solution phase synthesis. For example, the techniques of exclusive solid-phase synthesis are set forth in the textbook "Solid Phase Peptide Synthesis", J. M. Stewart and J. D. Young, Pierce Chem. Company, Rockford, Ill., 1984 (2nd. ed.), and M. Bodanszky, "Principles of Peptide Synthesis", Springer Verlag, 1984. The hGH-RH antagonist peptides are preferably prepared using solid phase synthesis, such as that generally described by Merrifield, J.Am.Chem.Soc., 85 p. 2149 (1963), although other equivalent chemical syntheses known in the art can also be used as previously mentioned.

The synthesis is carried out with amino acids that are protected at their alpha amino group. Urethane type protecting groups (Boc or Fmoc) are preferably used for the protection of the alpha amino group.

In solid phase synthesis, the N-alpha-protected amino acid moiety which forms the aminoacyl group of the final peptide at the C-terminus is attached to a polymeric resin support via a chemical link. After completion of the coupling reaction, the alpha amino protecting group is selectively removed to allow subsequent coupling reactions to take place at the amino-terminus, preferably with 50% TFA in DCM when the N-alpha-protecting group is Boc, or by 20% piperidine in DMF when the N-alpha-protecting group is Fmoc. The remaining amino acids with similarly Boc or Fmoc-protected alpha amino groups are coupled stepwise to the free amino group of the preceding amino acid on the resin to obtain the desired peptide sequence. Because the amino acid residues are coupled to the alpha amino group of the C-terminus residue, growth of the synthetic hGH-RH analogue peptides begins at the C terminus and progresses toward the N-terminus. When the desired sequence has been obtained, the peptide is acylated at the N-terminus, and it is removed from the support polymer.

Each protected amino acid is used in excess (2.5 or 3 equivalents) and the coupling reactions are usually carried out in DCM, DMF or mixtures thereof. The extent of completion of the coupling reaction is monitored at each stage by the ninhydrin reaction. In cases where incomplete coupling is determined, the coupling procedure is repeated, or a capping by acetylation of unreacted amino groups is carried out, before removal of the alpha amino protecting group prior to the coupling of the next amino acid.

Typical synthesis cycles are shown in Table I and Table II.

TABLE I

Protocol for a Typical Synthetic Cycle Using Boc-strategy

| Step | Reagent | Mixing Time (min) |
|---|---|---|
| 1. Deprotection | 50% TFA in DCM | 5 + 25 |
| | DCM wash | 1 |
| | 2-propanol wash | 1 |
| 2. Neutralization | 5% DIEA in DCM | 1 |
| | DCM wash | 1 |
| | MeOH wash | 1 |
| | 5% DIEA in DCM | 3 |
| | MeOH wash | 1 |
| | DCM wash (3 times) | 1 |
| 3. Coupling | 3 eq. Boc-amino acid in DCM or DMF + 3 eq. DIC or the preformed HOBt ester of the Boc-amino acid | 60 |
| | MeOH wash (3 times) | 1 |
| | DCM wash (3 times) | 1 |
| 4. Acetylation (if appropriate) | Ac₂O in pyridine (30%) | 10 + 20 |
| | MeOH wash (3 times) | 1 |
| | DCM wash (3 times) | 1 |

TABLE II

Protocol for a Typical Synthetic Cycle Using Fmoc-strategy

| Step | Reagent | Mixing Time (min) |
|---|---|---|
| 1. Deprotection | 20% piperidine in DMF | 5 + 15 |
| | DMF wash (3 times) | 1 |
| 2. Coupling | 3 eq. Fmoc-amino acid in DMF + 3 eq. DIC or + 3 eq. HBTU + 3 eq. HOBt + 6 eq. DIEA | 60 |
| | DMF wash (3 times) | 1 |
| 3. Acetylation (if appropriate) | 3 eq. 1-acetylimidazole in DMF | 30 |
| | DMF wash (3 times) | 1 |

After completion of the synthesis, the cleavage of the peptide from the resin can be effected using procedures well known in peptide chemistry.

2. Choice of the Support Polymer

The hGH-RH antagonist peptides may be synthesized on a variety of support polymers, i.e. MBHA, Merrifield, PAM, Rink amide or Wang resins. The peptides can also be synthesized on aminomethyl, MBHA, or other resins that have been previously derivatized with suitable linkers. Examples of such linkers are the base-labile 4-hydroxymethyl benzoic acid (HMBA) linker for the attachment of C-terminal carboxyl groups or the acid-labile para-sulfonyl-phenoxyacetyl (SPA) linker which permits the attachment of agmatine through its guanidino group.

When peptides with an amidated C-terminus are synthesized by using Boc strategy, the preferred resin is MBHA. Attachment of the C-terminal amino acid to this resin can be accomplished by the standard DIC-mediated coupling method described in Table I.

In order to prepare peptides with a C-terminal ethylamide (-NHEt) modification, the Merrifield resin or HMBA-MBHA resin can be used in conjunction with the Boc strategy. Loading of the C-terminal amino acid onto the Merrifield resin is done by coupling mediated by potassium fluoride (KF) or cesium salt at elevated temperature.

For the synthesis of pepudes having Agm at the C-terminus, it is preferred that the support phase is MBHA resin or an aminomethyl resin. The guanidino group of Boc-Agm is joined to the support polymer through a stable, but readily cleavable linker such as the para-sulfonyl-phenoxyacetyl (SPA) moiety. The alpha-amino-Boc-protected Agm is reacted with the chlorosulfonyl phenoxyacetic acid Cl—$SO_2$—$C_6H_4$—O—$CH_2$—COOH to form Boc-Agm-$SO_2$—$C_6H_4$—O—$CH_2$—COOH. This compound is then coupled to the support polymer e.g. to MBHA resin using DIC or HBTU-HOBt-DIEA as activating reagent to yield Boc-Agm-SPA-MBHA 3. Amino Acid Derivatives Used Bifunctional amino acids, i.e. those not having side chain functional groups, are mostly used in the form of their N-alpha Boc- or Fmoc-derivatives for synthesis. Thus, Boc-Gly-OH or Fmoc-Gly-OH is typically used for incorporating the Gly residue. The naturally occurring bifunctional amino acids are Gly, Ala, Val, Leu, Ile, Phe, and Pro, and some well-known non-coded bifunctional amino acids used in this invention are Abu, Aib, and Nle.

Some of the amino acid residues of the peptides have side chain functional groups which are reactive with reagents used in coupling or deprotection. When such side chain groups are present, suitable protecting groups are joined to these functional groups to prevent undesirable chemical reactions occurring during the reactions used to form the pepbdes. The following general rules are followed in selecting a particular side chain protecting group: (a) the protecting group preferably retains its protecting properties and is not split off under coupling conditions, (b) the protecting group should be stable under conditions for removing the alpha amino protecting group at each step of the synthesis, (c) the side chain protecting group must be removable upon the completion of the synthesis of the desired amino acid sequence, under reaction conditions that will not undesirably alter the peptide chain.

When Boc-amino acids are used in the synthesis, the reactive side chain functional groups can be protected as follows: Tos or nitro ($NO_2$) for Arg and Har, cHx or Fm for Asp and Glu; Bom for His; 2ClZ or Fmoc for Lys and Orn; Bzl for Ser and Thr; For for Trp; and 2BrZ for Tyr. The side chains of Asn and Gln are unprotected. In the case of Fmoc synthesis, the reactive side chain functional groups can be protected by other appropriate protective groups as follows: 2,2,4,6,7-pentamethyl-dihydrobenzofurane-5-sulfonyl (Pbf) or bis-Boc for Arg and Har; tert-butyl (tBu) for Asp and Glu; no protective group or trityl (Trt) protection for Asn and Gin; Trt for His; Boc or 4-methoxytrityl (Mmt) for Lys and Orn; tBu or Trt for Ser and Thr; Boc for Trp; and tBu or 2-chlorotrityl (2ClTrt) for Tyr.

In addition to the widely known coded and non-coded amino acids mentioned above, some of the peptides of this application contain less common norncoded amino acids such as para-amidino-phenylalanine (Amp); para-guanidino-phenylalanine (Gup); cyclohexylalanine (Cha); 1,2,3,4tetrahydronorharman-3-carboxylic acid (Tpi); (2-naphthyl)alanine (2-Nal); (3,3-diphenyl)alanine (Dip); para-amino-phenylalanine [Phe(pNH$_2$)]; para-nitro-phenylalanine [Phe(pNO$_2$)]; (3pyridyl)alanine (3-Pal); O-ethyl-tyrosine [Tyr(Et)]; and para-benzoyl-phenylalanine (Bpa). These amino acid residues are incorporated into the peptides by coupling the suitable protected amino acid derivatives. A non-exclusive list of such protected amino acid derivatives that can be used is as follows: Boc-Amp(Alloc)-OH, Boc-Amp-OH, Fmoc-Amp(Alloc)-OH, Fmoc-Amp-OH, Boc-Gup(Tos)-OH, Boc-Gup-OH, Fmoc-Gup(Boc)$_2$-OH, Fmoc-Gup-OH, Boc-Cha-OH, Boc-Tpi-OH, Boc-2-Nal-OH, Boc-Dip-OH, Boc-Phe(pNH-Z)-OH, Boc-Phe(pNO$_2$)—OH, Boc-3-Pal-OH, Boc-Tyr(Et)-OH, and Boc-Bpa-OH. The protected derivatives of noncoded amino acids mentioned above are commonly available from several commercial suppliers, including Bachem (King of Prussia, Pa.), Peptides International (Louisville, Ky.), Novabiochem (San Diego, Calif.), Advanced ChemTech (Louisville, Ky.), and RSP Amino Acid Analogues DBA (Worcester, Mass.).

4. Stepwise Coupling of Amino Acid Residues

Utilizing the above mentioned support polymers and after loading of the C-terminal amino acid or Agm residue, the peptide itself may suitably be built up by solid phase synthesis in the conventional manner. Each protected amino acid is coupled in about a three-fold molar excess, with respect to resin-bound free amino residues, and the coupling may be carried out in a medium such as DMF-DCM (1:1) or in DMF or DCM alone. The selection of an appropriate coupling reagent is within the skill of the arL Particularly suitable as coupling reagents are N,N'-diisopropyl carbodiimide (DIC), or HBTU combined with HOBt in the presence of DIEA. The success of the coupling reaction at each stage of the synthesis is preferably monitored by the ninhydrin reaction. In cases where incomplete coupling occurs, either the coupling procedure is repeated, or the resin-bound unreacted amino residues are acetylated using a capping reagent, before removal of the alpha amino protecting group. Suitable capping reagents are 1-acetylimidazole and Ac$_2$O-pyridine.

Final acylation of the N-terminus of the peptide with monocarboxylic acids is done in the same way as the previous couplings, with the difference that the appropriate carboxylic acid is used instead of an amino acid. When dicarboxylic acids are attached to the N-terminus and it is desired that only one —COOH group reacts with the amino terminus of the peptide (that is, monoamides of these acids are prepared), the anhydrides of the respective dicarboxylic acids can be used for coupling. The cyclic anhydrides of many dicarboxylic acids are commercially available; in other cases the preformed anhydrides of these acids are prepared by treatment with DIC and used for coupling.

5. Cleavage of the Peptide from the Support Polymer and Removal of the Side-Chain Protecting Groups When the synthesis is complete, the peptide is cleaved from the support phase and its side-chain protecting groups are removed.

In cases where peptides with an amidated C-terminus (—CONH$_2$) or with a C-terminal carboxyl group (—COOH) are prepared by Boc strategy on an MBHA, Merrifield, or PAM resin, the removal of the peptide from the resin is performed by treatment with a reagent such as liquid hydrogen fluoride (HF). This is also the case for peptides synthesized on the Boc-Agm-SPA-MBHA resin. In some instances, the liquid HF also cleaves all the remaining side chain protecting groups. However, if side chain protecting groups resistant to HF treatment are present on the peptide, additional cleavage steps should be performed in order to remove these protecting groups. Thus, Fm and Fmoc protecting groups are removed by treatment with 20% piperidine in DMF, while All and Alloc groups are removed by treatment with Pd(PPh$_3$)$_4$ catalyst and nucleophilic scavengers, prior to or after the HF treatment.

Suitably, the dried and protected peptide-resin is treated with a mixture consisting of 1.0 mL m-cresol and 10 mL anhydrous hydrogen fluoride per gram of peptide-resin for 60-120 min at 0° C. to cleave the peptide from the resin as well as to remove the HF-labile side chain protecting groups. After the removal of the hydrogen fluoride under a stream of nitrogen and vacuum, the free peptides are precipitated with ether, filtered, washed with ether and ethyl acetate, extracted with 50% acetic acid, and lyophilized.

In cases where peptides with an ethylamide (-NHEt) C-terminus are prepared by Boc strategy on the Merrifield or HMBA-MBHA resin, the protected peptides are first cleaved from the resin by ethylamine ($EtNH_2$) mediated aminolysis. Suitably, liquid $EtNH_2$ is transferred into a cooled, heavy-walled glass flask that contains the dried and protected peptide-resin. The quantity of liquid $EtNH_2$ should be sufficient to cover the peptide-resin. The flask is stoppered, and shaken with the liquid $EtNH_2$ for 3.5 hours at room temperature in order to allow for the reaction to take place. After this, the flask is cooled in a dry ice bath, opened, and the liquid $EtNH_2$ is filtered off the solid residue that contains a mixture of resin and cleaved peptide, the peptide still having the protecting groups attached. The solid residue is dried and subjected to HF treatment as described above, in order to remove the side chain protecting groups of the peptide.

6. Purification

The purification of the crude peptides can be effected using procedures well known in peptide chemistry. For example, purification may be performed on a MacRabbit HPLC system (Rainin Instrument Co. Inc., Wobum, Mass,) with a Knauer UV Photometer and a Kipp and Zonen BD40 Recorder using a Vydac218TP510 reversed-phase column (10×250 mm, packed with C18 silica gel, 300 Å pore size, 5 µm particle size) (The Separations Group Inc., Hesperia, Calif.). The column is eluted with a solvent system consisting of (A) 0.1% aqueous TFA and (B) 0.1% TFA in 70% aqueous MeCN in a linear gradient mode (e.g., 30-55% B in 120 min). The eluent is monitored at 220 nm, and fractions are examined by analytical HPLC using a Hewlett-Packard Model HP-1090 liquid chromatograph and pooled to give maximum purity. Analytical HPLC is carried out on a Vydac 218TP52 reversed-phase column (2×250 mm, C18, 300 Å, 5 µm) using isocratic elution with a solvent system consisting of (A) and (B) defined above. The peaks are monitored at 220 and 280 nm. The peptides are judged to be substantially (>95%) pure by analytical HPLC. Molecular masses are checked by electrospray mass spectrometry, and the expected amino acid compositions are confirmed by amino acid analysis.

D. Pharmaceutical Compositions and Mode of Administration

The peptides of the invention may be administered in the form of pharmaceutically acceptable, nontoxic salts, such as acid addition salts. Illustrative of such acid addition salts are hydrochloride, hydrobromide, sulphate, phosphate, fumarate, gluconate, tannate, maleate, acetate, trifluoroacetate, citrate, benzoate, succinate, alginate, pamoate, malate, ascorbate, tartarate, and the like. Particularly preferred antagonists are salts of low solubility, e.g., pamoate salts and the like. These exhibit long duration of activity.

The compounds of the present invention are suitably administered to subject humans or animals subcutaneously (s.c.), intramuscularly (i.m.), or intravenously (i.v); intranasally or by pulmonary inhalation; by transdermal delivery; or in a depot form (e.g., microcapsules, microgranules, or cylindrical rod like implants) formulated from a biodegradable suitable polymer (such as D,L-lactide-coglycolide), the former two depot modes being preferred. Other equivalent modes of administration are also within the scope of this invention, i.e., continuous drip, cutaneous patches, depot injecbons, infusion pump and time release modes such as microcapsules and the like. Administration is in any physiologically acceptable injectable carrier, physiological saline being acceptable, though other carriers known to the art may also be used.

The peptides are preferably administered parenterally, intramuscularly, subcutaneously or intravenously with a pharmaceutically acceptable carrier such as isotonic saline. Alternatively, the peptides may be administered as an intranasal spray with an appropriate carrier or by pulmonary inhalation. One suitable route of administration is a depot form formulated from a biodegradable suitable polymer, e.g., poly-D,L-lactide-coglycolide as microcapsules, microgranules or cylindrical implants containing dispersed antagonistic compounds.

The amount of peptide needed depends on the type of pharmaceutical composition and on the mode of administration. In cases where human subjects receive solutions of GH-RH antagonists, administered by i.m. or s.c. injection, or in the form of intranasal spray or pulmonary inhalation, the typical doses are between 2-20 mg/day/patient, given once a day or divided into 2-4 administrations/day. When the GH-RH antagonists are administered intravenously to human patients, typical doses are in the range of 8-80 µg/kg of body weight/day, divided into 1-4 bolus injections/day or given as a continuous infusion. When depot preparations of the GH-RH antagonists are used, e.g by i.m. injection of pamoate salts or other salts of low solubility, or by i.m. or s.c. administration of microcapsules, microgranules, or implants containing the antagonistic compounds dispersed in a biodegradable polymer, the typical doses, are between 1-10 mg antagonist/day/patient.

E. Therapeutic Uses of GH-RH Antagonists

The most important therapeutic applications of GH-RH antagonists are expected to be in the field of oncology and endocrinology. Some of the GH-RH antagonists act predominantly at the pituitary level and have stronger endocrine effects, inhibiting the GH-RH-evoked GH release, and ultimately decreasing the serum levels of GH and IGF-I. Other GH-RH antagonists act predominantly at the tumor level, by blocking the tumoral receptors for GH-RH, reducing the production of various autocrlnelparacrine tumor growth factors (such as IGF-I, IGF-II, GH, VEGF, FGF) and/or downregulating their receptors, and thus exert stronger inhibitory effects on tumor growth. These antagonists can also be used as carrier systems linked to radionuclides for tumor localization or therapy, or conjugated to chemotherapeutic agents or toxins. Such hybrid compounds can be actively targeted to cancer for diagnostic or therapeutic purposes. Yet other GH-RH antagonists act by multiple mechanisms of action, that is by endocrine mechanisms and by direct effects on tumors at the same time. Thus, the main therapeutic indications of various GH-RH antagonists differ based on their preferential mechanism of action.

Analogs of GH-RH with antagonistic action on the pituitary can be used in situations where it is beneficial to suppress serum levels of GH and IGF-I. Thus they are indicated for the therapy of en idocrine disorders characterized by excessive production of GH and IGF-I, as well as for the treatment of cancers that express receptors for IGF-I, IGF-II, or GH, and the proliferation of which is stimulated by these growth factors.

Somatostatin analogs and GH antagonists are also available for the treatment of endocrine conditions caused by GH and IGF-I. However, GH-RH antagonists offer unique therapeutical benefits unobtainable by the use of somatostatin analogs and GH antagonists. These benefits are due to the multiple mechanisms of action of GH-RH antagonists, namely that they exert GH- and IGF-I-independent direct effects on tumors and other target sites, in addition to inhibiting the endocrine axis for GH and IGF-I. GH-RH antagonists may be given alone or together with somatostatin analogs, a combination which more completely suppresses GH and IGF-I levels. An undesired side-effect of GH antagonists, which can be avoided by the administration of GH-RH antagonists, is the elevation of serum GH levels through a feed-back mechanism.

One disease caused by excess growth hormone is acromegaly, which is manifested in an abnormal enlargement of the bones of the face and extremities. GH-RH antagonists could alleviate the clinical manifestations of acromegaly, e.g. the enlargement of facial and extremity bones, the enlargement of heart, and other structural and functional abnormalities of the cardiovascular system. The GH-RH antagonists may also be used to treat diabetic retinopathy (the main cause of blindness in diabetics) and diabetic nephropathy, in which damage to the eye and kidney respectively is thought to be due to GH. Diabetic patients can also benefit from the increased insulin sensitivity produced by GH-RH antagonists, an effect linked to the ability of these compounds to reduce the GH and IGF-I levels. In addition, since they inhibit GH release, GH-RH antagonists can be used to slow down the progression of muscular dystrophy.

Drugs with anti-growth factor properties such as GH-RH antagonists can also be of benefit in controlling or slowing down the progression of some clinicopathologic processes in conditions such as idiopathic pulmonary fibrosis, systemic sclerosis and hypertrophic cardiomyopathy, where the present medical therapies have relatively little to offer. In addition, no drug therapy has been shown to be effective in decreasing the incidence of restenosis after percutaneous transluminal coronary angioplasty (PTCA) and new approaches must be devised, including the use of GH-RH antagonists. Some gynecologic conditions, such as myoma, endometriosis, and polycystic ovary syndrome, can also be treated with GH-RH antagonists in combination with luteinizing hormone-releasing hormone (LH-RH) agonists or antagonists. GH-RH antagonists are also available for treatment of benign prostatic hyperplasia (BPH), and hyperplastc and benign proliferative disorders of other normal organs in which the GH-RH receptors are present.

However, the main applications of GH-RH antagonists are in the field of cancer. GH-RH antagonists, especially those with strong direct effects at the tumor level, are indicated for the inhibition of growth of primary tumors and for the suppression of their metastatic spread. Since the antiproliferative effects of GH-RH antagonists are exerted by several mechanisms, these compounds are available for the treatment of a large variety of cancers, such as those that depend on autocrine/paracrine and endocrine stimulation by GH-RH, IGF-I, IGF-II, GH, VEGF, and FGF.

GH-RH antagonists are available for the treatment of tumors that express GH-RH receptors and use GH-RH as an autocrine/paracrine growth factor. Such malignancies include, but are not limited to, cancers of the lung, prostate, breast, ovary, endometrium, stomach, intestine, pancreas, kidney, bone, liver, as well as glioblastomas, pheochromocytomas, melanomas, and lymphomas. By blocking the tumoral receptors for GH-RH, these antagonists prevent the stimulatory action of GH-RH, resulting in inhibition of tumor growth.

One advantage of GH-RH antagonists over somatostatin analogs is based on the fact that GH-RH antagonists may be utilized for suppression of tumors which do not have somatostatin receptors but express the tumoral receptors for GH-RH, for example human osteogenic sarcomas.

Malignancies that express the IGF-I receptors, and depend on IGF-I and/or IGF-II as growth factors, are available for therapy with GH-RH antagonists. These malignancies include, among others, lung cancers, prostatic, breast lovarian, endometrial, gastric, colorectal, pancreatic, renal, and hepatic cancers, sarcomas, and brain tumors. The ability of GH-RH antagonists to decrease serum (GF-I levels, inhibit the autocrine/paracrine production of IGF-I and/or IGF-II in the tumor issue, and downregulate the expression level of IGF-I receptor, is beneficial for cancer therapy.

Breast cancers and other types of cancer that depend on GH as a growth factor, can be treated with GH-RH antagonists. The ability of GH-RH antagonists to reduce serum GH levels, inhibit the autocrine production of GH, and downregulate GH receptor expression, beneficiate the treatment of certain breast cancers and other types of tumors as well.

GH-RH antagonists are available as inhibitors of angiogenesis, in view of their inhibitory activity on the synthesis of VEGF by tumor tissues and normal endothelial cells, and considering their antiproliferative effect on endothelial cells. Thus GH-RH antagonists could be beneficial for the treatment of those tumors that strongly depend on VEGF and neoangiogenesis.

EXAMPLES

The present invention is described in connection with the following examples which are set forth for the purposes of illustration only. In the examples, optically active protected amino acids in the L-configuration are used except where specifically noted.

The following Examples set forth suitable methods of synthesizing the novel GH-RH antagonists by the solid-phase technique.

Example I $CH_3(CH_2)_6CO$-$Tyr^1$-D-$Arg_2$-$Asp_3$-$Ala^4$-$Ile^6$-$Phe(pCl)^6$-$Thr_7$-$Ala^8$-$His^9$-$Tyr(Et)^{10}$-$His^{11}$-$Lys^{12}$-$Val^{13}$-$Leu^{14}$-$Abu_{15}$-$Gln^{16}$-$Leu^{17}$-$Ser^{18}$-$Ala^{19}$-$Arg^{20}$-$Lys^{21}$-$Leu^{22}$-$Leu^{23}$-$Gln^{24}$-$Asp^{25}$-$Ile^{26}$-$Nle^{27}$-D-$Arg^{28}$-$Har^{29}$-$NH_2$ (Peptide 80)

{[$CH_3(CH_2)_6CO$-$Tyr^1$, D-$Arg^2$, $Phe(pCl)^6$, $Ala^8$, $His^9$, $Tyr(Et)^{10}$, $His^{11}$, $Abu^{15}$, $Nle^{27}$, D-$Arg^{28}$, $Har^{29}$]hGH-RH(1-29)$NH_2$}

The synthesis is conducted in a stepwise manner using manual solid phase peptide synthesis equipment Briefly, para-methylbenzhydrylamine (MBHA) resin (Bachem, King of Prussia, Pa.) (720 mg, 0.50 mmol) is neutralized with 5% DIEA in DCM and washed according to the protocol described in Table I. The solution of Boc-Har($NO_2$)—OH (500 mg, 1.5 mmol) in DMF-DCM (1:1) is shaken with the neutralized resin and DIC (235 μL, 1.5 mmol) in a manual solid phase peptide synthesis apparatus for 1 hour. After the completion of the coupling reaction is proved by negative ninhydrin test, the deprotection and neutralization protocols described in Table I are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ):OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Et)-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH.

These protected amino acid residues (also commonly available from Bachem) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 μL, 1.5 mmol) with the exceptions of Boc-Asn-OH and Boc-Gln-OH which are coupled with their preformed HOBt esters. After removal of the Na-Boc protecting group from $Tyr^1$, the peptide is acylated overnight with octanoic acid $[CH_3(CH_2)_6COOH]$ (475 μL, 3 mmol) using DIC (235 μL, 1.5 mmol) as a coupling agent.

In order to cleave the peptide from the resin and deprotect it, a portion of 130 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 75 mg crude product is obtained.

The crude peptide is checked by analytical HPLC using a Hewlett-Packard Model HP-1090 liquid chromatograph with a Supelco Discovery HS C18 reversed-phase column (2.1 mm×5 cm, packed with C18 silica gel, 120 Å pore size, 3 μm particle size) (Supelco, Bellefonte, Pa.) and linear gradient elution (e.g., 40-70% B), with a solvent system consisting of (A) 0.1% aqueous TFA and (B) 0.1% TFA in 70% aqueous MeCN. For purification by semipreparative HPLC, 75 mg of crude peptide is dissolved in $AcOH/H_2O$, stirred, filtered and applied on a Beckman Ultraprep ODS column (21.2 mm×15 cm, packed with C18 silica gel, 300 Å pore size, 10 μm particle size). The column is eluted with a solvent system described above in a linear gradient mode (e.g., 40-60% B in 120 min); flow rate 10 mL/min. The eluent is monitored at 220 nm, and fractions are examined by analytical HPLC. Fractions with purity higher than 95% are pooled and lyophilized to give 7.7 mg pure product The analytical HPLC is carried out on a Supelco C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

Peptide 2, Peptide 4, Peptide 6, Peptide 8, Peptide 10, Peptide 12, Peptide 14, Peptide 16, Peptide 17, Peptide 79, Peptide 86, Peptide 92, Peptide 93, Peptide 94, Peptide 95, Peptide 96, Peptide 104, and Peptide 105 are synthesized in the same manner as Peptide 80, except that these peptides also contain other amino acid substitutions and other acyl moieties originating from fatty acids at their N-termini.

For the synthesis of Peptide 2, the chemical structure of which is $[CH_3(CH_2)_4CO-Tyr^1, D-Arg^2, Phe(pCl)^6, Arg^9, Abu^{15}, Nle^{27}, D-Arg^{28}, Har^{29}]hGH-RH(1-29)NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2CtZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_4COOH$.

For the synthesis of Peptide 4, the chemical structure of which is $[CH_3(CH_2)_6CO-Tyr^1, D-Arg^2, Phe(pCl)^6, Arg^9, Abu^{15}, Nle^{27}, D-Arg^{28}, Har^{29}]hGH-RH(1-29)NH_2$ the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6COOH$.

For the synthesis of Peptide 6, the chemical structure of which is $[CH_3(CH_2)_8CO-Tyr^1, D-Arg^2, Phe(pCl)^6, Arg^9, Abu^{15}, Nle^{27}, D-Arg^{28}, Har^{20}]hGH-RH(1-29)NH_2$, the following protected amino acids are coupled in the indicated order on the MBHA resin: Boc-Har($NO_2$)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_8COOH$.

For the synthesis of Peptide 8, the chemical structure of which is $[CH_3(CH_2)_{10}CO-Tyr^1, D-Arg^2, Phe(pCl)^6, Arg^9, Abu^{15}, Nle^{27}, D-Arg^{28}, Har^{29}]hGH-RH(1-29)NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-H, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_{10}COOH$.

For the synthesis of Peptide 10, the chemical structure of which is $[CH_3(CH_2)_{12}CO-Tyr^1, D-Arg^2, Phe(pCl)^6, Arg^9, Abu^{15}, Nle^{27}, D-Arg^{28}, Har^{29}]hGH-RH(1-29)NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc- Ser(Bzl)-OH, Boc-Leu-OH, Boc-Gln-OH, Boc-Abu-OH, Boc, Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_{12}COOH$.

For the synthesis of Peptide 12, the chemical structure of which is
[$CH_3(CH_2)_{14}$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_{14}COOH$.

For the synthesis of Peptide 14, the chemical structure of which is
[$CH_3(CH_2)_6$CO-Tyr$^1$, D-Arg$^2$, Phe(pCl)$^6$, Arg$^9$, Abu$^{15}$Nle$^{27}$, Har$^{28}$, D-Arg$^{29}$]hGH-RH(1-29)NH$_2$, the following protected amino acids are coupled in the indicated order on the MBHA resin: Boc-D-Arg(Tos)-OH, Boc-Har(NO$_2$)—OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-H, Boc-Ala-OH, Boc-Asp(OcHx)-OH, Boc-D-Arg(Tos)-OH, Boc-Tyr(2BrZ)4H, followed by acylation with $CH_3(CH_2)_6COOH$.

For the synthesis of Peptide 16, the chemical structure of which is
[$CH_3(CH_2)_{14}$CO-Phe$^0$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, Boc-Phe-OH, followed by acylation with $CH_3(CH_2)_{14}COOH$.

For the synthesis of Peptide 17, the chemical structure of which is
[$CH_3(CH_2)_{14}$CO-D-Phe$^0$, D-Arg$^2$, Phe(pCl)$^5$, Arg$^9$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)-OH, Boc-D-Arg(Tos)-OH, Boc-Nle-OH, Boc-Ile-OH, Boc-Asp(OcHx)-OH, Boc-Gln-OH, Boc-Leu-H, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, Boc-D-Phe-OH, followed by acylation with $CH_3(CH_2)_{14}COOH$.

For the synthesis of Peptide 79, the chemical structure of which is
[$CH_3(CH_2)_6$CO-Tyr$^1$, D-Arg$^2$, Phe(pCl)$^6$, Cit$^8$, His$^9$, Tyr(Et)$^{10}$, His$^{11}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Et)-OH, Boc-His(Bom)-OH, Boc-Cit-OH: Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylaton with $CH_3(CH_2)_6COOH$.

For the synthesis of Peptide 86, the chemical structure of which is
[$CH_3(CH_2)_6$CO-Tyr$^1$, D-Arg$^2$, Phe(pCl)$^6$, Ala$^8$, His$^9$, Tyr(Et)$^{10}$, His$^{11}$, Abu$^{15}$, His$^{20}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Et)-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6COOH$.

For the synthesis of Peptide 92, the chemical structure of which is
[$CH_3(CH_2)_6$CO-Tyr$^1$, D-Arg$^2$, Phe(pCl)$^6$, His$^9$, Tyr(Et)$^{10}$, His$^{11}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Abu(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Et)-OH, Boc-His(Bom)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6COOH$.

For the synthesis of Peptide 93, the chemical structure of which is
[$CH_3(CH_2)_6$CO-Tyr$^1$, D-Arg$^2$, Phe(pCl)$^6$, Ala$^8$, His$^9$, Cit$^{15}$, Nle$^{27}$, D-Arg28, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc- Ser(Bzl)-OH, Boc-Leu-OH, Boc-Gln-OH, Boc-Cit-OH, Boc-Leu-OH, Boc-Val-OH, Boc-Lys(2ClZ)-OH, Boc-Arg(Tos)-OH, Boc-Tyr(2BrZ)-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6COOH$.

For the synthesis of Peptide 94, the chemical structure of which is

[$CH_3(CH_2)_6CO$-$Tyr^1$, $D$-$Arg^2$, $Phe(pCl)^6$, $Ala^8$, $His^9$, $Tyr(Et)^{10}$, $His^{11}$, $His^{15}$, $His^{20}$, $Nle^{27}$, $D$-$Arg^{28}$, $Har^{29}$]hGH-RH(1-29)$NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-His(Bom)-OH, Boc-Leu-OH, Boc-Val-OH, Boc-Lys(2ClZ)-OH, Boc-His(Bom)-OH, Boc-Tyr(Et)-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6COOH$.

For the synthesis of Peptide 95, the chemical structure of which is

[$CH_3(CH_2)_6CO$-$Tyr^1$, $D$-$Arg^2$, $Phe(pCl)^6$, $Ala^8$, $His^9$, $Tyr(Et)^{10}$, $His^{11}$, $Orn^{12}$, $Abu^{15}$, $Orn^{21}$, $Nle^{27}$, $D$-$Arg^{28}$, $Har^{29}$]hGH-RH(1-29)$NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)OH, Boc-Tyr(Et)OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6COOH$.

For the synthesis of Peptide 96, the chemical structure of which is

[$CH_3(CH_2)_6CO$-$Tyr^1$, $D$-$Arg^2$, $Phe(pCl)^6$, $Ala^8$, $His^9$, $Tyr(Et)^{10}$, $His^{11}$, $Orn^{12}$, $Abu^{15}$, $His^{20}$, $Orn^{21}$, $Nle^{27}$, $D$-$Arg^{28}$, $Har^{29}$]hGH-RH(1-29)$NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boe-Val-OH, Boc-Orn(2ClZ)-OH, Boc-His(Bom)-OH, Boc-Tyr(Et)-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6COOH$.

For the synthesis of Peptide 104, the chemical structure of which is

[$CH_3(CH_2)_6CO$-$Tyr^1$, $D$-$Arg^2$, $Phe(pCl)^6$, $Ala^8$, $His^9$, $Dip^{10}$, $His^{11}$, $Orn^{12}$, $Abu^{15}$, $His^{11}$, $Orn^{21}$, $Nle^{27}$-$D$-$Arg^{28}$, $Har^{29}$]hGH-RH(1-29)$NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Dip-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6COOH$.

For the synthesis of Peptide 105, the chemical structure of which is

[$CH_3(CH_2)_6CO$-$Tyr^1$, $D$-$Arg^2$, $Phe(pCl)^6$, $Ala^8$, $His^9$, $Phe(pNO_2)^{10}$, $His^{11}$, $Orn^{12}$, $Abu^{15}$, $His^{20}$, $Orn^{21}$, $Nle^{27}$, $D$-$Arg^{28}$, $Har^{29}$]hGH-RH(1-29)$NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Phe(p$NO_2$)—OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6COOH$.

HF cleavage and deprotection, and subsequent purification by semipreparative HPLC of Peptide 2, Peptide 4, Peptide 6, Peptide 8, Peptide 10, Peptide 12, Peptide 14, Peptide 16, Peptide 17, Peptide 79, Peptide 86, Peptide 92, Peptide 93, Peptide 94, Peptide 95, Peptide 96, Peptide 104, and Peptide 105 are done as described in the case of Peptide 80. The purified compounds are judged to be substantially (>95%) pure by analytical HPLC. Their molecular masses are checked by electrospray mass spectrometry, and the expected amino acid compositions are confirmed by amino acid analysis.

Example II

HOOC$(CH_2)_{12}$CO-$Tyr^1$D-$Arg^2$-$Asp^3$-$Ala^4$-$Ile^5$-$Phe(pCl)^6$-$Thr^7$-$Asn^8$-$Arg^9$-$Tyr^{10}$-$Arg^{11}$, $Lys^{12}$, $Val_{13}$-$Leu^{14}$-$Abu^{15}$-$Gln_{16}$-$Leu^{17}$-$Ser^{18}$-$Ala^{19}$-$Arg^{20}$-$Lys^{21}$-$Leu^{22}$-$Leu^{23}$-$Gln^{24}$-$Asp^{25}$-$Ile^{26}$-$Nle^{27}$-$D$-$Arg^{28}$-$Har^{29}$-$NH_2$ (Peptide 11)

{[HOOC$(CH_2)_{12}$CO-$Tyr^1$, $D$-$Arg^2$, $Phe(pCl)^6$, $Arg^9$, $Abu^{15}$, $Nle^{27}$, $D$-$Arg^{28}$, $Har^{29}$]hGH-RH(1-29)$NH_2$}

The synthesis is conducted in a stepwise manner using manual solid phase peptide synthesis equipment. Briefly, MBHA resin (Bachem, King of Prussia, Pa.) (720 mg, 0.50 mmol) is neutralized with 5% DIEA in DCM and washed according to the protocol described in Table I. The solution of Boc-Har($NO_2$)—OH (500 mg, 1.5 mmol) in DMF-DCM (1:1) is shaken with the neutralized resin and DIC (235 µL, 1.5 mmol) in a manual solid phase peptide synthesis apparatus for 1 hour. After the completion of the coupling reaction is proved by negative ninhydrin test, the deprotecton and neutralization protocols described in Table I are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH. The protected amino acids (1.5 mmol each) are coupled with DIC (235 µL, 1.5 mmol) with the exceptions of Boc-Asn-OH and Boc-Gln-OH which are coupled with their preformed HOBt esters.

After removal of the $N^\alpha$-Boc protecting group from $Tyr^1$, the peptide is acylated with the pre-formed symmetrical anhydride of 1,12-dodecanedicarboxylic acid which is prepared as follows. For synthesis on the scale of 0.5 mmol peptide, 388 mg (1.5 mmol) 1,12-dodecanedicarboxylic acid $[HOOC(CH_2)_{12}COOH]$ is dissolved in 5 to 10 mL of DMF-DCM (1:1), 235 µL (1.5 mmol) DIC is added to this solution, and the mixture is allowed to stand at room temperature for 30 min. After this period of time, the mixture is transferred into the synthesis vessel containing the peptide-resin with a free amino terminus on $Tyr^1$, and acylation is carried out overnight.

In order to cleave the peptide from the resin and deprotect it, a portion of 274 mg of the dried peptide resin is stirred with 0.5 mL m-cresol and 5 mL hydrogen fluoride (HF) at 0° C. for 2 hours; After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 160 mg crude product is obtained.

The crude peptide is checked by analytical HPLC using a Hewlett-Packard Model HP-1090 liquid chromatograph with a Supelco Discovery HS C18 reversed-phase column (2.1 mm×5 cm, packed with C18 silica gel, 120 Å pore size, 3 µm particle size) (Supelco, Bellefonte, Pa.) and linear gradient elution (e.g., 50-80% B), with a solvent system consisting of (A) 0.1% aqueous TFA and (B) 0.1% TFA in 70% aqueous MeCN. For purification by semipreparative HPLC, 160 mg of crude peptide is dissolved in AcOH/$H_2O$, stirred, filtered and applied on a Beckman Ultraprep ODS column (21.2 mm×15 cm, packed with C18 silica gel, 300 Å pore size, 10 µm particle size). The column is eluted with a solvent system described above in a linear gradient mode (e.g., 50-70% B in 120 min); flow rate 10 mL/min. The eluent is monitored at 220 nm, and fractions are examined by analytical HPLC. Fractions with purity higher than 95% are pooled and lyophilized to give 6.0 mg pure product The analytical HPLC is carried out on a Supelco C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

Peptide 3, Peptide 5, Peptide 7, Peptide 9, Peptide 13, Peptide 25, Peptide 81, Peptide 82, Peptide 88, Peptide 102, Peptide 108, and Peptide 109 are synthesized in the same manner as Peptide 11, except that these peptides also contain other amino acid substitutions and other acyl moieties originating from dicarboxylic acids at their N-termini.

For the synthesis of Peptide 3, the chemical structure of which is $[HOOC(CH_2)_4CO\text{-}Tyr^1, D\text{-}Arg^2, Phe(pCl)^6, Arg^9, Abu^{15}, Nle^{27}, D\text{-}Arg^{28}, Har^{29}]hGH\text{-}RH(1\text{-}29)NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $HOOC(CH_2)_4COOH$.

For the synthesis of Peptide 5, the chemical structure of which is $[HOOC(CH_2)_6CO\text{-}Tyr^1, D\text{-}Arg^2, Phe(pCl)^6, Arg^9, Abu^{15}, Nle^{27}, D\text{-}Arg^{28}, Har^{29}]hGH\text{-}RH(1\text{-}19)NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $HOOC(CH_2)_6COOH$.

For the synthesis of Peptide 7, the chemical structure of which is $[HOOC(CH_2)_8CO\text{-}Tyr^1, D\text{-}Arg^2, Phe(pCl)^6, Arg^9, Abu^{15}, Nle^{27}, D\text{-}Arg^{28}, Har^{29}]hGH\text{-}RH(1\text{-}29)NH_2$, the following protected amino acids are coupled in the indicated order on the MBHA resin: Boc-Har($NO_2$)—OH, Boc-D-Arg(Tos)-OH, Boc-Nle-OH, Boc-Ile)-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $HOOC(CH_2)_8COOH$.

For the synthesis of Peptide 9, the chemical structure of which is $[HOOC(CH_2)_{10}CO\text{-}Tyr^1, D\text{-}Arg^2, Phe(pCl)^6, Arg^9, Abu^{15}, Nle^{27}, D\text{-}Arg^{28}, Har^{29}]hGH\text{-}RH(1\text{-}29)NH_2$, the following protected amino acids are coupled in the indicated order on the MBHA resin: Boc-Har($NO_2$)—OH, Boc-D-Arg(Tos)-OH, Boc-Nle-OH, Boc-Nle-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $HOOC(CH_2)_{10}COOH$.

For the synthesis of Peptide 13, the chemical structure of which is $[HOOC(CH_2)_{14}CO\text{-}Tyr^1, D\text{-}Arg^2, Phe(pCl)^6, Arg^9, Abu^{15}, Nle^{27}, D\text{-}Arg^{28}, Har^{29}]hGH\text{-}RH(1\text{-}29)NH_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with HOOC(CH$_2$)$_{14}$COOH.

For the synthesis of Peptide 25, the chemical structure of which is

[HOOC(CH$_2$)$_{12}$CO-Tyr$^1$, D-Arg$^2$, Phe(pCl)$^6$, Cit$^8$, Cit$^9$, Abu$^{15}$, Nle$^{27}$, D-Arg$^{28}$, H$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2C[Z)OH, Boc-Arg(Tos)-OH, Boc-Tyr(2BrZ)-OH, Boc-Cit-OH, Boc-Cit-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with HOOC(CH$_2$)$_{12}$COOH.

For the synthesis of Peptide 81, the chemical structure of which is

[HOOC(CH$_2$)$_8$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$Har$^{29}$]hGH-RH(1-29)NH$_2$, the following protected amino acids are coupled in the indicated order on the MBHA resin, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Et)-OH, Boc-His(Bom)-OH, Boc-Ala-OH, Boc-Thr(Bzl)-OH, Boc-Phe(pCl) OH, Boc-Ile-OH, Boc-Ala-OH, Boc-Asp(OcHx)-OH, Boc-D-Arg(Tos)-OH, Boc-Tyr(2BrZ)-OH, followed by acylation with HOOC(CH$_2$)$_8$COOH.

For the synthesis of Peptide 82, the chemical structure of which is

[HOOC(CH$_2$)$_{12}$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val)-OH, Boc-Lys(2ClZ)-OH, Boc-His(Bom)-OH, Boc-Tyr(Et)-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with HOOC(CH$_2$)$_{12}$COOH.

For the synthesis of Peptide 88, the chemical structure of which is

[HOOC(CH$_2$)$_{12}$CO-Tyr$^1$, D-Arg$^2$, Phe(pCl)$^6$, Ala$^8$, His$^9$, Tyr(Et)$^{10}$, His$^{11}$, Abu$^{15}$, His$^{20}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Et)-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with HOOC(CH$_2$)$_{12}$COOH.

For the synthesis of Peptide 102, the chemical structure of which is

[HOOC(CH$_2$)$_{12}$CO-Tyr$^1$, D-Arg$^2$, Phe(pCl)$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{26}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Et)OH, Boc-His(Bom)-OH, Boc-Ala-4H, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with HOOC(CH$_2$)$_{12}$COOH.

For the synthesis of Peptide 108, the chemical structure of which is (HOOC(CH$_2$)$_{12}$CO-Tyr$^1$, D-Arg$^2$, Phe(pCl)$^6$, Ala$^8$, His$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-H, Boc-Orn(2ClZ)-OH, Boc-His(Bom)-OH, Boc-Dip-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with HOOC(CH$_2$)$_{12}$COOH.

For the synthesis of Peptide 109, the chemical structure of which is

[HOOC(CH$_2$)$_{12}$CO-Tyr$^1$, D-Arg$^2$, Phe(pCl)$^6$, Ala$^8$, His$^9$, Phe(pNO$_2$)$^{11}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-H, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Phe(pNO$_2$)—OH, Boc-His(Bom)-OH, Boc-Ala-OH, Boc-Thr(Bzl)-OH, Boc-Phe(pCl)—OH, Boc- Ile-OH, Boc-Ala-OH, Boc-Asp(OcHx)-OH, Boc-D-Arg (Tos)-OH, Boc-Tyr(2BrZ) OH, followed by acylation with HOOC(CH$_2$)$_{12}$COOH.

HF cleavage and deprotection, and subsequent purification by semipreparative HPLC of Peptide 3, Peptide 5, Peptide 7. Peptide 9, Peptide 13, Peptide 25, Peptide 81, Peptide 82, Peptide 88, Peptide 102, Peptide 108, and Peptide 109 are done as described in the case of Peptide 11. The purified compounds are judged to be substantially (>95%) pure by analytical HPLC. Their molecular masses are checked by electrospray mass spectrometry, and the expected amino acid compositions are confirmed by amino acid analysis.

Example III

PhAc-Tyr$_1$-D-Arg$^2$-Asp$^3$-Ala$^4$-Ile$^5$-Phe(pCl)$^6$-Thr$^7$-Asn$^8$-Har$_9$-Tyr(Me)$^{10}$-His$^{11}$-Lys$^{12}$-Val$^{13}$-Leu$^{14}$-Abu$^{15}$-Gln$^{16}$-Leu$_{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ (Peptide 62)
{[PhAc-Tyr$^1$, D-Arg$^2$, Phe(pCl)$^6$, Har$^9$, Tyr(Me)$^{10}$, His$^{11}$, Abu$^{15}$, Nle$^{27}$, D-Arg$^{28}$, Har$^{29}$]hGH-RH(1-29)NH$_2$}

The synthesis is conducted in a stepwise manner using manual solid phase peptide synthesis equipment. Briefly, para-methylbenzhydrylamine (MBHA) resin, (Bachem, King of Prussia, Pa.) (720 mg, 0.50 mmol) is neutralized with 5% DIEA in DCM and washed according to the protocol described in Table I. The solution of Boc-Har(NO$_2$)—OH (500 mg, 1.5 mmol) in DMF-DCM (1:1) is shaken with the neutralized resin and DIC (235 µL, 1.5 mmol) in a manual solid phase peptide synthesis apparatus for 1 hour. After the completion of the coupling reaction is proved by negative ninhydrin test, the deprotection and neutralization protocols described in Table I are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg (Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp (OcHx)-OH, Boc-D-Arg(Tos)-OH, Boc-Tyr(2BrZ)-OH. The protected amino acids (1.5 mmol each) are coupled with DIC (235 µL, 1.5 mmol) with the exceptions of Boc-Asn-OH and Boc-Gln-OH which are coupled with their preformed HOBt esters. After removal of the N$^\alpha$-Boc protecting group from Tyr$^1$, the peptide is acylated with phenylacetic acid (PhAc-OH) (272 mg, 2 mmol) using DIC (313 µL, 2 mmol).

In order to cleave the peptide from the resin and deprotect it, a portion of 286 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 155 mg crude product is obtained.

The crude peptide is checked by analytical HPLC using a Hewlett-Packard Model HP-1090 liquid chromatograph with a Supelco Discovery HS C18 reversed-phase column (2.1 mm×5 cm, packed with C18 silica gel, 120 Å pore size, 3 µm particle size) (Supelco, Bellefonte, Pa.) and linear gradient elution (e.g., 40-70% B), with a solvent system consisting of (A) 0.1% aqueous TFA and (B) 0.1% TFA in 70% aqueous MeCN. For purification by semipreparative HPLC, 155 mg of crude peptide is dissolved in AcOH/H$_2$O, stirred, filtered and applied on a Beckman Ultraprep ODS column (21.2 mm×15 cm, packed with C18 silica gel, 300 Å pore size, 10 µm particle size). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 13.3 mg pure product The analytical HPLC is carried out on a Supelco C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

Peptide 15, Peptide 18, Peptide 19, Peptide 21, Peptide 22, Peptide 23, Peptide 24, Peptide 26, Peptide 27, Peptide 28, Peptide 32, Peptide 33, Peptide 34, Peptide 35, Peptide 36, Peptide 37, Peptide 38, Peptide 39, Peptide 40, Peptide 41, Peptide 42, Peptide 43, Peptide 53, Peptide 54, Peptide 55, Peptide 57, Peptide 58, Peptide 63, Peptide 65, Peptide 69, Peptide 84, Peptide 85, Peptide 90, and Peptide 91 are synthesized in the same manner as Peptide 62, except that these peptides also contain other substitutions.

For the synthesis of Peptide 15, the chemical structure of which is
[PhAc-Tyr$^1$, D-Arg$^2$, Phe(pCl)$^6$, Arg$^9$, Abu$^{15}$, Nle$^{27}$, Har$^{28}$, D-Arg$^{29}$, hGH-RH(1-29)NH$_2$, the following protected amino acids are coupled in the indicated order on the MBHA resin: Boc-D-Arg(Tos)-OH, Boc-Har(NO$_2$)—OH, Boc-Nle-OH, Boc-Ile-OH, Boc-Asp (OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg (Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 18, the chemical structure of which is
[PhAc-Arg$^0$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp (OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg (Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, Boc-Arg(Tos)-OH, followed by acylation with PhAc-OH.

For the synthesis of Peptide 19, the chemical structure of which is
[PhAc-D-Arg$^0$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$, the following protected amino acids are coupled in the indicated order on the MBHA-resin: Boc-Har(NO$_2$)—OH, Boc- D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ) OH, Boc-D-Arg(Tos)-OH, followed by acylation with PhAc-OH.

For the synthesis of Peptide 21, the chemical structure of which is

[PhAc-Tyr$^1$, D-Arg$^2$, Phe(pCl)$^6$, Cit$^9$, Arg$^9$, Abu$^{15}$, Nle$^{27}$, D-Arg$^{28}$, Har$^{29}$, hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH; Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Cit-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 22, the chemical structure of which is

[PhAc-Tyr$^1$, D-Arg$^2$, Phe(pCl)$^6$, Cit$^8$, Cit$^9$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH. Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Cit-OH, Boc-Cit-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 23, the chemical structure of which is

[PhAc-Tyr$^1$, D-Arg$^2$, Phe(pCl)$^6$, Cit$^8$, Arg$^9$, Abu$^{15}$, Nle$^{27}$, Har$^{28}$, D-Arg$^{29}$]hGH-RH(1-29)NH$_2$, the following protected amino acids are coupled in the indicated order on the MBHA resin: Boc-D-Arg(Tos)-OH, Boc-Har(NO$_2$)—OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Cit-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 24, the chemical structure of which is

[PhAc-Tyr$^1$, D-Arg$^2$, Phe(pCl)$^6$, Cit$^8$, Cit$^9$, Abu$^{15}$, Nle$^{27}$, Har$^{28}$, D-Arg$^{29}$]hGH-RH(1-29)NH$_2$, the following protected amino acids are coupled in the indicated order on the MBHA resin: Boc-D-Arg(Tos)-OH, Boc-Har(NO$_2$)—OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Cit-OH, Boc-Cit-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 26, the chemical structure of which is

[PhAc-Tyr$^1$, D-Arg$^2$, Phe(pCl)$^6$, D-Ala$^8$, Arg$^9$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-D-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 27, the chemical structure of which is

[PhAc-Tyr$^1$, D-Arg$^2$, Phe(pCl)$^6$, Abu$^8$, Arg$^9$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-DAM(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Abu-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 28, the chemical structure of which is

[PhAc-Tyr$^1$, D-Arg$^2$, Phe(pCl)$^6$, Cit$^9$, Abu$^{15}$, Nle$^{27}$, Har$^{28}$, D-Arg$^{29}$]hGH-RH(1-29)NH$_2$, the following protected amino acids are coupled in the indicated order on the MBHA resin: Boc-D-Arg(Tos)-OH, Boc-Har(NO$_2$)—OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Cit-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 32, the chemical structure of which is

[PhAc-Tyr$^1$, D-Arg$^2$, Phe(pCl)$^6$, Arg$^9$, His$^{10}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-His(Bom)-OH, Boc-Arg(Tos)-OH, Boc-Asn-OH, Boc-Thr(Bzl)-OH, Boc-Phe(pCl)—OH, Boc-Ile- OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 33, the chemical structure of which is

[PhAc-Tyr$^1$, D-Arg$^2$, Phe(pCl)$^6$, Arg$^9$, Cha$^{10}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Cha-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 34, the chemical structure of which is

[PhAc-Tyr$^1$, D-Arg$^2$, Phe(pCl)$^6$, Har$^9$, Tpi$^{10}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tpi-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 35, the chemical structure of which is

[PhAc-Tyr$^1$, D-Arg$^2$, Phe(pCl)$^6$, Har$^9$, 2-Nal$^{10}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-2-Nal-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 36, the chemical structure of which is

[PhAc-Tyr$^1$, D-Arg$^2$, Phe(pCl)$^6$, Har$^9$, Dip$^{10}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-Har(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Dip-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 37, the chemical structure of which is

[PhAc-Tyr$^1$, D-Arg$^2$, Phe(pCl)$^6$, Har$^9$, Phe(pNH$_2$)$^{10}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Phe(pNH-Z)OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 38, the chemical structure of which is

[PhAc-Tyr$^1$, D-Arg$^2$, Phe(pCl)$^6$, Har$^9$, Trp$^{10}$, Abu$^{15}$, Nle$^{27}$, D-Arg$^{26}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Trp(For)OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 39, the chemical structure of which is (PhAc-Tyr$^1$, D-Arg$^2$, Phe(pCl)$^6$, Har$^9$, Phe(pNO$_2$)$^{10}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Phe(pNO$_2$)—OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 40, the chemical structure of which is

[PhAc-Tyr$^1$, D-Arg$^2$, Phe(pCl)$^6$, Har$^9$, 3-Pal$^{10}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-3-Pal-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 41, the chemical structure of which is

[PhAc-Tyr$^1$, D-Arg$^2$, Phe(pCl)$^6$, Har$^9$, Tyr(Et)$^{10}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Et)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 42, the chemical structure of which is

[PhAc-His$^1$, D-Arg$^2$, Tyr$^6$, Har$^9$, Bpa$^{10}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Bpa-OH, Boc-Har(NO$_2$)—OH, Boc-Asn-OH, Boc-Thr(Bzl)-OH, Boc-Tyr(2BrZ)-OH, Boc-Ile-OH, Boc-Ala-OH, Boc-Asp(OcHx)-OH, Boc-D-Arg(Tos)-OH, Boc-His(Bom)-OH, followed by acylation with PhAc-OH.

For the synthesis of Peptide 43, the chemical structure of which is

[PhAc-Tyr$^1$, D-Arg$^2$, Phe(pCl)$^6$, Arg$^9$, Har$^{12}$, Abu$^{15}$, Nle$^{27}$, Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Har(NO$_2$)—OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 53, the chemical structure of which is

[Hca-Tyr$^1$, Arg$^2$, Phe(pCl)$^6$, Har$^9$, Tyr(Me)$^{10}$, Abu$^{11}$, Nle$^{27}$, D-Arg$^{28}$, Har$^{29}$, Har$^{30}$]hGH-RH(1-30NH$_2$, the following protected amino acids are coupled in the indicated order on the MBHA resin: Boc-Har(NO$_2$)-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with hydrocinnamic acid (Hca-OH).

For the synthesis of Peptide 54, the chemical structure of which is

[Dat-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, Har$^{30}$]hGH-RH(1-30)NH$_2$, the following protected amino acids are coupled in the indicated order on the MBHA resin: Boc-Har(NO$_2$)—OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with des-amino-tyrosine (Dat).

For the synthesis of Peptide 55, the chemical structure of which is

[Ipa-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, Har$^{30}$]hGH-RH(1-30)NH$_2$, the following protected amino acids are coupled in the indicated order on the MBHA resin: Boc-Har(NO$_2$)—OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Ser-Tyr(Me)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with indole-3-propionic acid (Ipa-OH).

For the synthesis of Peptide 57, the chemical structure of which is

[Hca-Tyr$^1$, D-Arg$^2$, Phe(pCl)$^6$, Har$^9$, Tyr(Me)$^{10}$, Abu$^{11}$, Nle$^{27}$, D-Arg$^{28}$, D-Arg$^{29}$, Har$^{30}$]hGH-RH(1-29)NH$_2$, the following protected amino acids are coupled in the indicated order on the MBHA resin: Boc-Har(NO$_2$)—OH, Boc-D-Arg(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu)-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with Hca-OH.

For the synthesis of Peptide 58, the chemical structure of which is

[Hca-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, D-Arg$^{30}$]hGH-RH(1-29)NH$_2$, the following protected amino acids are coupled in the indicated order on the MBHA resin: Boc-D-Arg(Tos)-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with Hca-OH.

For the synthesis of Peptide 63, the chemical structure of which is

[PhAc-Tyr$^1$, D-Arg$^2$, Phe(pCl)$^6$, Har$^9$, Tyr(Me)$^{10}$, Har$^{11}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Har(NO$_2$)—OH, Boc-Tyr(Me)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH followed by acylation with PhAc-OH.

For the synthesis of Peptide 65, the chemical structure of which is

[PhAc-Tyr$^1$, D-Arg$^2$, Phe(pCl)$^5$, Har$^9$, Tyr(Me)$^{10}$, Cit$^{11}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Cit-OH, Boc-Tyr(Me)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 69, the chemical structure of which is

[PhAc-Tyr$^1$, D-Arg$^2$, Phe(pCl)$^6$, His$^9$, Tyr(Me)$^{10}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-His(Bom)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 84, the chemical structure of which is

[PhAc-Tyr$^1$, D-Arg$^2$, Phe(pCl)$^6$, Har$^9$, Tyr(Me)$^{10}$, Abu$^{15}$, His$^{20}$, Nle$^{21}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-Ser(Tos)-OH, Boc-Tyr(2BrZ)-OH, followed by acylation with PhAc-OH.

For the synthesis of Peptide 85, the chemical structure of which is

[PhAc-Tyr$^1$, D-Arg$^2$, Phe(pCl)$^6$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 90, the chemical structure of which is

[PhAc-Tyr$^1$, D-Arg$^2$, Phe(pCl)$^6$, Arg$^9$, Cit$^{15}$, Nle$^{27}$, D-Arg$^{28}$, Har$^{29}$]hGH-RH(1-29)NH$_2$, the following protected amino acids are coupled in the indicated order on the MBHA resin. Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Cit-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 91, the chemical structure of which is

[1-Nac-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Et)-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with 1-naphthylacetic acid (1-Nac-OH).

HF cleavage and deprotection, and subsequent purification by semipreparative HPLC of Peptide 15, Peptide 18, Peptide 19, Peptide 21, Peptide 22, Peptide 23, Peptide 24, Peptide 26, Peptide 27, Peptide 28, Peptide 32, Peptide 33, Peptide 34, Peptide 35, Peptide 36, Peptide 37, Peptide 38, Peptide 39, Peptide 40, Peptide 41, Peptide 42, Peptide 43, Peptide 53, Peptide 54, Peptide 55, Peptide 57, Peptide 58, Peptide 63, Peptide 65, Peptide 69, Peptide 84, Peptide 85, Peptide 90, and Peptide 91 are done as described in the case of Peptide 62. The purified compounds are judged to be substantially (>95%) pure by analytical HPLC. Their molecular masses are checked by electrospray mass spectrometry, and the expected amino acid compositions are confirmed by amino acid analysis.

Example IV

PhAc-Tyr$_1$-D-Arg$^2$-Asp$^3$-Ala$^4$-Ile$^5$Phe(pCl)$^6$-Thr$^7$-Asn$^8$-Amp$^9$-Tyr(Me)$^{10}$-Arg$^{11}$-Lys$^{12}$-Val$^{13}$-Leu$^{14}$-Abu$^{15}$-Gln$^{16}$-Leu$_{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ (Peptide 67)

{[PhAc-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$}

The synthesis is conducted in a stepwise manner using manual solid phase peptide synthesis equipment Briefly, para-methylbenzhydrylamine (MBHA) resin (Bachem, King of Prussia, Pa.) (720 mg, 0.50 mmol) is neutralized with 5% DIEA in DCM and washed according to the protocol described in Table I. The solution of Boc-Har(NO$_2$)—OH (500 mg, 1.5 mmol) in DMF-DCM (1:1) is shaken with the neutralized resin and DIC (235 µL, 1.5 mmol) 1 h a manual solid phase peptide synthesis apparatus for 1 hour. After the completion of the coupling reaction is proved by negative ninhydrin test, the deprotection and neutralization protocols described in Table I are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence. Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Amp(Alloc)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH. The protected, noncoded amino acid Boc-Amp(Alloc)-OH is commercially available from RSP Amino Acid Analogues, Inc. (Worcester, Mass.). The protected amino acids (1.5 mmol each) are coupled with DIC (235 µL, 1.5 mmol), with the exceptions of Boc-Amp(Alloc)-OH, Boc-Asn-OH and Boc-Gln-OH which are coupled with 569 mg HBTU+203 mg HOBt+522 µL DIEA (1.5:1.5:3 mmol). After removal of the N$^\alpha$-Boc protecting group from Tyre, the peptide is acylated with phenylacetic acid (PhAc-OH) (272 mg, 2 mmol) using DIC (313 µL, 2 mmol). The finished peptidyl resin, with all the side-chain protecting groups still attached, is washed 3× with DCM, 3× with MeOH, and dried under high vacuum.

The peptide-resin is then subjected to Pd(0)catalyzed removal of the Alloc protecting group from the Amp$^9$ residue of the peptide chain, by using the procedure described in the Novabiochem (San Diego, Calif.) Catalog 2002/2003. A portion of 255 mg peptidyl resin, with an estimated peptide content of 0.033 mmol, is weighed into a test tube and the tube is sealed with a rubber septum. The test tube is flushed with a stream of argon (Ar) gas delivered from a needle inserted through the septum. 116 mg Pd(PPh$_3$)$_4$ (0.1 mmol, or 3 equiv. relative to the Alloc groups present on the peptidyl resin) is weighed into another dry test tube, 45 mL of CHCl$_3$—AcOH—N-methylmorpholine (37:2:1 vol:vol:vol) is added, the catalyst is dissolved by bubbling a stream of Ar through the solution, and the tube is sealed with a rubber septum. This solution is transferred using an Ar flushed gas-fight syringe to the tube containing the resin, and the resulting mixture is left to stand for 2 hours with an occasional gentle agitation. Next the resin is transferred to a sintered glass funnel and washed consecutively with 0.5% DIEA in DMF (to neutralize the resin) and sodium diethyldithiocarbamate (0.5% w/w) in DMF (to remove the catalyst). After another wash with MeOH, the resin is dried again prior to HF cleavage of the peptide.

Cleavage of the peptide from the MBHA resin with a concomitant removal of the remaining protecting groups is achieved by HF treatment, as described in Examples I-III. Subsequent work-up and HPLC purification, performed as described in Examples I-III, yields 11.6 mg of pure Peptide 67 (>95% purity by analytical HPLC). Molecular mass is checked by electrospray mass spectrometry, and the expected amino acid composition is confirmed by amino acid analysis.

Peptide 30, Peptide 31, Peptide 64, Peptide 68, Peptide 73, Peptide 74, and Peptide 75 are synthesized in the same manner as Peptide 67, except that these peptides also contain other substitutions.

For the synthesis of Peptide 30, the chemical structure of which is
[PhAc-Tyr$^1$, D-Arg$^2$, Phe(pCl)$^6$, Arg$^9$, Amp$^{10}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Amp(Alloc)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 31, the chemical structure of which is
[PhAc-Tyr$^1$, D-Arg$^2$, Phe(pCl)$^6$, Har$^9$, Amp$^{10}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Amp(Alloc)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 64, the chemical structure of which is
[PhAc-Tyr$^1$, D-Arg$^2$, Phe(pCl)$^6$, Har$^9$, Tyr(Me)$^{10}$, Amp$^{11}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Amp(Alloc)-OH, Boc-Tyr(Me)-OH, Boc-Har(NO$_2$)—OH, Boc-Asp-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 68, the chemical structure of which is
[PhAc-Tyr$^{11}$, D-Arg$^2$, Phe(pCl)$^6$, Amp$^9$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg (Tos)-OH, Boc-Tyr(2BrZ)-OH, Boc-Amp(Alloc)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 73, the chemical structure of which is

[PhAc-Tyr$^1$, D-Arg$^2$, Phe(pCl)$^6$, Amp$^9$, Tyr(Me)$^{10}$, His$^{11}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Amp(Alloc)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 74, the chemical structure of which is

[PhAc-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$-Har29]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Amp(Alloc)-OH, Boc-Cit-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 75, the chemical structure of which is

[1-Nac-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2C12)—OH, Boc-His(Bom)-OH, Boc-Tyr(Me)-OH, Boc-Amp(Alloc)-OH, Boc-Cit-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with 1-naphthylacetic acid (1-Nac-OH).

Deprotection, cleavage from the resin, and subsequent purification by semipreparative HPLC of Peptide 30, Peptide 31, Peptide 64, Peptide 68, Peptide 73, Peptide 74, and Peptide 75 are done as described in the case of Peptide 67. The purified compounds are judged to be substantially (>95%) pure by analytical HPLC. Their molecular masses are checked by electrospray mass spectrometry, and the expected amino acid compositions are confirmed by amino acid analysis.

Example V

PhAc-Tyr$^1$-D-Arg$^2$-Asp$^3$-Ala$^4$-Ile$^5$-Phe(pCl)$^6$-Thr$^7$-Asn$^8$-Har$^9$-Tyr(Me)$^{10}$-Arg$^{11}$-Lys$^{12}$-Val$^{13}$-Leu$^{14}$-Abu$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NHEt (Peptide 46)

{[PhAc-Tyr$^1$, D-Arg$^2$, Phe(pCl)$^6$, Har$^9$, Tyr(Me)$^{10}$, Abu$^{15}$, Nle$^{27}$, D-Arg$^{28}$, Har-$^{29}$]hGH-RH(1-29)NHEt}

The synthesis is conducted in a stepwise manner using manual solid phase peptide synthesis equipment. Briefly, Merrifield resin (Bachem, King of Prussia, Pa.) (3.0 g, with a substitution of 0.6 mmol/g) is pre-swollen in DCM, washed 3× times with DMF, then a solution of 2390 mg Boc-Har(Tos)-OH (5.4 mmol, corresponding to 3× molar excess) in 20-30 mL DMF and 314 mg solid KF (5.4 mmol, 3× molar excess) is added, in order to load the first amino acid onto the resin. The resin is shaken with the above mixture for 4 hours at 80° C., and then the resin is filtered and washed as follows: 3×DMF, 3× DMF-water (1:1) (to remove the KF), 3×DMF, 3×DCM, and 3× MeOH. The resin is dried in vacuum for 24 hours to reach a constant weight The weight of the dry resin with the first amino acid loaded [Boc-Har(Tos)-Merrifield resin] exceeds 3.5 g, indicating that the yield of loading is better than 70%.

1.5 g of Boc-Har(Tos)-Merrifield resin (approx. 0.5 mmol) is pre-swollen in DCM, and after deprotection with 50% TFA in DCM and neutralization with 5% DIEA in DCM, the peptide chain is built stepwise by coupling the following protected amino acids in the indicated order on the resin to obtain the desired peptide sequence: Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Har(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH. In this synthesis, Boc-Har(Tos)-OH is used instead of Boc-Har(NO$_2$)—OH, since the nitro protected guanidino group is known to be attacked by bases such as ethylamine used in this synthesis, and partial decomposition of Har to Lys could occur with Boc-Har(NO$_2$)—OH, The protected amino acids (1.5 mmol each) are coupled with DIC (235 µL, 1.5 mmol) with the exceptions of Boc-Asn-OH and Boc-Gln-OH which are coupled with their preformed HOBt esters. After removal of the N$^\alpha$-Boc protecting group from Tyr$^1$, the peptide is acylated with phenylacetic acid (PhAc-OH) (272 mg, 2 mmol) using DIC (313 µL, 2 mmol), washed with DCM and MeOH, and dried.

In order to cleave the protected peptide from the resin by ethylamine (EtNH$_2$) mediated aminolysis and to obtain it with an ethylamide modification (—NHEt) at the C-terminus, a portion of 250 mg dry peptide resin is added into a round-bottom flask made of heavy-wall glass, the flask is placed in a dry ice-methanol cooling bath inside a well-ventilated fume hood, and liquid EtNH$_2$ (b.p.=16.6° C., from Aldrich, shipped in metallic cylinder) is transferred into the flask in an amount sufficient to cover the peptide resin. The flask is stoppered, warmed to room temperature (caution: pressure develops inside), and shaken for 3 hours and 30 min in order to allow for the reaction to take place. After this time, the flask is placed again in the cooling bath, opened, and the liquid EtNH$_2$ is filtered off the solid residue that contains a mixture of resin and cleaved peptide, the peptide still having the protecting groups attached. After this procedure, the solid residue is subjected to vacuum overnight to remove any residual EtNH$_2$ and the humidity adsorbed.

The dry residue containing the cleaved, protected peptide is placed in the HF treatment apparatus and HF cleavage of the protecting groups is performed by treatment with 5 mL HF at 0° C. for 2 hours, in the presence of 0.5 mL m-cresol as scavenger. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 90-110 mg of crude product is typically obtained.

The peptide is purified by. semipreparative HPLC and the eluting fractions are examined by analytical HPLC as described in Examples I-III. Fractions with purity higher than 95% are pooled and lyophilized to give 5 to 10 mg of pure Peptide 46. Molecular mass is checked by electrospray mass spectrometry, and the expected amino acid composition is confirmed-by amino acid analysis.

Peptide 45, Peptide 47, Peptide 48, Peptide 49, Peptide 50, Peptide 56, Peptide 97, Peptide 98, Peptide 99, Peptide 100, Peptide 101, Peptide 106, Peptide 110, Peptide 113, Peptide 114, Peptide 115, Peptide 118, Peptide 119, Peptide 120, and Peptide 121 are synthesized in the same manner as Peptide 46, except that these peptides also contain other substitutions.

For the synthesis of Peptide 45, the chemical structure of which is

[Hca-Tyr$^1$, D-Arg$^2$, Phe(pCl)$^6$, Har$^8$, Tyr(Me)$^{10}$, Abu$^{15}$, Nle$^{27}$, D-Arg$^{28}$, Har$^{29}$]hGH-RH(1-29)NH$_2$, the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Har(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with Hca-OH.

For the synthesis of Peptide 47, the chemical structure of which is

[Hca-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$, the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-ValOH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with Hca-OH.

For the synthesis of Peptide 48, the chemical structure of which is

[PhAc-Tyr$^1$, D-Arg$^2$, Phe(pCl)$^6$, Arg$^8$, Abu$^{15}$, Nle$^{27}$, D-Arg$^{29}$, Har$^{29}$]hGH-RH(1-29)NHEt, the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 49, the chemical structure of which is

[PhAc-Tyr$^1$, D-Arg$^2$, Phe(pCl)$^6$, Har$^9$, Tyr(Me)$^{10}$, Aib$^{15}$, Nle$^{27}$, D-Arg$^{28}$, Har$^{29}$]hGH-RH)1-29)NHEt, the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Aib-OH, Boc-Leu-OH, Boc-Val-OH, Boc-Lys(2ClZ)-OH, Boc-Arg(Tos)-OH, Boc-Tyr(Me)-OH, Boc-Har(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 50, the chemical structure of which is

[PhAc-Tyr$^1$, D-Arg$^2$, Phe(pCl)$^6$, Har$^9$, Tyr(Me)$^{10}$, Orn$^{12}$, Abu$^{15}$, Nle$^{27}$, D-Arg$^{28}$, Har$^{29}$]hGH-Rh(1-29)NHEt, the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(Me)-OH, Boc-Har(Tos)-OH, Boc-Asn-OH, Boc-Thr(Bz)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 56, the chemical structure of which is

[Hca-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, Har$^{30}$]hGH-RH(1-30)NHEt, the following protected amino acids are coupled in the indicated order on the Merrifield resin: Boc-Har(Tos)-OH, Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Har(Tos)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with Hca-OH.

For the synthesis of Peptide 97, the chemical structure of which is

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$ hGH-RH(1-29)NHEt, the following protected-amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His (Bom)-OH, Boc-Tyr(Et)-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6$COOH.

For the synthesis of Peptide 98, the chemical structure of which is

[$CH_3(CH_2)_8CO$-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NHEt the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Et)-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_8$COOH.

For the synthesis of Peptide 99, the chemical structure of which is ($CH_3(CH_2)_{10}CO$-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NHEt, the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Et)-OH, Boc-His(Bom)-OH, Boc-Ala-H, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_{10}$COOH.

For the synthesis of Peptide 100, the chemical structure of which is

[Hca-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NHEt, the following protected amino acids are coupled in the indicated order on the Merrifield resin: Boc-Har(Tos)-OH, Boc-D-Arg(Tos)-OH, Boc-Nle-H, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Et)-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with Hca-OH.

For the synthesis of Peptide 101, the chemical structure of which is

[$CH_3(CH_2)_6CO$-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NHMe, the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH; Boc-Leu-OH, Boc-Val-OH, Boc-Lys(2ClZ)-OH, Boc-His(Bom)-OH, Boc-Tyr(Et)-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6$COOH.

For the synthesis of Peptide 106, the chemical structure of which is

[$CH_3(CH_2)_6CO$-Tyr$^1$, D-Arg$^2$, Phe(pCl)$^6$, Ala$^8$, His$^9$, Tyr(Et)$^{10}$, His$^{11}$, Orn$^{12}$, Abu$^{15}$, His$^{20}$, Nle$^{27}$, D-Arg$^{28}$, Har$^{29}$] hGH-RH(1-29)NHEt, the following protected amino acids are coupled in the indicated order on the Merrifield resin: Boc-Har(Tos)-OH, Boc-D-Arg(Tos)-OH, Boc-Ile-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Et)-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6$COOH.

For the synthesis of Peptide 110, the chemical structure of which is

[$HOOC(CH_2)_{12}CO$-Tyr$^1$, D-Arg$^2$, Phe(pCl)$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt, the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Et)-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $HOOC(CH_2)_{12}$COOH.

For the synthesis of Peptide 113, the chemical structure of which is

[$CH_3(CH_2)_6CO$-Tyr$^1$, D-Arg$^2$, Phe(pCl)$^6$, Ala$^8$, Amp$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt, the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Et)-OH, Boc-Amp-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_8$COOH.

For the synthesis of Peptide 114, the chemical structure of which is

[$CH_3(CH_2)_6CO$-Tyr$^1$, D-Arg$^2$, Phe(pCl)$^6$, Ala$^8$, His$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$] hGH-RH(1-29)NHEt, the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Dip-OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_8COOH$.

For the synthesis of Peptide 115, the chemical structure of which is $[CH_3(CH_2)_6CO\text{-}Tyr^1, D\text{-}Arg^2, Phe(pCl)^6, Ala^8, His^9, Phe(pNO_2)^{10}, His^{11}, Orn^{12}, Abu^{15}, Orn^{21}, Nle^{27}, D\text{-}Arg^{28}, Har^{29}]hGH\text{-}RH(1\text{-}29)NHEt$, the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Phe(pNO$_2$)—OH, Boc-His(Bom)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6COOH$.

For the synthesis of Peptide 118, the chemical structure of which is $[CH_3(CH_2)_6CO\text{-}Tyr^1, D\text{-}Arg^2, Phe(pCl)^6, Ala^8, Amp^9, Dip^{10}, His^{11}, Orn^{12}, Abu^{15}, His^{20}, Orn^{21}, Nle^{27}, D\text{-}Arg^{28}, Har^{29}]hGH\text{-}RH(1\text{-}29)NHEt$, the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Dip-OH, Boc-Amp-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6COOH$.

For the synthesis of Peptide 119, the chemical structure of which is $[CH_3(CH_2)_6CO\text{-}Tyr^1, D\text{-}Arg^2, Phe(pCl)^6, Ala^6, Amp^9, Phe(pNO_2)^{10}, His^{11}, Orn^{12}, Abu^{15}, His^{20}, Orn^{21}, Nle^{27}, D\text{-}Arg^{28}, Har^{29}]hGH\text{-}RH(1\text{-}29)NHEt$, the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Phe(pNO$_2$)—OH, Boc-Amp-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $CH_3(CH_2)_6COOH$.

For the synthesis of Peptide 120, the chemical structure of which it is $[HOOC(CH_2)_{12}CO\text{-}Tyr^1, D\text{-}Arg^2, Phe(pCl)^6, Ala^8, Amp^9, Dip^{10}, His^{11}, Orn^{12}, Abu^{15}, His^{20}, Orn^{21}, Nle^{27}, D\text{-}Arg^{28}, Har^{29}]hGH\text{-}RH(1\text{-}29)NHEt$, the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Dip-OH, Boc-Amp-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $HOOC(CH_2)_{12}COOH$.

For the synthesis of Peptide 121, the chemical structure of which is $[HOOC(CH_2)_{12}CO\text{-}Tyr^1, D\text{-}Arg^2, Phe(pCl)^6, Ala^8, Amp^9, Phe(pNO_2)^{10}, His^{11}, Orn^{12}, Abu^{15}, His^{20}, Orn^{21}\text{-}Nle^{27}, D\text{-}Arg^{28}, Har^{29}]hGH\text{-}RH(1\text{-}29)NHEt$ the following protected amino acids are coupled in the indicated order on the Merrifield resin: Boc-Har(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Phe(pNO$_2$)—OH, Boc-Amp-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with $HOOC(CH_2)_{12}COOH$.

Ethylamine mediated cleavage from the resin of Peptide 45, Peptide 47, Peptide 48, Peptide 49, Peptide 50, Peptide 56, Peptide 97, Peptide 98, Peptide 99, Peptide 100, Peptide 106, Peptide 110, Peptide 113, Peptide 114, Peptide 115, Peptide 118, Peptide 119, Peptide 120, and Peptide 121, as well as methylamine mediated cleavage from the resin of Peptide 101, followed by their deprotection by HF, and subsequent purification by semipreparative HPLC, are done as described in the case of Peptide 46. The purified compounds are judged to be substantially (>95%) pure by analytical HPLC. Their molecular masses are checked by electrospray mass spectrometry, and the expected amino acid compositions are confirmed by amino acid analysis.

Example VI

Hca-Tyr$^1$-D-Arg$^2$-Asp$^3$-Ala$^4$-Ile$^5$-Phe(pCl)$^6$-Thr$^7$-Asn$^8$-Har$_{17}^9$-Tyr(Me)$^{10}$-Arg$^{11}$-Lys$^{12}$-Val$^{13}$-Leu$^{14}$-Abu$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$D-Arg$^{28}$-Har$^{29}$-Agm$^{30}$ Peptide 59

{[Hca-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, Agm$^{30}$]hGH-RH(1-30)}

The synthesis is conducted in a stepwise manner using manual solid phase peptide synthesis equipment The starting material of the synthesis is Boc-agmatine-N$^G$-sulfonyl-phenoxyacetyl-MBHA (Boc-Agm-SPA-MBHA) resin with a substitution of 0.3 mmol/g, which was obtained commercially from California Peptide Research, Inc. (Napa, Calif.). The synthesis of this resin has been described in U.S. Pat. No. 4,914,189 and in the scientific literature (Zarandi M, Serfozo P, Zsigo J, Bokser L, Janaky T, Olsen D B, Bajusz S, Schally A V, Int. J. Peptide Protein Res. 39: 211-217, 1992), hereby incorporated by reference. Briefly, Boc-Agm-SPA-MBHA resin (1.67 g, 0 50 mmol) is pre-swollen in DCM and then the deprotection. and neutralization protocols described in Table I are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH. The protected amino acids (1.5 mmol each) are coupled with DIC (235 μL, 1.5 mmol) with the exceptions of Boc-Asn-OH and Boc-Gln-OH which are coupled with their preformed HOBt esters. After removal of the N$^\alpha$-Boc protecting group from Tyr$^1$, the peptide is acylated with hydrocinnamic acid (Hca-OH) (300 mg, 2 mmol) using DIC (313 μL, 2 mmol).

In order to cleave the peptide from the resin and deprotect it, a portion of 250 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 100-110 mg of crude product is, typically obtained.

The peptide is purified by semipreparative HPLC and the eluting fractions are examined by analytical HPLC as described in Examples I-III. Fractions with purity higher than 95% are pooled and lyophilized to give 5 to 10 mg of pure Peptide 59. Molecular mass is checked by electrospray mass spectrometry, and the expected amino acid composition is confirmed by amino acid analysis.

Peptide 51, Peptide 52, and Peptide 60 are synthesized in the same manner as Peptide 59, except that these peptides also contain other substitutions.

For the synthesis of Peptide 51, the chemical structure of which is

[Hca-Tyr$^1$, D-Arg$^2$, Phe(pCl)$^6$, Har$^9$, Tyr(Me)$^{10}$, Abu$^{15}$, Nle$^{27}$, D-Arg$^{28}$, Agm$^{29}$]hGH-RH(1-29), the following protected amino acids are coupled in the indicated order on the Boc-Agm-SPA-MBHA resin: Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with Hca-OH.

For the synthesis of Peptide 52, the chemical structure of which is

[PhAc-Tyr$^1$, D-Arg$^2$, Phe(pCl)$^6$, Har$^9$, Tyr(Me)$^{10}$, Abu$^{15}$, Nle$^{27}$, D-Arg$^{28}$, Agm$^{29}$]hGH-RH(1-29), the following protected amino acids are coupled in the indicated order on the Boc-Agm-SPA-MBHA resin: Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

For the synthesis of Peptide 60, the chemical structure of which is

[PhAc-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, Agm$^{30}$]hGH-RH(1-30), the following protected amino acids are coupled in the indicated order on the Boc-Agm-SPA-MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-H, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Har(NO$_2$)—OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc-OH.

HF cleavage and deprotection, and subsequent purification by semipreparative HPLC of Peptide 51, Peptide 52, and Peptide 60 are done as described in the case of Peptide 59. The purified compounds are judged to be substantially (>95%) pure by analytical HPLC. Their molecular masses are checked by electrospray mass spectrometry, and the expected amino acid compositions are confirmed by amino acid analysis.

Example VII

CH$_3$(CH$_2$)$_6$CO-Tyr$^1$-D-Arg$^2$-Asp$^3$-Ala$^4$-Ile$^5$-Phe(pCl)$^6$-Thr$_7$-Asn$^8$-Amp$^9$-Tyr(Me)$^{10}$-Arg$^{11}$-Lys$^{12}$-Val$^{13}$-Leu$^{14}$-Abu$_{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$
Peptide 70
{[CH$_3$(CH$_2$)$_6$CO-Tyr$^1$, D-Arg$^2$, Phe(pCl)$^6$, Amp$^9$, Tyr(Me)$^{10}$, Abu$^{11}$, Nle$^{27}$, D-Arg$^{28}$, Har$^{29}$]hGH-RH(1-29)NH$_2$}

All synthetic steps prior to coupling of the N-terminal acyl moiety to the peptide-resin are performed as described in Example IV. After removal of the N$^\alpha$-Boc protecting group from Tyr$^1$, the peptide (0.5 mmol) is acylated overnight with octanoic acid [CH$_3$(CH$_2$)$_6$COOH] (475 μL, 3 m using DIC (235 μL, 1.5 mmol) as a coupling agent. The finished peptidyl resin, with all the side-chain protecting groups still attached, is washed 3× with DCM, 3× with MeOH, and dried under high vacuum.

Subsequently, the peptidyl resin is subjected to Pd(0)-catalyzed removal of the Alloc protecting group from the Amp$^9$ residue of the peptide chain, as described in Example IV. The peptide resin is then washed with MeOH and dried, prior to HF cleavage of the peptide.

Cleavage of the peptide from the MBHA resin with a concomitant removal of the remaining protecting groups is achieved by HF treatment, as described in Examples-I-III. Subsequent work-up and HPLC purification are performed as described in Examples I-III. After HF treatment of 300 mg dry peptidyl resin, 192 mg crude lyophilized peptide is obtained, the HPLC purification of which yields 17.1 mg pure Peptide 70 (>95% purity by analytical HPLC). Molecular mass is checked by electrospray mass spectrometry, and the expected amino acid composition is confirmed by amino acid analysis.

Peptide 76, Peptide 78, Peptide 87, Peptide 103, Peptide 111, and Peptide 112 are synthesized in the same manner as Peptide 70, except that these peptides also contain other substitutions.

For the synthesis of Peptide 76, the chemical structure of which is
[CH$_3$(CH$_2$)$_6$CO-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Amp(Alloc)-OH, Boc-Cit-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with CH$_3$(CH$_2$)$_6$COOH.

For the synthesis of Peptide 78, the chemical structure of which is [CH$_3$(CH$_2$)$_6$CO-Tyr$^1$, D-Arg$^2$, Phe(pCl)$^6$, Cit$^8$, Amp$^9$, Tyr(Et)$^{10}$, His$^{11}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Et)-OH, Boc-Amp(Alloc)-OH, Boc-Cit-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with CH$_3$(CH$_2$)$_6$COOH.

For the synthesis of Peptide 87, the chemical structure of which is
(CH$_3$(CH$_2$)$_6$CO-Tyr$^1$, D-Arg$^2$, Phe(pCl)$^6$, Ala$^8$, Amp$^9$, Tyr(Et)$^{10}$, His$^{11}$, Abu$^{15}$, His$^{20}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Et)-OH, Boc-Amp(Alloc)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with CH$_3$(CH$_2$)$_6$COOH.

For the synthesis of Peptide 103, the chemical structure of which is
[CH$_3$(CH$_2$)$_6$CO-Tyr$^1$, D-Arg$^2$, Phe(pCl)$^6$, Ala$^8$, Amp$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Et)-OH, Boc-Amp(Alloc)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with CH$_3$(CH$_2$)$_6$COOH.

For the synthesis of Peptide 111, the chemical structure of which is
[CH$_3$(CH$_2$)$_6$CO-Tyr$^1$, D-Arg$^2$, Phe(pCl)$^6$, Ala$^8$, Amp$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Dip-OH, Boc-Amp(Alloc)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with CH$_3$(CH$_2$)$_6$COOH.

For the synthesis of Peptide 112, the chemical structure of which is
[CH$_3$(CH$_2$)$_6$CO-Tyr$^1$, D-Arg$^2$, Phe(pCl)$^6$, Ala$^8$, Amp$^9$, Phe(pNO$_2$)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val OH, Boc-Orn(2ClZ)-OH, Boc-His(Bom)-OH, Boc-Phe(pNO$_2$)—OH, Boc-Amp(Alloc)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with CH$_3$(CH$_2$)$_6$COOH.

Deprotection, cleavage from the resin, and subsequent purification by semipreparative HPLC of Peptide 76, Peptide 78, Peptide 87, Peptide 103, Peptide 111, and Peptide 112 are done as described in the case of Peptide 70. The purified compounds are judged to be substantially (>95%) pure by analytical HPLC. Their molecular masses are checked by electrospray mass spectrometry, and the expected amino acid compositions are confirmed by amino acid analysis.

Example VIII

HOOC(CH$_2$)$_{12}$CO-Tyr$^1$-D-Arg$^2$-Asp$^3$-Ala$^4$-Ile$^5$-Phe(pCl)$^6$-Thr$^7$-Asn$^8$-Amp$^9$-Tyr(Me)$^{10}$-Arg$^{11}$-Lys$^{12}$-Val$^{13}$-Leu$^{14}$-Abu$_{15}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 72 {[HOOC(CH$_2$)$_{12}$CO-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$}

All synthetic steps prior to coupling of the N-terminal acyl moiety to the peptide-resin are performed as described in Example IV. After removal of the N$^\alpha$-Boc protecting group from Tyr$^1$, the peptide is acylated with the pre-formed symmetrical anhydride of 1,12-dodecanedicarboxylic acid which is prepared as follows. For synthesis on the scale of 0.5 mmol peptide, 388 mg (1.5 mmol) 1,12-dodecanedicarboxylic acid [HOOC(CH$_2$)$_{12}$COOH] is dissolved in 5 to 10 mL of DMF-DCM (1:1), 235 µL (1.5 mmol) DIC is added to this solution, and the mixture is allowed to stand at room temperature for 30 min. After this period of time, the mixture is transferred into the synthesis vessel containing the peptide-resin with a free amino terminus on Tyr$^1$, and acylation is carried out overnight. The finished peptidyl resin, with all the sidechain protecting groups still attached, is washed 3× with DCM, 3× with MeOH, and dried under high vacuum.

Subsequently, the peptidyl resin is subjected to Pd(0)catalyzed removal of the Alloc protecting group from the Amp$^9$ residue of the peptide chain, as described in Example IV. The peptide resin is then washed with MeOH and dried, prior to HF cleavage of the peptide.

Cleavage of the peptide from the MBHA resin with a concomitant removal of the remaining protecting groups is achieved by HF treatment, as described in Examples I-III. Subsequent work-up and HPLC purification are performed as described in Examples I-III. After HF treatment of 150 mg dry peptidyl resin, 82 mg crude lyophilized peptide is obtained, the HPLC purification of which yields 2.5 mg pure Peptide 72 (>95% purity by analytical HPLC). Molecular mass is checked by electrospray mass spectrometry, and the expected amino acid composition is confirmed by amino acid analysis.

Peptide 71, Peptide 77, Peptide 89, Peptide 107, Peptide 116, and Peptide 117 are synthesized in the same manner as Peptide 72, except that these peptides also contain other substitutions.

For the synthesis of Peptide 71, the chemical structure of which is

[HOOC(CH$_2$)$_8$CO-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Amp(Alloc)-OH, Boc-Asn-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with HOOC(CH$_2$)$_8$COOH.

For the synthesis of Peptide 77, the chemical structure of which is

[HOOC(CH$_2$)$_{12}$CO-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Amp(Alloc)-OH, Boc-Cit-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with HOOC(CH$_2$)$_{12}$COOH.

For the synthesis of Peptide 89, the chemical structure of which is

[HOOC(CH$_2$)$_{12}$CO-Tyr$^1$, D-Arg$^2$, Phe(pCl)$^6$, Ala$^8$, Amp$^9$, Tyr(Et)$^{10}$, His$^{11}$, Abu$^{15}$, His$^{20}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Et)-OH, Boc-Amp(Alloc)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with HOOC(CH$_2$)$_{12}$COOH.

For the synthesis of Peptide 107, the chemical structure of which is

[HOOC(CH$_2$)$_{12}$CO-Tyr$^1$, D-Arg$^2$, Phe(pCl)$^6$, Ala$^8$, Amp$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Et)OH, Boc-Amp(Alloc)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with HOOC(CH$_2$)$_{12}$COOH.

For the synthesis of Peptide 116, the chemical structure of which is

[HOOC(CH$_2$)$_{12}$CO-Tyr$^1$, D-Arg$^2$, Phe(pCl)$^6$, Ala$^8$, Amp$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Dip-OH, Boc-Amp(Alloc)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with HOOC(CH$_2$)$_{12}$COOH.

For the synthesis of Peptide 117, the chemical structure of which is

[HOOC(CH$_2$)$_{12}$CO-Tyr$^1$, D-Arg$^2$, Phe(pCl)$^6$, Ala$^8$, Amp$^9$, Phe(pNO$_2$)$^{10}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Phe(pNO$_2$)—OH, Boc-Amp(Alloc)-OH, Boc-Ala-OH, Boc-Thr(Bzl)-OH, Boc-Phe(pCl)—OH, Boc-Ile-OH, Boc-Ala-OH, Boc-Asp(OcHx)-OH, Boc-D-Arg(Tos)-OH, Boc-Tyr(2BrZ)-OH, followed by acylation with HOOC(CH$_2$)$_{12}$COOH.

Deprotection, cleavage from the resin, and subsequent purification by semipreparative HPLC of Peptide 71, Peptide 77, Peptide 89, Peptide 107, Peptide 116, and Peptide 117 are done as described in the case of Peptide 72. The purified compounds are judged to be substantially (>95%) pure by analytical HPLC. Their molecular masses are checked by electrospray mass spectrometry, and the expected amino acid compositions are confirmed by amino acid analysis.

Example IX

Aqueous Solution for Intramuscular Injection

| | |
|---|---|
| [PhAc-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ (Peptide 67) | 500.0 mg |
| Gelatin, nonantigenic | 5.0 mg |
| Water for injection q.s. | ad 100.0 mL |

The gelatin and GH-RH antagonist Peptide 67 are dissolved in water for injection, then the solution is sterile filtered.

Example X

Lonq Acting Intramuscular Injectable Formulation (Sesame Oil Gel)

| | |
|---|---|
| [CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NH$_2$ (Peptide 80) | 10.0 mg |
| Aluminum monostearate, USP | 20.0 mg |
| Sesame oil q.s. | ad 1.0 mL |

The aluminum monostearate is combined with the sesame oil and heated to 125° C. with stirring until a dear yellow solution forms. This mixture is then autoclaved for sterility and allowed to cool. The GH-RH antagonist Peptide 80 is then added aseptically with trituration. Particularly preferred antagonists are salts of low solubility, e.g., pamoate salts and the like. These exhibit long duration of activity.

Example XI

Lone Acting Intramuscular (1M) Injectable-Biodegradable Polymer Microcapsules

Microcapsules are Made from the Following:

| | |
|---|---|
| 25/75 glycolide/lactide copolymer (0.5 intrinsic viscosity) | 99% |
| [CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ (Peptide 96) | 1% |

25 mg of the above microcapsules are suspended in 1.0 mL of the following vehicle:

| | |
|---|---|
| Dextrose | 5.0% |
| CMC, sodium | 0.5% |
| Benzyl alcohol | 0.9% |
| Tween 80 | 0.1% |
| Water, purified q.s. | ad 100% |

Example XII

Biological Activity in Endocrine and Oncolocical Assays

The peptides of the present invention were tested in assays in vitro and in vivo for their ability to inhibit the hGH-RH(1-29)NH$_2$ induced GH release. Binding affinities of the compounds to the tumoral GH-RH receptors were also measured. The antitumor activities of the peptides and their inhibitory effects on serum IGF-I and on the tumoral IGF system were evaluated in various cancer models in vivo.

Superfused Rat Pituitary System

The analogs were tested in vitro in a test described earlier (S. Vigh and A. V Schally, Peptides 5:241-347, 1984) with modification (Z. Rekasi and A. V. Schally, P.N.A.S. 90:2146-2149, 1993).

Briefly, the cells are preincubated with peptides for 9 minutes (3 mL) at various concentrations. Immediately after the incubation, 1 nM hGH-RH(1-29)NH$_2$ is administered for 3 minutes (1 mL) 10 minute response). To check the duration of the antagonistic effect of the analogue, 1 nM hGH-RH(1-29)NH$_2$ is applied 30, 60, 90, and 120 minutes later for 3 minutes [30, 60, 90, 120 min responses]. Net integral values of the GH responses are evaluated. GH responses are compared to and expressed as percent of the original GH response induced by 1 nM GH-RH(1-29)NH$_2$ The effect of the new antagonists are compared to that of [Ac-Tyr$^1$, D-Arg$^2$]hGH-RH(1-29)NH$_2$, the "Standard antagonist".

Radioimmunoassays (RIA) for GH, IGF-I, and IGF-II

Rat GH levels in aliquots of undiluted and diluted superfusion samples were measured by double-antibody radioimmunoassay using materials supplied by the National Hormone and Pituitary Program, Baltimore, Md. The results of RIA were analyzed with a computer program developed in our institute (V. Csernus and A. V. Schally, in Neuroendocrine Research Methods, Harwood Academic (Greenstein, B. D. ed., London, pp. 71-109, 1991), hereby incorporated by reference.

For the measurement of GH and IGF-I levels in the serum, as well as IGF-I and IGF-II concentrations in the cytosol fraction of tumors, blood samples and tumor samples were collected and processed as described (Braczkowski R, Schally A V, Plonowski A, Varga J L, Groot K, Krupa M, Armatis P, Cancer 95: 1735-1745, 2002), hereby incorporated by reference. Briefly, blood samples are centrifuged to separate the serum, tumors are homogenized and centrifuged to separate the cytosol fraction. Serum GH is then measured by the double-antibody RIA method. Before measurement by RIA, IGF-I and IGF-II are extracted from serum and cytosol fractions using an acid-ethanol cryoprecipitation method that eliminates most of the IGF binding proteins, which can interfere with the RIA. IGF-I concentration is measured by RIA using IGF-I as a standard and goat anti-IGF-I antibody (both from DSL Inc., Webster, Tex.). IGF-II concentration is measured by RIA using human recombinant IGF-II (Bachem) as a standard and anti-IGF-II monoclonal antibody (Amano International Enzyme, Troy, Va.).

In all RIA measurements, inter-assay variation was less than 15% and intra-assay variation was less than 10%.

Tumoral GH-RH Receptor Binding Assay

Ligand competition assays with $^{125}$I-labeled GH-RH antagonist JV-1-42 were used to determine the binding affinities of GH-RH analogs to the GH-RH receptor isoforms on membrane fractions of human PC-3 prostate tumors. The methods used have been described in detail (Halmos G, Schally A V, Varga J L, Plonowski A, Rekasi Z, Czompoly T, Proc Natl Acad Sci USA 97: 10555-10560, 2000; Halmos G, Schally A V, Czompoly T, Krupa M, Varga J L, Rekasi Z, J Clin Endocrinol Metab 87: 4707-4714, 2002), hereby incorporated by reference. Briefly, radioiodinated derivatives of JV-142 are prepared by the chloramine-T method. PC-3 tumors, grown as xenografts in nude mice, are used to prepare crude membranes. PC-3 membrane homogenates are incubated with [$^{125}$I]JV-142 and increasing concentrations ($10^{-12}$ to $10^{-6}$ M) of nonradioactive antagonist peptides as competitors. The pellet is separated by centrifugation and counted for radioactivity in a gamma-counter. The final binding affinities are estimated by $K_1$ (dissociation constant of the inhibitor-receptor complex) and are determined by the Ligand PC and McPherson computer programs of Munson and Rodbard (P. J. Munson and D. Rodbard, Anal. Biochem. 167: 220-239, 1980). Relative affinities (R.A.) compared to reference peptides such as JV-1-36 or JV-1-38, are calculated as the ratio of $K_1$ of the reference peptide to the K, of the tested GH-RH antagonist.

Results of Superfusion Assays

The results of the in vitro antagonistic activities tested in superfused rat pituitary system are summarized in Table III. As it can be seen from these data, the substitutions present in the molecules cause a much increased and protracted inhibitory effect on the GH-RH-elicited GH release in vitro, as compared to the standard antagonist.

TABLE III

Inhibition of GH Release in Superfused Rat Pituitary System

| Antagonist | Dose (nM) | GH response (% of control) | | | | |
|---|---|---|---|---|---|---|
| | | 0 min | 30 min | 60 min | 90 min | 120 min |
| Standard antagonist: | 100 | 38 | 98 | 81 | | |
| JV-1-36* | 30 | 36 | 21 | 25 | 29 | 29 |
| | 10 | 80 | 42 | 60 | 64 | 85 |
| JV-1-38* | 30 | 59 | 32 | 28 | 34 | 31 |
| Peptide 2 | 30 | 18 | 13 | 18 | 25 | 51 |
| Peptide 3 | 30 | 52 | 61 | 56 | 70 | 149 |
| Peptide 4 | 30 | 5 | 0 | 12 | 8 | 18 |
| Peptide 5 | 30 | 22 | 20 | 23 | 27 | 27 |
| Peptide 6 | 30 | 56 | 22 | 12 | 15 | 19 |
| Peptide 7 | 30 | 23 | 13 | 11 | 14 | 14 |
| Peptide 8 | 30 | 37 | 31 | 48 | 44 | 40 |
| Peptide 9 | 30 | 47 | 43 | 66 | 63 | 58 |
| Peptide 10 | 30 | 60 | 30 | 36 | 37 | 44 |
| Peptide 11 | 30 | 14 | 24 | 29 | 34 | 32 |
| Peptide 12 | 30 | 35 | 30 | 35 | 51 | 43 |
| Peptide 13 | 30 | 87 | 77 | 76 | 71 | 73 |
| Peptide 15 | 30 | 28 | 13 | 11 | 36 | 21 |
| Peptide 16 | 30 | 40 | 62 | 78 | 73 | 61 |
| Peptide 17 | 30 | 29 | 51 | 68 | 73 | 61 |
| Peptide 18 | 30 | 21 | 71 | 61 | 75 | 63 |
| Peptide 19 | 30 | 62 | 64 | 66 | 82 | 74 |
| Peptide 21 | 30 | 0 | 13 | 33 | 43 | 37 |
| Peptide 22 | 30 | 22 | 26 | 27 | 45 | N/A |
| Peptide 23 | 30 | 55 | 40 | 41 | 47 | 41 |
| Peptide 24 | 30 | 56 | 13 | 18 | 34 | 60 |
| Peptide 26 | 30 | 20 | 43 | 66 | 48 | 44 |
| Peptide 27 | 30 | 19 | 15 | 23 | 23 | 61 |
| Peptide 28 | 30 | 68 | 7 | 8 | 20 | 34 |
| Peptide 30 | 30 | 18 | 11 | 7 | 7 | 8 |
| Peptide 30 | 10 | 60 | 24 | 34 | 32 | 53 |
| Peptide 31 | 30 | 7 | 1 | 2 | 4 | 3 |
| Peptide 31 | 10 | 57 | 31 | 37 | 36 | 37 |
| Peptide 32 | 30 | 28 | 43 | 69 | 76 | N/A |
| Peptide 33 | 30 | 97 | 89 | 78 | 97 | 82 |
| Peptide 35 | 30 | 91 | 57 | 80 | 66 | 72 |
| Peptide 36 | 30 | 104 | 90 | 112 | 97 | 120 |
| Peptide 37 | 30 | 33 | 12 | 15 | 15 | 19 |
| Peptide 39 | 30 | 63 | 54 | 36 | 37 | 36 |
| Peptide 40 | 30 | 42 | 29 | 26 | 36 | 30 |
| Peptide 41 | 30 | 47 | 16 | 14 | 15 | 16 |
| Peptide 42 | 30 | 52 | 7 | 9 | 8 | 13 |
| Peptide 43 | 30 | 82 | 74 | 102 | 72 | 51 |
| Peptide 45 | 30 | 91 | 100 | 100 | 100 | 99 |
| Peptide 45 | 30 | 100 | 100 | 100 | N/A | N/A |
| Peptide 46 | 30 | 91 | 28 | 31 | 56 | 30 |
| Peptide 48 | 30 | 22 | 21 | 44 | 44 | 47 |
| Peptide 49 | 30 | 83 | 76 | 90 | 87 | 120 |
| Peptide 50 | 30 | 57 | 65 | 69 | 74 | 67 |
| Peptide 51 | 30 | 64 | 36 | 31 | N/A | N/A |
| Peptide 51 | 30 | 52 | 43 | 57 | 56 | 58 |
| Peptide 51 | 30 | 87 | 35 | 46 | 51 | 61 |
| Peptide 52 | 30 | 86 | 13 | 45 | 26 | 55 |
| Peptide 53 | 30 | 43 | 42 | 40 | 36 | 46 |
| Peptide 55 | 30 | 93 | 63 | 96 | 61 | 93 |
| Peptide 56 | 30 | 76 | 83 | 92 | 80 | 68 |
| Peptide 58 | 30 | 78 | 53 | 56 | 47 | N/A |
| Peptide 58 | 30 | 94 | 53 | 57 | 64 | 64 |
| Peptide 58 | 30 | 64 | 41 | 59 | 50 | 69 |
| Peptide 59 | 30 | 72 | 49 | 46 | 38 | N/A |
| Peptide 59 | 30 | 61 | 50 | 48 | 47 | N/A |
| Peptide 59 | 30 | 93 | 43 | 60 | 57 | 76 |
| Peptide 59 | 30 | 47 | 27 | 37 | 44 | 47 |
| Peptide 60 | 30 | 73 | 27 | 34 | 56 | 42 |
| Peptide 60 | 30 | 87 | 29 | 65 | 36 | 63 |
| Peptide 62 | 30 | 20 | 16 | 14 | 21 | 21 |
| Peptide 63 | 30 | 53 | 47 | 49 | 51 | N/A |
| Peptide 64 | 30 | 59 | 54 | 70 | 50 | 56 |
| Peptide 65 | 30 | 67 | 80 | 89 | 97 | 79 |
| Peptide 67 | 30 | 28 | 15 | 18 | 20 | 23 |
| Peptide 68 | 30 | 37 | 22 | 33 | 29 | 33 |
| Peptide 69 | 30 | 9 | 12 | 18 | 18 | 25 |

*reference compounds, subject to U.S. Pat. No. 6,057,422

Results of Tumoral GH-RH Receptor Binding Assay

As seen in Table IV and Table V, respectively, the substitutions present in the molecules cause a substantial increase in their binding affinities to the GH-RH receptor isoforms on PC-3 tumor membranes, as compared to the binding affinities of the reference compounds.

TABLE IV

Relative Affinities (R.A.) of GH-RH Antagonists to Membrane Receptors on PC-3 Human Prostate Cancers

| Peptide | R.A. |
|---|---|
| JV-1-36* | 1 |
| Peptide 11 | 1.3 |
| Peptide 6 | 0.6 |
| Peptide 7 | 12 |
| Peptide 4 | 53 |
| Peptide 5 | 4 |
| Peptide 22 | 10 |
| Peptide 43 | 0.09 |

*reference compound, subject to U.S. Pat. No. 6,057,422

TABLE V

Relative Affinities (R.A.) of GH-RH Antagonists to Membrane Receptors on PC-3 Human Prostate Cancers

| Peptide | R.A. |
|---|---|
| JV-1-38* | 1 |
| Peptide 31 | 0.2 |
| Peptide 36 | 11 |

TABLE V-continued

Relative Affinities (R.A.) of GH-RH Antagonists to Membrane Receptors on PC-3 Human Prostate Cancers

| Peptide | R.A. |
|---|---|
| Peptide 41 | 5 |
| Peptide 42 | 0.6 |
| Peptide 62 | 62 |
| Peptide 67 | 71 |
| Peptide 69 | 59 |

*reference compound, subject to U.S. Pat. No. 6,057,422

Effect of GH-RH Antagonists on PC-3 Human Prostate Cancer Xenografts in Nude Mice Experiment 1:

Male nude mice were implanted s.c. with 3 mm³ pieces of PC-3 human hormone-independent prostate cancer tissue on both flanks. When tumors reached a volume of approx. 50 mm³, the mice were divided into 5 experimental groups with 7 to 8 animals in each group and received single daily injections for 28 days as follows: 1. Control (vehicle solution); 2. JV-1-38 (10 µg/day s.c.); 3 Peptide 31 (10 µg/day s.c.); 4. Peptide 67 (10 µg/day s.c.); 5. Peptide 62 (10 µg/day s.c.). Tumor volumes were measured twice a week. The experiment was ended on day 29 by sacrificing the mice under Isoflurane anesthesia. Resulting tumors were cleaned, weighed, and snap-frozen until further analyses. Trunk blood was collected from the abdominal aorta and serum was separated for RIA measurement of IGF-I. Statistical analyses of the measurement results were done by two-tailed t-test; data are presented as the means±S.E.

Experiment 2:

Experiment 2 was similar to Experiment 1, with the difference that Experiment 2 was started when PC-3 tumors had grown to approximately 30 mm³ in volume. At this time, the animals were divided into 8 experimental groups with 8 animals in each group, and received single daily injections for 28 days as follows. 1. Control (vehicle solution); 2. JV-1-38 (10 µg/day s.c.); 3. Peptide 46 (5 µg/day: s.c.); 4. Peptide 77 (5 µg/day s.c); 5. Peptide 76 (5 µg/day s.c.); 6. Peptide 70 (5 µg/day s.c.); 7 Peptide 79 (5 µg/day s.c.); 8. Peptide 80 (5 µg/day s.c.). Further details of Experiment 2 are the same as for Experiment 1.

Experiment 3:

Male nude mice were implanted s.c. with 3 mm³ pieces of PC-3 human hormone-independent prostate cancer tissue on both flanks. When tumors reached a volume of approximately 65 mm³, the mice were divided into 7 experimental groups with 8 to 9 animals in each group and received single daily injections for 28 days as follows: 1. Control (vehicle solution); 2. JV-1-38 (10 µg/day s.c.); 3. Peptide 35 (10 µg/day s.c.); 4. Peptide 36 (10 µg/day s.c.); 5. Peptide 37 (10 µd/day s.c.); 6. Peptide 39 (10 µg/day s.c.); 7. Peptide 41 (10 µg/day s.c.). Tumor volumes were measured twice a week. The experiment was ended on day 28 by sacrificing the mice under Isofurane anesthesia. Resulting tumors were cleaned, weighed, and snapfrozen until further analyses. Trunk blood was collected from the abdominal aorta and serum was separated for RIA measurement of IGF-I. Statistical analyses of the measurement results were done by ANOVA followed by Fisher test; data are presented as the means±S.E.

Experiment 4:

All experimental details of Experiment 4 are the same as for Experiment 3, with the following difference. When tumors reached a volume of approximately 55 mm³, the mice were divided into 5 experimental groups with 8 to 9 animals in each group and received single daily injections for 28 days as follows: 1. Control (vehicle solution); 2. Peptide 80 (5 µg/day s.c.); 3. Peptide 86 (5 µg/day s.c.); 4. Peptide 95 (5 µg/day s.c.); 5. Peptide 96 (5 µg/day s.c.). Further details of Experiment 4 are the same as for Experiment 3.

Results

Experiment 1:

Among the GH-RH antagonists tested, Peptide 67 and Peptide 62 exerted a stronger inhibitory effect on the growth of PC-3 tumors than the reference peptide JV-1-38 (Table VI). The peptides of the present invention also more potently suppressed IGF-I levels in the serum and IGF-II levels in the tumors, as compared to JV-1-38 (Table VII).

TABLE VI

Experiment 1: Effect of Treatment with GH-RH Antagonists on PC-3 Human Prostate Cancer Xenografts in Nude Mice

| | Tumor volume (mm³) | | Tumor weight (mg) (% inhibition) | Tumor volume doubling time (days) |
|---|---|---|---|---|
| Group | Initial | Final (% inhibition) | | |
| Control | 50.0 ± 7.86 | 501 ± 111 | 378 ± 84.0 | 8.97 ± 0.71 |
| JV-1-38 | 49.2 ± 8.37 | 291 ± 80.4 (42%) | 239 ± 58.0 (37%) | 12.3 ± 1.04* |
| Peptide 31 | 49.1 ± 12.5 | 363 ± 92.8 (28%) | 237 ± 53.3 (37%) | 14.0 ± 2.69 |
| Peptide 67 | 46.8 ± 8.11 | 200 ± 39.5* (60%) | 150 ± 22.1* (60%) | 17.0 ± 3.51* |
| Peptide 62 | 56.1 ± 18.2 | 215 ± 50.4 (57%) | 199 ± 51 7 (47%) | 18.4 ± 4.96* |

*$p < 0.05$ vs. control.

TABLE VII

Experiment 1: Effect of Treatment with GH-RH Antagonists on the Serum Levels of IGF-I and the Tumor Concentrations of IGF-II in Nude Mice Bearing Xenografts of PC-3 Human Prostate Cancer

| Group | Serum IGF-I (ng/mL) (% inhibition) | Tumor IGF-II (pg/mg protein) (% inhibition) |
|---|---|---|
| Control | 149 ± 10.4 | 219 ± 64.7 |
| JV-1-38 | 147 ± 8.49 (1%) | 208 ± 43.3 (5%) |
| Peptide 31 | 133 ± 16.7 (11%) | 130 ± 56.0 (41%) |
| Peptide 67 | 128 ± 10.6 (14%) | 139 ± 69.2 (37%) |
| Peptide 62 | 141 ± 8.86 (5%) | N.I. |

N.I., not investigated.

Experiment 2:

Peptide 46, Peptide 77, Peptide 76, Peptide 70, Peptide 79, and Peptide 80 of the present invention, used at a dose of 5 µg/day, decreased the tumor volumes and tumor weights of PC-3 cancers by 20-64%, and increased the tumor volume doubling times by up to 101% of the control value (Table VIII). The effects of Peptide 77, Peptide 70, Peptide 79, and Peptide 80 were statistically significant on one or more of these tumor parameters. In contrast, reference peptide JV-1-38, subject to U.S. Pat. No. 6,057,422, did not decrease the tumor volume, and only caused a slight and non-significant inhibition of 10% in the weight of PC-3 tumors, when used at a double dose of 10 μg/day (Table VIII). In addition, Peptide 70, Peptide 79, and Peptide 80 of the present invention significantly decreased serum IGF-I levels by 31%-42%, but peptide JV-1-38 had no effect (Table IX).

TABLE VIII

Experiment 2: Effect of Treatment with GH-RH Antagonists on PC-3 Human Prostate Cancer Xenografts in Nude Mice

| Group | Tumor volume (mm³) Initial | Tumor volume (mm³) Final (% inhibition) | Tumor weight (mg) (% inhibition) | Tumor volume doubling time (days) |
|---|---|---|---|---|
| Control | 28.4 ± 4.2 | 351 ± 84.9 | 283 ± 72.1 | 8.3 ± 0.7 |
| JV-1-38 | 29.3 ± 3.8 | 351 ± 72.9 (0%) | 254 ± 52.0 (10%) | 8.7 ± 0.7 |
| Peptide 46 | 26.6 ± 2.7 | 246 ± 93.7 (30%) | 188 ± 66.1 (34%) | 11.2 ± 1.3 |
| Peptide 77 | 27.2 ± 3.2 | 192 ± 44.1 (45%) | 138 ± 34.3 (51%) | 10.7 ± 0.8* |
| Peptide 76 | 26.8 ± 3.4 | 232 ± 30.8 (34%) | 226 ± 48.3 (20%) | 9.4 ± 0.6 |
| Peptide 70 | 26.5 ± 3.7 | 199 ± 40.4*# (43%) | 119 ± 25.3*# (58%) | 12.6 ± 2.5 |
| Peptide 79 | 29.1 ± 4.3 | 139 ± 49.4*# (60%) | 153 ± 54.5 (46%) | 13.6 ± 1.8*# |
| Peptide 80 | 24.8 ± 2.2 | 128 ± 38.9*# (64%) | 137 ± 46.1* (52%) | 16.7 ± 4.3*# |

*p < 0.05 vs. control;
p < 0.05 vs. JV-1-38.

TABLE IX

Experiment 2: Effect of Treatment with GH-RH Antagonists on the Serum Levels of IGF-I in Nude Mice Bearing Xenografts of PC-3 Human Prostate Cancer

| Group | Serum IGF-I (ng/mL) | (% inhibition) |
|---|---|---|
| Control | 262 ± 18.1 | |
| JV-1-38 | 293 ± 28.0 | 0% |
| Peptide 46 | 288 ± 17.9 | 0% |
| Peptide 77 | 276 ± 16.8 | 0% |
| Peptide 76 | 260 ± 29.7 | 1% |
| Peptide 70 | 175 ± 12.9*** | 33% |
| Peptide 79 | 181 ± 19.8** | 31% |
| Peptide 80 | 152 ± 7.83*** | 42% |

**p < 0.01 vs. control;
***p < 0.001 vs. control.

Experiment 3:

All peptides tested significantly inhibited the growth of PC-3 tumors at the dose of 10 μg/day. Peptide 35, Peptide 36, and Peptide 39 had more potent antitumor effect than reference peptide JV-1-38 (Table X).

TABLE X

Experiment 3: Effect of Treatment with GH-RH Antagonists on PC-3 Human Prostate Cancer Xenografts in Nude Mice

| Group | Tumor volume (mm³) Initial | Tumor volume (mm³) Final (% inhibition) | Tumor weight (mg) (% inhibition) | Tumor volume doubling time (days) |
|---|---|---|---|---|
| Control | 71.1 ± 10.5 | 678 ± 172 | 700 ± 152 | 10.6 ± 0.96 |
| JV-1-38 | 68.3 ± 8.08 | 276 ± 48.7** (66%) | 386 ± 62.9* (45%) | 18.2 ± 1.84 |
| Peptide 35 | 65.7 ± 11.3 | 261 ± 52.9** (68%) | 286 ± 58.9* (59%) | 17.0 ± 2.32 |
| Peptide 36 | 68.0 ± 11.7 | 214 ± 72.6** (76%) | 361 ± 89.6* (48%) | 18.7 ± 3.83 |
| Peptide 37 | 60.0 ± 13.0 | 323 ± 68.0* (57%) | 440 ± 104 (37%) | 12.7 ± 2.03 |
| Peptide 39 | 66.7 ± 11.2 | 271 ± 109** (66%) | 247 ± 55.4* (65%) | 19.6 ± 2.10 |
| Peptide 41 | 66.7 ± 12.5 | 341 ± 107* (54%) | 579 ± 188 (17%) | 28.2 ± 9.85 |

*p < 0.05 vs. control; ** p < 0.01 vs. control.

Experiment 4:

All four peptides, administered at a dose of 5 μg/day, significantly inhibited the growth of PC-3 tumors in nude mice. Peptide 96 had the strongest antitumor effect in this experiment (Table XI). Serum IGF-I levels were also inhibited in all groups treated with antagonists, the effects of Peptide 86 and Peptide 96 being statistically significant (Table XII).

TABLE XI

Experiment 4: Effect of Treatment with GH-RH Antagonists on PC-3 Human Prostate Cancer Xenografts in Nude Mice

| Group | Tumor volume (mm³) Initial | Tumor volume (mm³) Final (% inhibition) | Tumor weight (mg) (% inhibition) | Tumor volume doubling time (days) |
|---|---|---|---|---|
| Control | 56.3 ± 10.8 | 1137 ± 351 | 1451 ± 343 | 7.3 ± 0.52 |
| Peptide 80 | 53.2 ± 10.1 | 398 ± 68.7* 68% | 752 ± 150* 48% | 10.7 ± 1.28* |
| Peptide 86 | 56.1 ± 8.67 | 397 ± 71.8* 68% | 643 ± 94.9** 56% | 12.1 ± 1.40** |
| Peptide 95 | 60.9 ± 12.2 | 393 ± 79.8* 69% | 666 ± 131* 54% | 12.5 ± 1.80* |
| Peptide 96 | 56.2 ± 13.3 | 301 ± 65.2** 77% | 489 ± 114** 66% | 11.0 ± 0.87** |

*p < 0.05 vs. control;
**p < 0.01 vs. control.

TABLE XII

Experiment 4: Effect of Treatment with GH-RH Antagonists on the Serum Levels of IGF-I in Nude Mice Bearing Xenografts of PC-3 Human Prostate Cancer

| Group | Serum IGF-I (ng/mL) | (% inhibition) |
|---|---|---|
| Control | 165 ± 10.2 | |
| Peptide 80 | 136 ± 15.3 | 18% |
| Peptide 86 | 118 ± 8.94* | 28% |
| Peptide 95 | 127 ± 17.5 | 23% |
| Peptide 96 | 114 ± 15.5* | 31% |

*p < 0.05 vs. control.

Effect of GH-RH Antagonist on HT-29 Human Colon Cancer Xenografts in Nude Mice

HT-29 human colon cancers were transplanted sc. into male nude mice. 19 days after transplantation, the mice were divided into two groups of 10 animals each. and the treatment was started. Mice in the treatment group received single daily injections of Peptide 67 sc. at a dose of 10 μg/day for 62 days, while the control group was injected with the vehicle solvent. Tumors were measured regularly, and tumor volume was calculated. The mice were sacrificed at the end of experiment and tumor weights were measured.

Results

Treatment with Peptide 67 for 62 days caused a significant inhibition of 56.3% in the volumes and 53.9% in the weights of HT-29 tumors growing in nude mice, as compared to the control group (Table XIII).

TABLE XIII

Effect of Treatment with GH-RH Antagonist Peptide 67 on HT-29 Human Colon Cancer Xenografts in Nude Mice

| Group | Final tumor volume (mm³) | Tumor weight (mg) |
|---|---|---|
| Control | 2792 ± 643 | 3112 ± 543 |
| Peptide 67 | 1218 ± 320* | 1434 ± 405* |

*p < 0.05 vs. control

Effect of GH-RH Antagonists on DMS-153 Human Small Cell Lung Carcinomas (SCLC) Xenografted into Nude Mice Male nude mice were implanted s.c. with 3 mm³ pieces of DMS-153 human SCLC tissue. When tumors reached a volume of approx. 100 mm³ the mice were divided into 3 experimental groups of 68 animals each and received the following treatment for 6 weeks group 1 (control), vehicle solution; group 2, Peptide 67 (10 μg/day s.c.); group 3, Peptide 31 (10 μg/day s.c.). Tumor volumes were recorded twice a week. At the end of treatment, mice were anesthetized with isoflurane, killed by decapitation, trunk blood was collected for measurement of serum IGF-I, and tumors were excised and weighed. Data are presented as means±S.E. Data were evaluated by one way ANOVA and the Student-Newman-Keuls test.

Results

Tumor weights were significantly :decreased in animals that received treatment with either GH-RH antagonist, Peptide 67 or Peptide 31, as compared to controls (Table XIV). Tumor volumes were also significantly smaller in the group that received Peptide 67. In addition, both antagonists significantly reduced the serum levels of IGF-I as compared to those in the control animals (Table XIV). The expression of mRNA for IGF-II was likewise inhibited by both antagonists, the level of expression being 100±1.5% in the control group, 78.0±44.3% in the group treated with Peptide 67, and 42.7±18.5% in the group that received Peptide 31. The inhibitory effect of Peptide 31 on the IGF-II mRNA expression was statistically significant (p<0.01 vs. control).

TABLE XIV

Effect of Treatment with GH-RH Antagonists on DMS-153 Human SCLC Xenografts in Nude Mice and on the Serum IGF-I Levels

| Group | Tumor Weight (g) (% inhibition) | Tumor volume (mm³) Initial | Tumor volume (mm³) Final (% inhibition) | Serum IGF-I (ng/mL) (% inhibition) |
|---|---|---|---|---|
| Control | 2.31 ± 0.25 | 112 ± 13 | 3641 ± 431 | 169.0 ± 9.9 |
| Peptide 67 | 1.60 ± 0.19* (31%) | 132 ± 24 | 2650 ± 30* (28%) | 117.9 ± 17.2* (30%) |
| Peptide 31 | 1.58 ± 0.11* (32%) | 138 ± 20 | 3329 ± 180 (10%) | 118.4 ± 12.5* (30%) |

*p < 0.05 vs. control

Effect of GH-RH Antagonists on H-69 Human SCLC Xenografted into Nude Mice

Male nude mice were implanted s.c. with 3 mm³ pieces of H-69 human SCLC tissue. When tumors reached a volume of approx. 80 mm³ the mice were divided into 4 experimental groups of 7-8 animals each and received the following treatment for 4 weeks: group I (control), vehicle solution; group 2, Peptide 67 (10 μg/day s.c.); group 3, Peptide 31 (10 μg/day s.c.); group 4, Peptide 72 (10 μg/day s.c.). Tumor volumes were recorded twice a week. At the end of treatment, mice were anesthetized with isoflurane, killed by decapitation, and tumors were excised and weighed. Data are presented as means±S.E. Data were evaluated by one way ANOVA and the Student-Newman-Keuls test.

Results

All GH-RH antagonists, given as single daily injections at a dose of 10 μg/day, significantly inhibited the growth of H69 tumors in nude mice. Among the compounds tested, Peptide 72 had the strongest antiproliferative effect (Table XV).

TABLE XV

Effect of Treatment with GH-RH Antagonists on H-69 Human SCLC Xenografts in Nude Mice

| Group | Tumor volume (mm³) Initial | Tumor volume (mm³) Final (% inhibition) |
|---|---|---|
| Control | 81 ± 13 | 2350 ± 189 |
| Peptide 67 | 82 ± 10 | 501 ± 35* (76%) |
| Peptide 31 | 80 ± 6 | 832 ± 23* (67%) |
| Peptide 72 | 81 ± 9 | 308 ± 23* (90%) |

*p < 0.001 vs. control

The invention claimed is:

1. A peptide selected from the group having the formulae:

$R_1$-$A^0$-$A^1$-$A^2$-Asp-Ala-$A^5$-$A^6$-Thr-$A^8$-$A^9$-$A^{10}$-$A^{11}$-$A^{12}$-Val-Leu-$A^{15}$-$A^{16}$-Leu-Ser-$A^{19}$-$A^{20}$-$A^{21}$-$A^{22}$-Leu-Gln-Asp-Ile-$A^{27}$-$A^{28}$-$A^{29}$-$A^{30}$-$R_2$ wherein $R_1$ is a member of the group consisting of a) PhAc, Hca, Dat, IndAc Ipa, 1-Nac, 2-Nac, 1-Npr, 2-Npr, Ibu; $CH_3(CH_2)_nCO$, or $HOOC(CH_2)_nCO$, where n is an integer from 2 to 20, and b) any other straight chain, branch chain, saturated, unsaturated or poly unsaturted aliphatic carboxyl group of 2-30 carbon atoms and any carbocyclic or heterocyclic aromatic carboxyl group of 3-8 carbon atoms containing at least one atom of the group S, N, and O in the hetercyclic ring, $A^0$ is Phe, D-Phe, Arg, D-Arg, or is absent $A^1$ is Tyr or His, $A^2$ is D-Arg or D-Cit, $A^5$ is Ile or Val, $A^6$ is Phe, Tyr, Nal, or Phe(Y), in which Y=F, Cl, Br, or I, $A^8$ is Asn, D-Asn, Cit, D-Cit, Gln, D-Gln, Ser, D-Ser, Thr, D-Thr, Ala, D-Ala, Abu, D-Abu or Aib, $A^9$ is His, D-His, Amp, D-Amp, Gup, or D-Gup, $A^{10}$ is Tyr, Tyr(Et), Tyr(Me); Phe(Y), in which Y=H, F, Cl, Br, or I; Amp, His, Cha, Chg, Bpa, Dip, Trp, Trp(For), Tpi, 1-Nal, 2-Nal, 3-Pal, 4-Pal, Phe($NH_2$), or Phe($NO_2$), $A^{11}$ is His, D-His, Arg, D-Arg, Cit Har, D-Har, Amp, D-Amp, Gup, or D-Gup, $A^{12}$ is Lys, D-Lys, Orn, D-Orn, Har, D-Har, Cit, D-Cit, Nle, or Ala, $A^{15}$ is Gly, Ala, Abu, Aib, Nle, Gln, Cit or His, A$^{16}$ is Gln or Arg,
A$^{19}$ is Ala or Abu,
A$^{20}$ is His, D-His, Arg, D-Arg, or Cit,
A$^{21}$ is Lys, D-Lys, Orn, D-Orn, Cit, or D-Cit,
A$^{22}$ is Leu, Ala or Aib,
A$^{27}$ is Met, Leu, Nle, Abu, or D-Arg,
A$^{28}$ is Arg, D-Arg, Har, D-Har, Ser, Asn, Asp, Ala, Abu, or Cit,
A$^{29}$ is Arg, D-Arg, Har, D-Har, Cit D-Cit, or Agm,
A$^{30}$ is Arg, D-Arg, Har, D-Har, Cit, D-Cit Agm, absent,
R$_2$ is —NH$_2$, —NH—NH$_2$, —NH—OH, —NHR$_3$, —NR$_3$R$_4$, —OH, or —OR$_3$, in which R$_3$ and R$_4$ are any of C$_{1-10}$ alkyl, C$_{2-10}$ alkenyl, C$_{2-10}$ alkinyl, C$_{7-16}$ phenylalkyl, —C$_6$H$_5$, or —CH(C$_6$H$_5$)$_2$;
provided that if A$^{29}$ is Agm then A$^{30}$ and R$_2$ are absent, and if A$^{30}$ is Agm then R$_2$ is absent, and pharmaceutically acceptable salts thereof.

2. The compound of claim 1 wherein one or both of A$^{11}$ and A$^{20}$ are other than Arg, D-Arg, or Cit.

3. A compound of claim 1 selected from the group consisting of:

[PhAc-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 67

[PhAc-Tyr$^1$, D-Arg$^2$, Phe(pCl)$^6$, Amp$^9$, Abu$^{15}$, Nle$^{27}$, D-Arg$^{28}$, Har$^{29}$]hGH-RH(1-29)NH$_2$ Peptide 68

[PhAc-Tyr$^1$, D-Arg$^2$, Phe(pCl)$^6$, His$^9$, Tyr(Me)$^{10}$, Abu$^{15}$, Nle$^{27}$, D-Arg$^{28}$, Har$^{29}$]hGH-RH(1-29)NH$_2$ Peptide 69

[CH$_3$(CH$_2$)$_6$CO-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 70

[HOOC(CH$_2$)$_8$CO-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 71

[HOOC(CH$_2$)$_{12}$CO-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 72

[PhAc-Tyr$^1$, D-Arg$^2$, Phe(pCl)$^6$, Amp$^9$, Tyr(Me)$^{10}$, His$^{11}$, Abu$^{15}$, Nle$^{27}$, D-Arg$^{28}$, Har$^{29}$]hGH-RH(1-29)NH$_2$ Peptide 73

[PhAc-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$^{29}$]hGH-RH(1-29)NH$_2$ Peptide 74

[1-Nac-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$^{29}$]hGH-RH(1-29)NH$_2$ Peptide 75

[CH$_3$(CH$_2$)$_6$CO-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$^{29}$]hGH-RH(1-29)NH$_2$ Peptide 76

[HOC(CH$_2$)$_{12}$CO-Tyr$^1$, D-Arg$^2$, Phe(pCl)$^2$, Cit$^8$, Amp$^9$, Tyr(Me)$^{10}$, His$^{11}$, Abu$^{15}$, Nle$^{27}$, D-Arg$^{28}$, Har$^{29}$]hGH-RH(1-29)NH$_2$ Peptide 77

[CH$_3$(CH$_2$)$_6$CO-Tyr$^1$, D-Arg$^2$, Phe(pCl)$^6$, Cit$^8$, Amp$^9$, Tyr(Et)$^{10}$, His$^{11}$, Abu$^{15}$, Nle$^{27}$, D-Arg$^{28}$, Har$^{29}$]hGH-RH(1-29)NH$_2$ Peptide 78

[CH$_3$(CH$_2$)$_6$CO-Tyr$^1$, D-Arg$^2$, Phe(pCl)$^6$, Cit$^8$, His$^9$, Tyr(Et)$^{10}$, His$^{11}$, Abu$^{15}$, Nle$^{27}$, D-Arg$^{28}$, Har$^{29}$]hGH-RH(1-29)NH$_2$ Peptide 79

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NH$_{12}$ Peptide 80

[HOOC(CH$_{12}$)$_8$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NH$_2$ Peptide 81

[HOOC(CH$_2$)$_{12}$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NH$_2$ Peptide 82

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Abu$^{15}$, His$^{20}$, Nle$^{27}$, D-Arg$^{28}$, Har$^{29}$]hGH-RH(1-29)NH$_2$ Peptide 86

[CH$_3$(CH$_2$)$_6$CO-Tyr$^1$, D-Arg$^2$, Phe(pCl)$^6$, Ala$^8$, Amp$^9$, Tyr(Et)$^{10}$, His$^{11}$, Abu$^{15}$, His$^{20}$, Nle$^{27}$, D-Arg$^{28}$, Har$^{29}$]hGH-RH(1-29)NH$_2$ Peptide 87

[HOOC(CH$_2$)$_{12}$CO-Tyr$^1$, D-Arg$^2$, Phe(pCl)$^6$, Ala$^8$, His$^9$, Tyr(Et)$^{10}$, His$^{11}$, Abu$^{15}$, His$^{20}$, Nle$^{27}$, D-Arg$^{28}$, Har$^{29}$] hGH-RH(1-29)NH$_2$ Peptide 88

[HOOC(CH$_2$)$_{12}$CO-Tyr$^1$, D-Arg$^2$, Phe(pCl)$^6$, Ala$^8$, Amp$^9$, Tyr(Et)$^{10}$, His$^{11}$, Abu$^{15}$, His$^{20}$, Nle$^{27}$, D-Arg$^{28}$, Har$^{29}$] hGH-RH(1-29)NH$_2$ Peptide 89

[1-Nac-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NH$_2$ Peptide 91

[CH$_3$(CH$_2$)$_6$CO-Tyr$^1$, D-Arg$^2$, Phe(pCl)$^6$, His$^9$, Tyr(Et)$^{10}$, His$^{11}$, Abu$^{15}$, Nle$^{27}$, D-Arg$^{28}$, Har$^{29}$]hGH-RH(1-29)NH$_2$ Peptide 92

[CH$_3$(CH$_2$)$_6$CO-Tyr$^1$, D-Arg$^2$, Phe(pCl)$^6$, Ala$^8$, His$^9$, Cit$^{15}$, Nle$^{27}$, D-Arg$^{28}$, Har$^{29}$]hGH-RH(1-29)NH$_2$ Peptide 93

[CH$_3$(CH$_2$)$_6$CO-Tyr$^1$, Arg$^2$, Phe(pCl)$^6$, Ala$^8$, His$^9$, Tyr(Et)$^{10}$, His$^{11}$, His$^{15}$, His$^{20}$, Nle$^{27}$, D-Arg$^{28}$, Har$^{29}$]hGH-RH(1-29)NH$_2$ Peptide 94

[CH$_3$(CH$_2$)$_6$CO-Tyr$^1$, D-Arg$^2$, Phe(pCl)$^6$, Ala$^8$, His$^9$, Tyr(Et)$^{10}$, His11, Orn$^{12}$, Abu$^{15}$, Orn$^{21}$, Nle$^{27}$, D-Arg$^{28}$, Har$^{29}$]hGH-RH(1-29)NH$_2$ Peptide 95

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 96

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NHEt Peptide 97

[CH$_3$(CH$_2$)$_8$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NHEt Peptide 98

[CH$_3$(CH$_2$)$_{10}$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NHEt Peptide 99

[Hca-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NHEt Peptide 100

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NHMe Peptide 101

[HOOC(CH$_2$)$_{12}$CO-Tyr$^1$, D-Arg$^2$, Phe(pCl)$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 102

[CH$_3$(CH$_2$)$_6$CO-Tyr$^1$, D-Arg$^2$, Phe(pCl)$^6$, Ala$^8$, Amp$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 103

[CH$_3$(CH$_2$)$_6$CO-Tyr$^1$, D-Arg$^2$, Phe(pCl)$^6$, Ala$^8$, His$^9$, Dip$^{10}$, His$^{11}$, Orn$^{12}$, Abu$^{15}$, His$^{20}$, Orn$^{21}$, D-Arg$^{28}$, Har$^{29}$]hGH-RH(1-29)NH$_2$ Peptide 104

[CH$_3$(CH$_2$)$_6$CO-Tyr$^1$, D-Arg$^2$, Phe(pCl))$^6$, Ala$^8$, His$^9$, Phe(pNO$_2$)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 105

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 106

[HOOC(CH$_2$)$_{12}$CO-Tyr$^1$, D-Arg$^2$, Phe(pCl)$^6$, Ala$^8$, Amp$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 107

[HOOC(CH$_2$)$_{12}$CO-Tyr$^1$, D-Arg$^2$, Phe(pCl)$^6$, Ala$^8$, His$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 108

[HOOC(CH$_2$)$_{12}$CO-Tyr$^1$, D-Arg$^2$, Phe(pCl)$^6$, Ala$^8$, His$^9$, Phe(pNO$_2$)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 109

[HOOC(CH$_2$)$_{12}$CO-Tyr$^1$, D-Arg$^2$, Phe(pCl)$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 110

[CH$_3$(CH$_2$)$_6$CO-Tyr$^1$, D-Arg$^2$, Phe(pCl)$^6$, Ala$^8$, Amp$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 111

[CH$_3$(CH$_2$)$_6$CO-Tyr$^1$, D-Arg$^2$, Phe(pCl)$^6$, Ala$^8$, Amp$^9$, Phe(pNO$_2$)$^{10}$, His$^{11}$, Orn$^2$, Abu$^{15}$, His$^{20}$, Orn$^{21}$, Nle$^{27}$, D-Arg$^{28}$, Har$^{29}$]hGH-RH(1-29)NH$_2$ Peptide 112

[CH$_3$(CH$_2$)$_6$CO-Tyr$^1$, D-Arg$^2$, Phe(pCl)$^6$, Ala$^8$, Amp$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 113

[CH$_3$(CH$_2$)$_6$CO-Tyr$^1$, D-Arg$^2$, Phe(pCl)$^6$, Ala$^8$, His$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 114

[CH$_3$(CH$_2$)$_6$CO-Tyr$^1$, D-Arg$^2$, Phe(pCl)$^6$, Ala$^8$, His$^9$, Phe(pNO$_2$)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 115

[HOOC(CH$_2$)$_{12}$CO-Tyr$^1$, D-Arg$^2$, Phe(pCl)$^6$, Ala$^8$, Amp$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 116

[HOOC(CH$_2$)$_{12}$CO-Tyr$^1$, D-Arg$^2$, Phe(pCl)$^6$, Ala$^8$, Amp$^9$, Phe(pNO$_2$)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 117

[CH$_3$(CH$_2$)$_6$CO-Tyr$^1$, D-Arg$^2$, Phe(pCl)$^6$, Ala$^8$, Amp$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 118

[CH$_3$(CH$_2$)$_6$CO-Tyr$^1$, D-Arg$^2$, Phe(pCl)$^6$, Ala$^8$, Amp$^9$, Phe(pNO$_2$)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 119

[HOOC(CH$_2$)$_{12}$CO-Tyr$^1$, D-Arg$^2$, Phe(pCl)$^6$, Ala$^8$, Amp$^9$, Dip$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 120 p1

[HOOC(CH$_2$)$_{12}$CO-Tyr$^1$, D-Arg$^2$, Phe(pCl)$^6$, Ala$^8$, Amp$^9$, Phe(pNO$_2$)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NHEt Peptide 121.

4. A compound of claim 3 selected from the group consisting of:

[PhAc-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$^{29}$]hGH-RH(1-29)NH$_2$ Peptide 67

[PhAc-Tyr$^1$, D-Arg$^2$, Phe(pCl)$^6$, His$^9$, Tyr(Me)$^{10}$, Abu$^{15}$, Nle$^{27}$, D-Arg$^{28}$, Har$^{29}$]hGH-RH(1-29)NH$_2$ Peptide 69

[CH$_3$(CH$_2$)$_6$CO-Tyr$^1$, D-Arg$^2$, Phe(pCl)$^6$, Amp$^8$, Tyr(Me)$^{10}$, Abu$^{15}$, Nle$^{27}$, D-Arg$^{28}$, Har$_{29}$]hGH-RH(1-29)NH$_2$ Peptide 70

[HOOC(CH$_2$)$_{12}$CO-Tyr$^1$, D-Arg$^2$, Phe(pCl)$^6$, Amp$^9$, Tyr(Me)$^{10}$, Abu$^{15}$, Nle$^{27}$, D-Arg$^{28}$, Har$_{29}$]hGH-RH(1-29)NH$_2$ Peptide 72

[CH$_3$(CH$_2$)$_6$CO-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$_{29}$]hGH-RH(1-29)NH$_2$ Peptide 76

[HOOC(CH$_2$)$_{12}$CO-Tyr$^1$, D-Arg$^2$, Phe(pCl)$^6$, Cit$^8$, Amp$^9$, Tyr(Me)$^{10}$, His$^{11}$, Abu$^{15}$, Nle$^{27}$, D-Arg$^{28}$, Har$_{29}$]hGH-RH(1-29)NH$_2$ Peptide 77

[CH$_3$(CH$_2$)$_6$CO-Tyr$^1$, D-Arg$^2$, Phe(pCl)$^6$, Cit$^8$, His$^9$, Tyr(Et)$^{10}$, His$^{11}$, Abu$^{15}$, Nle$^{27}$, D-Arg$^{28}$, Har$_{29}$]hGH-RH(1-29)NH$_2$ Peptide 79

[CH$_3$(CH$_2$)$_6$CO-Tyr$^1$, D-Arg$^2$, Phe(pCl)$^6$, Ala$^8$, Tyr(Et)$^{10}$, His$^{11}$, Abu$^{15}$, Nle$^{27}$, D-Arg$^{28}$, Har$_{29}$]hGH-RH(1-29)NH$_2$ Peptide 80

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Abu$^{15}$, His$^{20}$, Nle$^{27}$, D-Arg$^{28}$, Har$_{29}$]hGH-RH(1-29)NH$_2$ Peptide 86

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Orn$^{12}$, Abu$^{15}$, Orn$^{21}$, Nle$^{27}$, D-Arg$^{28}$, Har$^{29}$]hGH-RH(1-29)NH$_2$ Peptide 95

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ Peptide 96

[CH$_3$(CH$_2$)$_6$CO-Tyr$^1$, D-Arg$^2$, Phe(pCl)$^6$, Ala$^8$, His$^9$, Tyr(Et)$^{10}$, His$^{11}$, Abu$^{15}$, Nle$^{27}$, D-Arg$^{28}$, Har$^{29}$]hGH-RH(1-29)NHEt Peptide 97.

5. A compound selected from the group consisting of:

[CH$_3$(CH$_2$)$_4$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 2

[HOOC(CH$_2$)$_4$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 3

[CH$_3$(CH$_2$)$_6$CO-Tyr$_1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 4

[HOOC(CH$_2$)$_6$CO-Tyr$_1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 5

[CH$_3$(CH$_2$)$_8$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 6

[HOOC(CH$_2$)$_8$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 7

[CH$_3$(CH$_2$)$_{10}$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 8

[HOOC(CH$_2$)$_{10}$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 9

[CH$_3$(CH$_2$)$_{12}$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 10

[HOOC(CH$_2$)$_{12}$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 11

[CH$_3$(CH$_2$)$_{14}$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 12

[HOOC(CH$_2$)$_{14}$CO-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 13

[CH$_3$(CH$_2$)$_6$CO-Tyr$^1$, D-Arg$^2$, Phe(pCl)$^6$, Arg$^9$, Abu$^{15}$, Nle$^{27}$, Har$^{28}$, D-Arg$^{29}$]hGH-RH(1-29)NH$_2$ Peptide 14

[PhAc-Tyr$^1$, D-Arg$^2$, Phe(pCl)$^6$, Arg$^9$, Abu$^{15}$, Nle$^{27}$, Har$^{28}$, D-Arg$^{29}$]hGH-RH(1-29)NH$_2$ Peptide 15

[CH$_3$(CH$_2$)$_{14}$CO-Phe$^0$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 16

[CH$_3$(CH$_2$)$_{14}$CO-D-Phe$^0$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 17

[PhAc-Arg$^0$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 18

[PhAc-D-Arg$^0$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 19

[PhAc-Tyr$^1$, D-Arg$^2$, Phe(pCl)$^6$, Cit$^8$, Arg$^9$, Abu$^{15}$, Nle$^{27}$, D-Arg$^{28}$, Har$^{29}$]hGH-RH(1-29)NH$_2$ Peptide 21

[PhAc-Tyr$^1$, D-Arg$^2$, Phe(Cl)$^6$, Cit$^8$, Cit$^9$, Abu$^{15}$, Nle$^{27}$, D-Arg$^{27}$, Har$^{29}$]hGH-RH(1-29)NH$_2$ Peptide 22

[PhAc-Tyr$^1$, D-Arg$^2$, Phe(pCl)$^6$, Cit$^8$, Arg$^9$, Abu$^{15}$, Nle$^{27}$, Har$^{28}$, D-Arg$^{29}$]hGH-RH(1-29)NH$_2$ Peptide 23

[PhAc-Tyr$^1$, D-Arg$^2$, Phe(pCl)$^6$, Cit$^8$, Cit$^9$, Abu$^{15}$, Nle$^{27}$, Har$^{28}$, D-Arg$^{29}$]hGH-RH(1-29)NH$_2$ Peptide 24

[HOOC(CH$_2$)$_{12}$CO-Tyr$^1$, D-Arg$^2$, Phe(pCl)$^6$, Cit$^8$, Cit$^9$, Abu$^{15}$, Nle$^{27}$, D-Arg$^{28}$, Har$^{29}$]hGH-RH(1-29)NH$_2$ Peptide 25

[PhAc-Tyr$^1$, D-Arg$^2$, Phe(pCl)$^6$, D-Ala$^8$, Arg$^9$, Abu$^{15}$, Nle$^{27}$, D-Arg$^{28}$, Har$^{29}$]hGH-RH(1-29)NH$_2$ Peptide 26

[PhAc-Tyr$^1$, D-Arg$^2$, Phe(pCl)$^6$, Cit$^9$, Abu$^{15}$, Nle$^{27}$, Har$^{28}$, D-Arg$^{29}$]hGH-RH(1-29)NH$_2$ Peptide 28

[PhAC-Tyr$^1$, D-Arg$^2$, Phe(pCl)$^6$, Arg$^9$, Amp$^{10}$, Abu$^{15}$, Nle$^{27}$, D-Arg$^{28}$, Har$^{29}$]hGH-RH(1-29)NH$_2$ Peptide 30

[PhAc-Tyr$^1$, D-Arg$^2$, Phe(pCl)$^6$, Har$^9$, Amp$^{10}$, Abu$^{15}$, Nle$^{27}$, D-Arg$^{28}$, Har$^{29}$]hGH-RH(1-29)NH$_2$ Peptide 31

[PhAc-Tyr$^1$, D-Arg$^2$, Phe(pCl)$^6$, Arg$^9$, His$^{10}$, Abut$^{15}$, Nle$^{27}$, Arg$^{28}$, Har$^{29}$]hGH-RH(1-29)NH$_2$ Peptide 32

[PhAc-Tyr$^1$, D-Arg$^2$, Phe(pCl)$^6$, Arg$^9$, Cha$^{10}$, Abu$^{15}$, Nle$^{27}$, D-Arg$^{28}$, Har$^{29}$]hGH-RH(1-29)NH$_2$ Peptide 33

[PhAc-Tyr$^1$, D-Arg$^2$, Phe(pCl)$^6$, Har$^9$, Tpi$^{10}$, Abu$^{15}$, Nle$^{27}$, D-Arg$^{28}$, Har$^{29}$]hGH-RH(1-29)NH$_2$ Peptide 34

[PhAc-Tyr$^1$, D-Arg$^2$, Phe(pCl)$^6$, Har$^9$, 2-Nal$^{10}$, Abu$^{15}$, Nle$^{27}$, D-Arg$^{28}$, Har$^{29}$]hGH-RH(1-29) NH$_2$ Peptide 35

[PhAc-Tyr$^1$, D-Arg$^2$, Phe(pCl)$^6$, Har$^9$, Dip$^{10}$, Abu$^{15}$, Nle$^{27}$, D-Arg$^{28}$, Har$^{29}$]hGH-RH(1-29)NH$_2$ Peptide 36

[PhAc-Tyr$^1$, D-Arg$^2$, Phe(pCl)$^6$, Har$^9$, Phe(pNH$_2$)$^{10}$, Abu$^{15}$, Nle$^{27}$, D-Arg$^{28}$, Har$^{29}$]hGH-RH(1-29)NH$_2$ Peptide 37

[PhAr-Tyr$^1$, D-Arg$^2$, Phe(pCl)$^6$, Har$^9$, Trp$^{10}$, Abu$^{15}$, Nle$^{27}$, D-Arg$^{28}$, Har$^{29}$]hGH-RH(1-29)NH$_2$ Peptide 38

[PhAc-Tyr$^1$, D-Arg$^2$, Phe(pCl)$^6$, Har$^9$, Phe(pNO$_2$)$^{10}$, Abu$^{15}$, Nle$^{27}$, D-Arg$^{28}$, Har$^{29}$]hGH-RH(1-29)NH$_2$ Peptide 39

[PhAc-Tyr$^1$, D-Arg$^2$, Phe(pCl)$^6$, Har$^9$, 3-Pal$^{10}$, Abu$^{15}$, Nle$^{27}$, D-Arg$^{28}$, Har$^{29}$]hGH-RH(1-29)NH$_2$ Peptide 40

[PhAc-Tyr$^1$, D-Arg$^2$, Phe(pCl)$^6$, Har$^9$, Tyr(Et)$^{10}$, Abu$^{15}$, Nle$^{27}$, D-Arg$^{28}$, Har$^{29}$]hGH-RH(1-29)NH$_2$ Peptide 41

[PhAc-His$^1$, D-Arg$^2$, Tyr$^6$, Har$^9$, Bpa$^{10}$, Abu$^{15}$, Nle$^{27}$, D-Arg$^{28}$, Har$^{29}$]hGH-RH(1-29)NH$_2$ Peptide 42

[PhAc-Tyr$^1$, D-Arg$^2$, Phe(pCl)$^6$, Arg$^9$, Har$^{12}$, Abu$^{15}$, Nle$^{27}$, D-Arg$_{28}$, Har$^{29}$]hGH-RH(1-29)NH$_2$ Peptide 43

[Hca-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$]hGH-RH(1-29)NHEt Peptide 45

[PhAc-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$]hGH-RH(1-29)NHEt Peptide 46

[Hca-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NHEt Peptide 47

[PhAc-Tyr$^1$, D-Arg$^2$, Phe(pCl)$^6$, Arg$^9$, Abu$^{15}$, Nle$^{27}$, D-Arg$^{28}$, Har$^{29}$]hGH-RH(1-29)NHEt Peptide 48

[PhAc-Tyr$^1$, D-Arg$^2$, Phe(pCl)$^6$, Har$^9$, Tyr(Me)$^{10}$, Aib$^{15}$, Nle$^{27}$, D-Arg$^{28}$, Har$^{29}$]hGH-RH(1-29)NHEt Peptide 49

[PhAC-Tyr$^1$, D-Arg$^2$, Phe(pCl)$^6$, Har$^9$, Tyr(Me)$^{10}$, Orn$^{12}$, Abu$^{15}$, Nle$^{27}$, D-Arg$^{28}$, Har$^{29}$]hGH-RH(1-29)NHEt Peptide 50

[Hca-Tyr$^1$, D-Arg$^2$, Phe(pCl)$^6$, Har$^9$, Tyr(Me)$^{10}$, Abu$^{15}$, Nle$^{27}$, D-Arg$^{28}$, Agm$^{29}$]hGH-RH(1-29) Peptide 51

[PhAc-Tyr$^1$, D-Arg$^2$, Phe(pCl)$^6$, Har$^9$, Tyr(Me)$^{10}$, Abu$^{15}$, Nle$^{27}$, D-Arg$^{28}$, Agm$^{29}$]hGH-RH(1-29) Peptide 52

[Hca-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, Har$^{30}$]hGH-RH(1-30)NH$_2$ Peptide 53

[Dat-Tyr$^1$, D-Arg$^2$, Phe(pCl)$^5$, Har$^9$, Tyr(Me)$^{10}$, Abu$^{15}$, Nle$^{27}$, D-Arg$^{28}$, Har$^{29}$, Har$^{30}$]hGH-RH(1-30)NH$_2$ Peptide 54

[Ipa-Tyr$^1$, D-Arg$^2$, Phe(pCl)$^6$, Har$^9$, Tyr(Me)$^{10}$, Abu$^{15}$, Nle$^{27}$, D-Arg-$^{28}$, Har$^{29}$, Har$^{30}$]hGH-RH(1-30)NH$_2$ Peptide 55

[Hca-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, Har$^{30}$]hGH-RH(1-30)NHEt Peptide 56

[Hca-Tyr$^1$, D-Arg$^2$, Phe(pCl)$^6$, Har$^9$, Tyr(Me)$^{10}$, Abu$^{15}$, Nle$^{27}$, D-Arg$_{28}$, D-Arg$^{29}$, Har$^{30}$]hGH-RH(1-30)NH$_2$ Peptide 57

[Hca-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, D-Arg$^{30}$]hGH-RH(1-30)NH$_2$ Peptide 58

[Hca-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, Agm$^{30}$]hGH-RH(1-30) Peptide 59

[PhAc-Tyr$^1$, D-Arg$^2$, Phe(pCl)$^6$, Har$^9$, Tyr(Me)$^{10}$, Abu$^{15}$, Nle$^{27}$, D-Arg$^{28}$, Har$^{29}$, Agm$^{30}$]hGH-RH(1-30) Peptide 60

[PhAc-Tyr$^1$, D-Arg$^2$, Phe(pCl)$^6$, Har$^9$, Tyr(Me)$^{10}$, His$^{11}$, Abu$^{15}$, Nle$^{27}$, D-Arg$^{28}$, Har$^{29}$]hGH-RH(1-29)NH$_2$ Peptide 62

[PhAc-Tyr$^1$, D-Arg$^2$, Phe(pCl)$^6$, Har$^9$, Tyr(Me)$^{10}$, Har$^{11}$, Abu$^{15}$, Nle$^{27}$, D-Arg$^{28}$, Har$^{29}$]hGH-RH(1-29)NH$_2$ Peptide 63

[PhAc-Tyr$^1$, D-Arg$^2$, Phe(pCl)$^6$, Har$^9$, Tyr(Me)$^{10}$, Amp$^{11}$, Abu$^{15}$, Nle$^{27}$, D-Arg$^{28}$, Har$^{29}$]hGH-RH(1-29)NH$_2$ Peptide 64

[PhAc-Tyr$^1$, D-Arg$^2$, Phe(pCl)$^6$, Har$^9$, Tyr(Me)$^{10}$, Cit$^{11}$, Abu$^{15}$, Nle$^{27}$, D-Arg$^{28}$, Har$^{29}$]hGH-RH(1-29)NH$_2$ Peptide 65

[PhAc-Tyr$^1$, D-Arg$^2$, Phe(pCl)$^6$, Har$^9$, Tyr(Me)$^{10}$, Abu$^{15}$, His$^{20}$, Nle$^{27}$, D-Arg$^{28}$, Har$^{29}$]hGH-RH(1-29)NH$_2$ Peptide 84

[PhAc-Tyr$^1$, D-Arg$^2$, Phe(pCl)$^6$, Har$^9$, Tyr(Me)$^{10}$, His$^{11}$, Abu$^{15}$, His$^{20}$, Nle$^{27}$, D-Arg$^{28}$, Har$_{29}$]hGH-RH(1-29) NH$_2$ Peptide 85

[PhAc-Tyr$^1$, D-Arg$^2$, Phe(pCl)$^6$, Arg$^9$, Cit$^{15}$, Nle$^{27}$, D-Arg$^{28}$, Har$^{29}$]hGH-RH(1-29)NH$_2$ Peptide 90.

6. The method of suppressing IGF-l or IGF-ll levels in the tumor tissue of a patient having a cancer carrying receptors for IGF-l by administering to said patient a suppressively effective amount of a compound of claim 1.

7. The method of suppressing VEGF levels in the tumor tissue of a patient having a cancer by administering to said patient a suppressively effective amount of a compound of claim 1.

8. The method of suppressing levels of IGF-l in a patient in need of same by administering to said patient a suppressively effective amount of a compound of claim 1.

9. The method of suppressing serum IGF-l levels in a patient having a cancer carrying receptors for IGF-l by administering to said patient a suppressively effective amount of a compound of claim 1.

10. The method of suppressing GH levels in a patient having a cancer carrying receptors for IGF-l or GH by administering to said patient a suppressively effective amount of a compound of claim 1.

11. A pharmacologically administrable composition consisting essentially of a compound of claim 1 and a pharmacologically acceptable carrier.

* * * * *